US012624475B1

(12) United States Patent
Kohlway et al.

(10) Patent No.: US 12,624,475 B1
(45) Date of Patent: May 12, 2026

(54) CAPTURING GENETIC TARGETS USING A HYBRIDIZATION APPROACH

(71) Applicant: 10x Genomics, Inc., Pleasanton, CA (US)

(72) Inventors: Andrew Scott Kohlway, Pleasanton, CA (US); Francesca Meschi, Pleasanton, CA (US); Jennifer Chew, Pleasanton, CA (US); Joseph Glenn Arthur, Pleasanton, CA (US); Nigel Delaney, Pleasanton, CA (US); Zachary Bent, Pleasanton, CA (US); Katherine Pfeiffer, Pleasanton, CA (US); Andrew John Hill, Pleasanton, CA (US); Luigi Jhon Alvarado Martinez, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 885 days.

(21) Appl. No.: 17/892,598

(22) Filed: Aug. 22, 2022

Related U.S. Application Data

(63) Continuation of application No. PCT/US2021/018795, filed on Feb. 19, 2021.

(60) Provisional application No. 63/077,019, filed on Sep. 11, 2020, provisional application No. 62/979,652, filed on Feb. 21, 2020, provisional application No. 62/980,124, filed on Feb. 21, 2020.

(51) Int. Cl.
*C40B 30/04* (2006.01)
*C12N 15/10* (2006.01)

(52) U.S. Cl.
CPC .......... *C40B 30/04* (2013.01); *C12N 15/1065* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis |
| 4,683,202 | A | 7/1987 | Mullis |
| 4,800,159 | A | 1/1989 | Mullis |
| 4,883,867 | A | 11/1989 | Lee |
| 4,965,188 | A | 10/1990 | Mullis |
| 4,988,617 | A | 1/1991 | Landegren et al. |
| 5,002,882 | A | 3/1991 | Lunnen |
| 5,130,238 | A | 7/1992 | Malek |
| 5,308,751 | A | 5/1994 | Ohkawa |
| 5,321,130 | A | 6/1994 | Yue |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

10xGenomics.com, [online], "Visium Spatial Gene Expression Reagent Kits—Tissue Optimization—User Guide," Feb. 2022, retrieved on Mar. 29, 2024, retrieved from URL<https://cdn.10xgenomics.com/image/upload/v1660261286/support-documents/CG000238_VisiumSpatialTissueOptimizationUserGuide_RevE.pdf>, 46 pages.

(Continued)

*Primary Examiner* — Christian C Boesen
(74) *Attorney, Agent, or Firm* — Fish & Richardson P.C.

(57) ABSTRACT

Provided herein are methods of determining a location of an analyte using hybridization as a method for enhancing detection of the analyte.

26 Claims, 23 Drawing Sheets

(56) References Cited

U.S. PATENT DOCUMENTS

| | | | |
|---|---|---|---|
| 5,410,030 | A | 4/1995 | Yue |
| 5,436,134 | A | 7/1995 | Haugland |
| 5,455,166 | A | 10/1995 | Walker |
| 5,494,810 | A | 2/1996 | Barany et al. |
| 5,503,980 | A | 4/1996 | Cantor |
| 5,512,439 | A | 4/1996 | Hornes |
| 5,512,462 | A | 4/1996 | Cheng |
| 5,582,977 | A | 12/1996 | Yue |
| 5,599,675 | A | 2/1997 | Brenner |
| 5,641,658 | A | 6/1997 | Adams |
| 5,648,245 | A | 7/1997 | Fire et al. |
| 5,658,751 | A | 8/1997 | Yue |
| 5,695,940 | A | 12/1997 | Drmanac et al. |
| 5,750,341 | A | 5/1998 | Macevicz |
| 5,763,175 | A | 6/1998 | Brenner |
| 5,830,711 | A | 11/1998 | Barany et al. |
| 5,837,832 | A | 11/1998 | Chee et al. |
| 5,854,033 | A | 12/1998 | Lizardi |
| 5,863,753 | A | 1/1999 | Haugland |
| 5,871,921 | A | 2/1999 | Landegren et al. |
| 5,912,148 | A | 6/1999 | Eggerding |
| 5,925,545 | A | 7/1999 | Reznikoff et al. |
| 5,928,906 | A | 7/1999 | Koester et al. |
| 5,958,775 | A | 9/1999 | Wickstrrom |
| 5,962,271 | A | 10/1999 | Chenchik et al. |
| 5,962,272 | A | 10/1999 | Chenchik et al. |
| 5,965,443 | A | 10/1999 | Reznikoff et al. |
| 6,013,440 | A | 1/2000 | Lipshutz |
| 6,027,889 | A | 2/2000 | Barany et al. |
| 6,054,274 | A | 4/2000 | Sampson et al. |
| 6,060,240 | A | 5/2000 | Kamb et al. |
| 6,130,073 | A | 10/2000 | Eggerding |
| 6,143,496 | A | 11/2000 | Brown |
| 6,153,389 | A | 11/2000 | Haarer |
| 6,159,736 | A | 12/2000 | Reznikoff et al. |
| 6,165,714 | A | 12/2000 | Lane et al. |
| 6,210,891 | B1 | 4/2001 | Nyren |
| 6,210,894 | B1 | 4/2001 | Brennan |
| 6,214,587 | B1 | 4/2001 | Dattagupta |
| 6,251,639 | B1 | 6/2001 | Kurn |
| 6,258,568 | B1 | 7/2001 | Nyren |
| 6,266,459 | B1 | 7/2001 | Walt |
| 6,268,148 | B1 | 7/2001 | Barany et al. |
| 6,274,320 | B1 | 8/2001 | Rothberg |
| 6,291,180 | B1 | 9/2001 | Chu |
| 6,291,187 | B1 | 9/2001 | Kingsmore et al. |
| 6,300,063 | B1 | 10/2001 | Lipshutz et al. |
| 6,309,824 | B1 | 10/2001 | Drmanac |
| 6,323,009 | B1 | 11/2001 | Lasken et al. |
| 6,344,316 | B1 | 2/2002 | Lockhart |
| 6,344,329 | B1 | 2/2002 | Lizardi et al. |
| 6,355,431 | B1 | 3/2002 | Chee |
| 6,368,801 | B1 | 4/2002 | Faruqi |
| 6,401,267 | B1 | 6/2002 | Drmanac |
| 6,404,907 | B1 | 6/2002 | Gilchrist |
| 6,432,360 | B1 | 8/2002 | Church et al. |
| 6,503,713 | B1 | 1/2003 | Rana |
| 6,506,561 | B1 | 1/2003 | Cheval et al. |
| 6,534,266 | B1 | 3/2003 | Singer |
| 6,544,732 | B1 | 4/2003 | Chee |
| 6,573,043 | B1 | 6/2003 | Cohen et al. |
| 6,579,695 | B1 | 6/2003 | Lambalot |
| 6,620,584 | B1 | 9/2003 | Chee |
| 6,632,641 | B1 | 10/2003 | Brennan |
| 6,737,236 | B1 | 5/2004 | Pieken et al. |
| 6,770,441 | B2 | 8/2004 | Dickinson |
| 6,773,886 | B2 | 8/2004 | Kaufman |
| 6,787,308 | B2 | 9/2004 | Balasubramanian |
| 6,797,470 | B2 | 9/2004 | Barany et al. |
| 6,800,453 | B2 | 10/2004 | Labaer |
| 6,812,005 | B2 | 11/2004 | Fan et al. |
| 6,828,100 | B1 | 12/2004 | Ronaghi |
| 6,833,246 | B2 | 12/2004 | Balasubramanian |
| 6,852,487 | B1 | 2/2005 | Barany et al. |
| 6,859,570 | B2 | 2/2005 | Walt |
| 6,864,052 | B1 | 3/2005 | Drmanac |
| 6,867,028 | B2 | 3/2005 | Janulaitis |
| 6,872,816 | B1 | 3/2005 | Hall et al. |
| 6,875,572 | B2 | 4/2005 | Prudent et al. |
| 6,890,741 | B2 | 5/2005 | Fan et al. |
| 6,897,023 | B2 | 5/2005 | Fu |
| 6,913,881 | B1 | 7/2005 | Aizenstein et al. |
| 6,942,968 | B1 | 9/2005 | Dickinson et al. |
| 7,011,944 | B2 | 3/2006 | Prudent et al. |
| 7,057,026 | B2 | 6/2006 | Barnes |
| 7,083,980 | B2 | 8/2006 | Reznikoff et al. |
| 7,115,400 | B1 | 10/2006 | Adessi |
| 7,118,883 | B2 | 10/2006 | Inoue |
| 7,166,431 | B2 | 1/2007 | Chee et al. |
| 7,192,735 | B2 | 3/2007 | Lambalot |
| 7,211,414 | B2 | 5/2007 | Hardin |
| 7,255,994 | B2 | 8/2007 | Lao |
| 7,258,976 | B2 | 8/2007 | Mitsuhashi |
| 7,282,328 | B2 | 10/2007 | Kong et al. |
| 7,297,518 | B2 | 11/2007 | Quake |
| 7,329,492 | B2 | 2/2008 | Hardin |
| 7,358,047 | B2 | 4/2008 | Hafner et al. |
| 7,361,488 | B2 | 4/2008 | Fan et al. |
| 7,378,242 | B2 | 5/2008 | Hurt |
| 7,393,665 | B2 | 7/2008 | Brenner |
| 7,405,281 | B2 | 7/2008 | Xu |
| 7,407,757 | B2 | 8/2008 | Brenner |
| 7,473,767 | B2 | 1/2009 | Dimitrov |
| 7,499,806 | B2 | 3/2009 | Kermani et al. |
| 7,537,897 | B2 | 5/2009 | Brenner |
| 7,563,576 | B2 | 7/2009 | Chee |
| 7,579,153 | B2 | 8/2009 | Brenner |
| 7,582,420 | B2 | 9/2009 | Oliphant et al. |
| 7,601,498 | B2 | 10/2009 | Mao |
| 7,608,434 | B2 | 10/2009 | Reznikoff et al. |
| 7,611,869 | B2 | 11/2009 | Fan |
| 7,635,566 | B2 | 12/2009 | Brenner |
| 7,666,612 | B2 | 2/2010 | Johnsson |
| 7,674,752 | B2 | 3/2010 | He |
| 7,709,198 | B2 | 5/2010 | Luo et al. |
| 7,776,547 | B2 | 8/2010 | Roth |
| 7,776,567 | B2 | 8/2010 | Mao |
| 7,803,943 | B2 | 9/2010 | Mao |
| 7,888,009 | B2 | 2/2011 | Barany et al. |
| 7,892,747 | B2 | 2/2011 | Barany et al. |
| 7,910,304 | B2 | 3/2011 | Drmanac |
| 7,914,981 | B2 | 3/2011 | Barany et al. |
| 7,955,794 | B2 | 6/2011 | Shen et al. |
| 7,960,119 | B2 | 6/2011 | Chee |
| 7,985,565 | B2 | 7/2011 | Mayer et al. |
| 8,003,354 | B2 | 8/2011 | Shen et al. |
| 8,076,063 | B2 | 12/2011 | Fan |
| 8,092,784 | B2 | 1/2012 | Mao |
| 8,148,068 | B2 | 4/2012 | Brenner |
| 8,206,917 | B2 | 6/2012 | Chee |
| 8,268,554 | B2 | 9/2012 | Schallmeiner |
| 8,288,103 | B2 | 10/2012 | Oliphant |
| 8,288,122 | B2 | 10/2012 | O'Leary et al. |
| 8,383,338 | B2 | 2/2013 | Kitzman |
| 8,431,691 | B2 | 4/2013 | McKernan et al. |
| 8,460,865 | B2 | 6/2013 | Chee |
| 8,481,257 | B2 | 7/2013 | Van Eijk |
| 8,481,258 | B2 | 7/2013 | Church et al. |
| 8,481,292 | B2 | 7/2013 | Casbon |
| 8,481,698 | B2 | 7/2013 | Lieberman et al. |
| 8,507,204 | B2 | 8/2013 | Pierce et al. |
| 8,519,115 | B2 | 8/2013 | Webster et al. |
| 8,551,710 | B2 | 10/2013 | Bernitz et al. |
| 8,568,979 | B2 | 10/2013 | Stuelpnagel et al. |
| 8,586,310 | B2 | 11/2013 | Mitra |
| 8,597,891 | B2 | 12/2013 | Barany et al. |
| 8,603,743 | B2 | 12/2013 | Liu et al. |
| 8,604,182 | B2 | 12/2013 | Luo et al. |
| 8,614,073 | B2 | 12/2013 | Van Eijk |
| 8,624,016 | B2 | 1/2014 | Barany et al. |
| 8,685,889 | B2 | 4/2014 | Van Eijk |
| 8,741,564 | B2 | 6/2014 | Seligmann |
| 8,741,606 | B2 | 6/2014 | Casbon |
| 8,771,950 | B2 | 7/2014 | Church et al. |

(56) References Cited

U.S. PATENT DOCUMENTS 8,785,353 B2 7/2014 Van Eijk
8,790,873 B2 7/2014 Namsaraev et al.
8,809,238 B2 8/2014 Livak et al.
8,815,512 B2 8/2014 Van Eijk
8,835,358 B2 9/2014 Fodor
8,865,410 B2 10/2014 Shendure
8,906,626 B2 12/2014 Oliphant et al.
8,911,945 B2 12/2014 Van Eijk
8,936,912 B2 1/2015 Mitra
8,951,726 B2 2/2015 Luo et al.
8,951,728 B2 2/2015 Rasmussen
8,986,926 B2 3/2015 Ferree et al.
9,005,891 B2 4/2015 Sinicropi et al.
9,005,935 B2 4/2015 Belyaev
9,023,768 B2 5/2015 Van Eijk
9,062,348 B1 6/2015 Van Eijk
9,080,210 B2 7/2015 Van Eijk
9,194,001 B2 11/2015 Brenner
9,201,063 B2 12/2015 Sood et al.
9,273,349 B2 3/2016 Nguyen et al.
9,290,808 B2 3/2016 Fodor
9,290,809 B2 3/2016 Fodor
9,328,383 B2 5/2016 Van Eijk
9,330,295 B2 5/2016 Dunn
9,334,536 B2 5/2016 Van Eijk
9,371,563 B2 6/2016 Geiss et al.
9,371,598 B2 6/2016 Chee
9,376,716 B2 6/2016 Van Eijk
9,376,717 B2 6/2016 Gao et al.
9,376,719 B2 6/2016 Eijk
9,416,409 B2 8/2016 Hayden
9,447,459 B2 9/2016 Van Eijk
9,453,256 B2 9/2016 Van Eijk
9,493,820 B2 11/2016 Van Eijk
9,506,061 B2 11/2016 Brown et al.
9,512,422 B2 12/2016 Barnard et al.
9,574,230 B2 2/2017 Van Eijk
9,593,365 B2 3/2017 Frisen et al.
9,598,728 B2 3/2017 Barany et al.
9,624,538 B2 4/2017 Church et al.
9,644,204 B2 5/2017 Hindson et al.
9,657,335 B2 5/2017 Van Eijk
9,670,542 B2 6/2017 Eijk
9,694,361 B2 7/2017 Bharadwaj
9,702,004 B2 7/2017 Van Eijk
9,714,446 B2 7/2017 Webster et al.
9,714,937 B2 7/2017 Dunaway
9,727,810 B2 8/2017 Fodor et al.
9,745,627 B2 8/2017 Van Eijk
9,777,324 B2 10/2017 Van Eijk
9,783,841 B2 10/2017 Nolan et al.
9,790,476 B2 10/2017 Gloeckner et al.
9,816,134 B2 11/2017 Namsaraev
9,834,814 B2 12/2017 Peter et al.
9,850,536 B2 12/2017 Oliphant et al.
9,856,521 B2 1/2018 Stevens et al.
9,868,979 B2 1/2018 Chee et al.
9,879,313 B2 1/2018 Chee et al.
9,896,721 B2 2/2018 Van Eijk
9,898,576 B2 2/2018 Van Eijk
9,898,577 B2 2/2018 Van Eijk
9,902,991 B2 2/2018 Sinicropi et al.
9,909,167 B2 3/2018 Samusik et al.
9,938,566 B2 4/2018 Shepard et al.
9,957,550 B2 5/2018 Yeakley et al.
10,002,316 B2 6/2018 Fodor et al.
10,023,907 B2 7/2018 Van Eijk
10,030,261 B2 7/2018 Frisen et al.
10,035,992 B2 7/2018 Gloeckner et al.
10,041,949 B2 8/2018 Bendall et al.
10,059,989 B2 8/2018 Giresi et al.
10,059,990 B2 8/2018 Boyden et al.
10,095,832 B2 10/2018 Van Eijk
10,101,336 B2 10/2018 Bergo
10,144,966 B2 12/2018 Cantor
10,208,982 B2 2/2019 Bannish et al.
10,227,639 B2 3/2019 Levner et al.
10,273,541 B2 4/2019 Hindson et al.
10,308,982 B2 6/2019 Chee
10,357,771 B2 7/2019 Bharadwaj
10,370,698 B2 8/2019 Nolan et al.
10,415,080 B2 9/2019 Dunaway et al.
10,465,235 B2 11/2019 Gullberg et al.
10,472,669 B2 11/2019 Chee
10,480,022 B2 11/2019 Chee
10,480,029 B2 11/2019 Bent et al.
10,494,667 B2 12/2019 Chee
10,495,554 B2 12/2019 Deisseroth et al.
10,501,777 B2 12/2019 Beechem et al.
10,501,791 B2 12/2019 Church et al.
10,510,435 B2 12/2019 Cai et al.
10,544,403 B2 1/2020 Gloeckner et al.
10,550,429 B2 2/2020 Harada et al.
10,590,244 B2 3/2020 Delaney et al.
10,633,648 B2 4/2020 Seelig et al.
10,640,816 B2 5/2020 Beechem et al.
10,640,826 B2 5/2020 Church et al.
10,662,468 B2 5/2020 Chee
10,669,569 B2 6/2020 Gullberg et al.
10,724,078 B2 7/2020 Van Driel et al.
10,725,027 B2 7/2020 Bell
10,774,372 B2 9/2020 Chee et al.
10,774,374 B2 9/2020 Frisen et al.
10,787,701 B2 9/2020 Chee
10,815,519 B2 10/2020 Husain et al.
10,829,803 B2 11/2020 Terbrueggen et al.
10,844,426 B2 11/2020 Daugharthy et al.
10,858,698 B2 12/2020 Church et al.
10,858,702 B2 12/2020 Lucero et al.
10,913,975 B2 2/2021 So et al.
10,914,730 B2 2/2021 Chee et al.
10,927,403 B2 2/2021 Chee et al.
10,961,566 B2 3/2021 Chee
11,001,879 B1 5/2021 Chee
11,008,607 B2 5/2021 Chee
11,046,996 B1 6/2021 Chee et al.
11,067,567 B2 7/2021 Chee
11,104,936 B2 8/2021 Zhang et al.
11,118,216 B2 9/2021 Koshinsky et al.
11,156,603 B2 10/2021 Chee
11,162,132 B2 11/2021 Frisen et al.
11,208,684 B2 12/2021 Chee
11,214,796 B2 1/2022 Shirai et al.
11,286,515 B2 3/2022 Chee et al.
11,293,917 B2 4/2022 Chee
11,299,774 B2 4/2022 Frisen et al.
11,313,856 B2 4/2022 Chee
11,332,790 B2 5/2022 Chell et al.
11,352,659 B2 6/2022 Frisen et al.
11,352,667 B2 6/2022 Hauling et al.
11,359,228 B2 6/2022 Chee et al.
11,365,442 B2 6/2022 Chee
11,371,086 B2 6/2022 Chee
11,384,386 B2 7/2022 Chee
11,390,912 B2 7/2022 Frisen et al.
11,401,545 B2 8/2022 Chee
11,407,992 B2 8/2022 Dadhwal
11,408,029 B2 8/2022 Katiraee et al.
11,434,524 B2 9/2022 Ramachandran Iyer et al.
11,459,607 B1 10/2022 Terry et al.
11,479,809 B2 10/2022 Frisen et al.
11,479,810 B1 10/2022 Chee
11,492,612 B1 11/2022 Dadhwal
11,501,440 B2 11/2022 Weisenfeld et al.
11,505,828 B2 11/2022 Chell et al.
11,512,308 B2 11/2022 Gallant et al.
11,519,022 B2 12/2022 Chee
11,519,033 B2 12/2022 Schnall-Levin et al.
11,519,138 B2 12/2022 Meier
11,530,438 B2 12/2022 Persson et al.
11,535,887 B2 12/2022 Gallant et al.
11,542,543 B2 1/2023 Chee
11,549,138 B2 1/2023 Chee
11,560,587 B2 1/2023 Chee

(56) References Cited

U.S. PATENT DOCUMENTS

| | | | |
|---|---|---|---|
| 11,560,592 | B2 | 1/2023 | Chew et al. |
| 11,560,593 | B2 | 1/2023 | Chell et al. |
| 11,592,447 | B2 | 2/2023 | Uytingco et al. |
| 11,608,498 | B2 | 3/2023 | Gallant et al. |
| 11,608,520 | B2 | 3/2023 | Galonska et al. |
| 11,613,773 | B2 | 3/2023 | Frisen et al. |
| 11,618,897 | B2 | 4/2023 | Kim et al. |
| 11,618,918 | B2 | 4/2023 | Chee et al. |
| 11,624,063 | B2 | 4/2023 | Dadhwal |
| 11,624,086 | B2 | 4/2023 | Uytingco et al. |
| 11,634,756 | B2 | 4/2023 | Chee |
| 11,649,485 | B2 | 5/2023 | Yin et al. |
| 11,661,626 | B2 | 5/2023 | Katiraee et al. |
| 11,680,260 | B2 | 6/2023 | Kim et al. |
| 11,692,218 | B2 | 7/2023 | Engblom et al. |
| 11,702,693 | B2 | 7/2023 | Bharadwaj |
| 11,702,698 | B2 | 7/2023 | Stoeckius |
| 11,713,480 | B2 | 8/2023 | Lee |
| 11,732,292 | B2 | 8/2023 | Chee |
| 11,732,299 | B2 | 8/2023 | Ramachandran Iyer |
| 11,732,300 | B2 | 8/2023 | Bava |
| 11,733,238 | B2 | 8/2023 | Chee |
| 11,739,372 | B2 | 8/2023 | Frisen et al. |
| 11,739,381 | B2 | 8/2023 | Chew et al. |
| 11,753,673 | B2 | 9/2023 | Chew et al. |
| 11,753,674 | B2 | 9/2023 | Chee et al. |
| 11,753,675 | B2 | 9/2023 | Ramachandran Iyer |
| 11,761,030 | B2 | 9/2023 | Chee |
| 11,761,038 | B1 | 9/2023 | Stoeckius |
| 11,767,550 | B2 | 9/2023 | Chee |
| 11,768,175 | B1 | 9/2023 | Kim et al. |
| 11,773,433 | B2 | 10/2023 | Gallant et al. |
| 11,781,130 | B2 | 10/2023 | Dadhwal |
| 11,788,122 | B2 | 10/2023 | Frisen et al. |
| 11,795,498 | B2 | 10/2023 | Frisen et al. |
| 11,795,507 | B2 | 10/2023 | Chell et al. |
| 11,808,769 | B2 | 11/2023 | Uytingco et al. |
| 11,821,024 | B2 | 11/2023 | Chee et al. |
| 11,821,035 | B1 | 11/2023 | Bent et al. |
| 11,827,935 | B1 | 11/2023 | Ramachandran Iyer et al. |
| 11,835,462 | B2 | 12/2023 | Bava |
| 11,840,687 | B2 | 12/2023 | Gallant et al. |
| 11,840,724 | B2 | 12/2023 | Chew et al. |
| 11,845,979 | B2 | 12/2023 | Engblom et al. |
| 11,859,178 | B2 | 1/2024 | Gallant et al. |
| 11,866,767 | B2 | 1/2024 | Uytingco et al. |
| 11,866,770 | B2 | 1/2024 | Chee |
| 11,873,482 | B2 | 1/2024 | Kim et al. |
| 11,891,654 | B2 | 2/2024 | Alvarado Martinez et al. |
| 11,898,205 | B2 | 2/2024 | Bava |
| 11,926,822 | B1 | 3/2024 | Gohil et al. |
| 11,926,863 | B1 | 3/2024 | Boutet |
| 11,926,867 | B2 | 3/2024 | Yin et al. |
| 11,933,957 | B1 | 3/2024 | Tentori et al. |
| 11,952,627 | B2 | 4/2024 | Stoeckius |
| 11,959,076 | B2 | 4/2024 | Kim et al. |
| 11,959,130 | B2 | 4/2024 | Galonska et al. |
| 11,965,213 | B2 | 4/2024 | Williams |
| 11,970,739 | B2 | 4/2024 | Chew et al. |
| 11,981,958 | B1 | 5/2024 | Galonska |
| 11,981,960 | B1 | 5/2024 | Lin et al. |
| 11,981,965 | B2 | 5/2024 | Chell et al. |
| RE50,065 | E | 7/2024 | Frisen et al. |
| 12,024,741 | B2 | 7/2024 | Tentori et al. |
| 12,031,177 | B1 | 7/2024 | Tentori et al. |
| 12,060,604 | B2 | 8/2024 | Katiraee et al. |
| 12,071,655 | B2 | 8/2024 | Sukovich et al. |
| 12,076,701 | B2 | 9/2024 | Bava |
| 12,098,417 | B2 | 9/2024 | Engblom et al. |
| 12,098,985 | B2 | 9/2024 | Cox et al. |
| 12,110,541 | B2 | 10/2024 | Bava |
| 12,117,439 | B2 | 10/2024 | Delaney et al. |
| 12,128,403 | B2 | 10/2024 | Kim et al. |
| 12,129,516 | B2 | 10/2024 | Tentori et al. |
| 12,157,124 | B2 | 12/2024 | Cox et al. |
| 12,180,543 | B2 | 12/2024 | Uytingco et al. |
| 12,195,790 | B2 | 1/2025 | Sukovich et al. |
| 12,203,134 | B2 | 1/2025 | Nagendran et al. |
| 12,209,280 | B1 | 1/2025 | Mignardi et al. |
| 12,223,751 | B2 | 2/2025 | Li et al. |
| 12,228,544 | B2 | 2/2025 | Kim et al. |
| 12,234,505 | B2 | 2/2025 | Chee |
| 12,241,060 | B2 | 3/2025 | Kim et al. |
| 12,241,890 | B2 | 3/2025 | Delaney et al. |
| 12,249,085 | B2 | 3/2025 | Tentori et al. |
| 12,265,079 | B1 | 4/2025 | Bent |
| 12,270,077 | B2 | 4/2025 | Schnall-Levin et al. |
| 12,275,988 | B2 | 4/2025 | Galonska et al. |
| 12,281,357 | B1 | 4/2025 | Tentori et al. |
| 12,286,673 | B2 | 4/2025 | Bava |
| 12,287,264 | B2 | 4/2025 | Cox et al. |
| 12,297,486 | B2 | 5/2025 | Patterson et al. |
| 12,297,487 | B2 | 5/2025 | Chee |
| 12,297,488 | B2 | 5/2025 | Chee |
| 12,344,892 | B2 | 7/2025 | Schnall-Levin et al. |
| 12,365,935 | B2 | 7/2025 | Chew et al. |
| 12,365,942 | B2 | 7/2025 | Stoeckius |
| 12,371,688 | B2 | 7/2025 | Kim et al. |
| 12,378,607 | B2 | 8/2025 | Schnall-Levin et al. |
| 12,385,083 | B2 | 8/2025 | Shah |
| 12,391,979 | B2 | 8/2025 | Chee |
| 12,391,980 | B2 | 8/2025 | Chee |
| 12,399,123 | B1 | 8/2025 | Shah et al. |
| 12,404,544 | B2 | 9/2025 | Tentori et al. |
| 12,405,264 | B2 | 9/2025 | Stoeckius |
| 12,416,603 | B2 | 9/2025 | Tentori et al. |
| 12,435,363 | B1 | 10/2025 | Gallant et al. |
| 12,442,045 | B2 | 10/2025 | Williams |
| 2001/0055764 | A1 | 12/2001 | Empendocles et al. |
| 2002/0040275 | A1 | 4/2002 | Cravatt |
| 2002/0051986 | A1 | 5/2002 | Baez et al. |
| 2002/0055100 | A1 | 5/2002 | Kawashima |
| 2002/0058250 | A1 | 5/2002 | Firth |
| 2002/0086441 | A1 | 7/2002 | Baranov et al. |
| 2002/0164611 | A1 | 11/2002 | Bamdad |
| 2003/0017451 | A1 | 1/2003 | Wang et al. |
| 2003/0022207 | A1 | 1/2003 | Balasubramanian |
| 2003/0064398 | A1 | 4/2003 | Barnes |
| 2003/0092624 | A1 | 5/2003 | Wang et al. |
| 2003/0138879 | A1 | 7/2003 | Lambalot |
| 2003/0148335 | A1 | 8/2003 | Shen et al. |
| 2003/0162216 | A1 | 8/2003 | Gold |
| 2003/0165948 | A1 | 9/2003 | Alsmadi et al. |
| 2003/0211489 | A1 | 11/2003 | Shen et al. |
| 2003/0224419 | A1 | 12/2003 | Corcoran |
| 2003/0232348 | A1 | 12/2003 | Jones et al. |
| 2003/0232382 | A1 | 12/2003 | Brennan |
| 2003/0235854 | A1 | 12/2003 | Chan et al. |
| 2004/0009487 | A1 | 1/2004 | Kadushin et al. |
| 2004/0033499 | A1 | 2/2004 | Ilsley et al. |
| 2004/0067492 | A1 | 4/2004 | Peng et al. |
| 2004/0082059 | A1 | 4/2004 | Webb et al. |
| 2004/0096853 | A1 | 5/2004 | Mayer |
| 2004/0106110 | A1 | 6/2004 | Balasubramanian |
| 2004/0235103 | A1 | 11/2004 | Reznikoff et al. |
| 2004/0241660 | A1 | 12/2004 | Wojtowicz et al. |
| 2004/0248325 | A1 | 12/2004 | Bukusoglu et al. |
| 2004/0259105 | A1 | 12/2004 | Fan et al. |
| 2005/0003431 | A1 | 1/2005 | Wucherpfennig |
| 2005/0014203 | A1 | 1/2005 | Darfler et al. |
| 2005/0037393 | A1 | 2/2005 | Gunderson et al. |
| 2005/0048580 | A1 | 3/2005 | Labaer |
| 2005/0064460 | A1 | 3/2005 | Holliger et al. |
| 2005/0095627 | A1 | 5/2005 | Kolman et al. |
| 2005/0100900 | A1 | 5/2005 | Kawashima et al. |
| 2005/0130173 | A1 | 6/2005 | Leamon et al. |
| 2005/0136414 | A1 | 6/2005 | Gunderson et al. |
| 2005/0164292 | A1 | 7/2005 | Farooqui |
| 2005/0170373 | A1 | 8/2005 | Monforte |
| 2005/0191656 | A1 | 9/2005 | Drmanac et al. |
| 2005/0191698 | A1 | 9/2005 | Chee et al. |
| 2005/0202433 | A1 | 9/2005 | Van Beuningen |
| 2005/0227271 | A1 | 10/2005 | Kwon |
| 2005/0239119 | A1 | 10/2005 | Tsukada et al. |

(56) References Cited

U.S. PATENT DOCUMENTS

| | | | |
|---|---|---|---|
| 2005/0260653 | A1 | 11/2005 | LaBaer |
| 2005/0266417 | A1 | 12/2005 | Barany et al. |
| 2006/0041385 | A1 | 2/2006 | Bauer et al. |
| 2006/0046313 | A1 | 3/2006 | Roth |
| 2006/0084078 | A1 | 4/2006 | Zhao |
| 2006/0105352 | A1 | 5/2006 | Qiao et al. |
| 2006/0154286 | A1 | 7/2006 | Kong et al. |
| 2006/0188901 | A1 | 8/2006 | Barnes et al. |
| 2006/0199183 | A1 | 9/2006 | Valat et al. |
| 2006/0211001 | A1 | 9/2006 | Yu et al. |
| 2006/0216775 | A1 | 9/2006 | Burkart et al. |
| 2006/0240439 | A1 | 10/2006 | Smith et al. |
| 2006/0263789 | A1 | 11/2006 | Kincaid |
| 2006/0275782 | A1 | 12/2006 | Gunderson et al. |
| 2006/0281109 | A1 | 12/2006 | Barr Ost et al. |
| 2007/0020640 | A1 | 1/2007 | McCloskey et al. |
| 2007/0020669 | A1 | 1/2007 | Ericsson |
| 2007/0026430 | A1 | 2/2007 | Andersen et al. |
| 2007/0054288 | A1 | 3/2007 | Su et al. |
| 2007/0087360 | A1 | 4/2007 | Boyd |
| 2007/0099208 | A1 | 5/2007 | Drmanac et al. |
| 2007/0128624 | A1 | 6/2007 | Gormley et al. |
| 2007/0128656 | A1 | 6/2007 | Agrawal |
| 2007/0134723 | A1 | 6/2007 | Kozlov et al. |
| 2007/0161020 | A1 | 7/2007 | Luo et al. |
| 2007/0166705 | A1 | 7/2007 | Milton et al. |
| 2007/0172873 | A1 | 7/2007 | Brenner et al. |
| 2007/0207482 | A1 | 9/2007 | Church et al. |
| 2007/0254305 | A1 | 11/2007 | Paik et al. |
| 2007/0269805 | A1 | 11/2007 | Hogers |
| 2008/0003586 | A1 | 1/2008 | Hyde et al. |
| 2008/0009420 | A1 | 1/2008 | Schroth et al. |
| 2008/0108082 | A1 | 5/2008 | Rank et al. |
| 2008/0108804 | A1 | 5/2008 | Hayashizaki et al. |
| 2008/0132429 | A1 | 6/2008 | Perov et al. |
| 2008/0160580 | A1 | 7/2008 | Adessi et al. |
| 2008/0220434 | A1 | 9/2008 | Thomas |
| 2008/0261204 | A1 | 10/2008 | Lexow |
| 2008/0286795 | A1 | 11/2008 | Kawashima et al. |
| 2008/0293046 | A1 | 11/2008 | Allawi et al. |
| 2009/0005252 | A1 | 1/2009 | Drmanac et al. |
| 2009/0006002 | A1 | 1/2009 | Honisch et al. |
| 2009/0018024 | A1 | 1/2009 | Church et al. |
| 2009/0026082 | A1 | 1/2009 | Rothberg et al. |
| 2009/0036323 | A1 | 2/2009 | van Eijk et al. |
| 2009/0082212 | A1 | 3/2009 | Williams |
| 2009/0099041 | A1 | 4/2009 | Church et al. |
| 2009/0105959 | A1 | 4/2009 | Braverman et al. |
| 2009/0117573 | A1 | 5/2009 | Fu et al. |
| 2009/0127589 | A1 | 5/2009 | Rothberg et al. |
| 2009/0155781 | A1 | 6/2009 | Drmanac et al. |
| 2009/0170713 | A1 | 7/2009 | van Eijk et al. |
| 2009/0202998 | A1 | 8/2009 | Schlumpberger et al. |
| 2009/0233802 | A1 | 9/2009 | Bignell et al. |
| 2009/0253581 | A1 | 10/2009 | van Eijk et al. |
| 2009/0270273 | A1 | 10/2009 | Burns et al. |
| 2009/0283407 | A1 | 11/2009 | Van Eijk |
| 2009/0286249 | A1 | 11/2009 | Becker et al. |
| 2009/0291854 | A1 | 11/2009 | Weisinger-Mayr et al. |
| 2009/0312193 | A1 | 12/2009 | Kim et al. |
| 2010/0035249 | A1 | 2/2010 | Hayashizaki et al. |
| 2010/0047790 | A1 | 2/2010 | Southern et al. |
| 2010/0069263 | A1 | 3/2010 | Shendure et al. |
| 2010/0105052 | A1 | 4/2010 | Drmanac et al. |
| 2010/0120097 | A1 | 5/2010 | Matz et al. |
| 2010/0120098 | A1 | 5/2010 | Grunenwald et al. |
| 2010/0129874 | A1 | 5/2010 | Mitra et al. |
| 2010/0145037 | A1 | 6/2010 | Brive et al. |
| 2010/0173384 | A1 | 7/2010 | Johnsson et al. |
| 2010/0184618 | A1 | 7/2010 | Namsaraev et al. |
| 2010/0210475 | A1 | 8/2010 | Lee et al. |
| 2010/0227329 | A1 | 9/2010 | Cuppens |
| 2010/0273219 | A1 | 10/2010 | May et al. |
| 2011/0028685 | A1 | 2/2011 | Purkayastha et al. |
| 2011/0031123 | A1 | 2/2011 | Schulze et al. |
| 2011/0033854 | A1 | 2/2011 | Drmanac et al. |
| 2011/0045462 | A1 | 2/2011 | Fu et al. |
| 2011/0059436 | A1 | 3/2011 | Hardin et al. |
| 2011/0111409 | A1 | 5/2011 | Sinicropi et al. |
| 2011/0152111 | A1 | 6/2011 | Fan et al. |
| 2011/0237449 | A1 | 9/2011 | McMaster et al. |
| 2011/0245101 | A1 | 10/2011 | Chee et al. |
| 2011/0245111 | A1 | 10/2011 | Chee |
| 2011/0287435 | A1 | 11/2011 | Grunenwald et al. |
| 2012/0021930 | A1 | 1/2012 | Schoen et al. |
| 2012/0046175 | A1 | 2/2012 | Rodesch et al. |
| 2012/0046178 | A1 | 2/2012 | Van Den Boom et al. |
| 2012/0065081 | A1 | 3/2012 | Chee |
| 2012/0135871 | A1 | 5/2012 | van Eijk et al. |
| 2012/0202698 | A1 | 8/2012 | van Eijk et al. |
| 2012/0202704 | A1 | 8/2012 | Fan et al. |
| 2012/0220479 | A1 | 8/2012 | Ericsson et al. |
| 2012/0245053 | A1 | 9/2012 | Shirai et al. |
| 2012/0252702 | A1 | 10/2012 | Muratani et al. |
| 2012/0258871 | A1 | 10/2012 | Kozlov et al. |
| 2012/0289414 | A1 | 11/2012 | Mitra et al. |
| 2012/0301925 | A1 | 11/2012 | Belyaev |
| 2013/0005594 | A1 | 1/2013 | Terbrueggen et al. |
| 2013/0005600 | A1 | 1/2013 | Olek |
| 2013/0023433 | A1 | 1/2013 | Luo et al. |
| 2013/0035239 | A1 | 2/2013 | Kong et al. |
| 2013/0040842 | A1 | 2/2013 | Lim et al. |
| 2013/0065768 | A1 | 3/2013 | Zheng et al. |
| 2013/0079232 | A1 | 3/2013 | Kain et al. |
| 2013/0171621 | A1 | 7/2013 | Luo et al. |
| 2013/0244884 | A1 | 9/2013 | Jacobson et al. |
| 2013/0261019 | A1 | 10/2013 | Lin et al. |
| 2013/0302801 | A1 | 11/2013 | Asbury et al. |
| 2013/0338042 | A1 | 12/2013 | Shen et al. |
| 2014/0066318 | A1 | 3/2014 | Frisen et al. |
| 2014/0121118 | A1 | 5/2014 | Warner |
| 2014/0270435 | A1 | 9/2014 | Dunn |
| 2014/0274731 | A1 | 9/2014 | Raymond et al. |
| 2014/0323330 | A1 | 10/2014 | Glezer et al. |
| 2014/0342921 | A1 | 11/2014 | Weiner |
| 2014/0378350 | A1 | 12/2014 | Hindson et al. |
| 2015/0000854 | A1 | 1/2015 | Gann-Fetter et al. |
| 2015/0292988 | A1 | 10/2015 | Bharadwaj et al. |
| 2015/0344942 | A1 | 12/2015 | Frisen et al. |
| 2016/0019337 | A1 | 1/2016 | Roberts et al. |
| 2016/0024576 | A1 | 1/2016 | Chee |
| 2016/0041159 | A1 | 2/2016 | Labaer et al. |
| 2016/0060687 | A1 | 3/2016 | Zhu et al. |
| 2016/0108458 | A1 | 4/2016 | Frei et al. |
| 2016/0122817 | A1 | 5/2016 | Jarosz et al. |
| 2016/0138091 | A1 | 5/2016 | Chee et al. |
| 2016/0145677 | A1 | 5/2016 | Chee et al. |
| 2016/0194692 | A1 | 7/2016 | Gore et al. |
| 2016/0201125 | A1 | 7/2016 | Samuels et al. |
| 2016/0253584 | A1 | 9/2016 | Fodor et al. |
| 2016/0289740 | A1 | 10/2016 | Fu et al. |
| 2016/0298180 | A1 | 10/2016 | Chee |
| 2016/0305856 | A1 | 10/2016 | Boyden et al. |
| 2016/0312276 | A1 | 10/2016 | Fu et al. |
| 2016/0333403 | A1 | 11/2016 | Chee |
| 2016/0376642 | A1 | 12/2016 | Landegren et al. |
| 2017/0009278 | A1 | 1/2017 | Söderberg et al. |
| 2017/0016053 | A1 | 1/2017 | Beechem et al. |
| 2017/0029875 | A1 | 2/2017 | Zhang et al. |
| 2017/0058339 | A1 | 3/2017 | Chee |
| 2017/0058340 | A1 | 3/2017 | Chee |
| 2017/0058345 | A1 | 3/2017 | Chee |
| 2017/0067096 | A1 | 3/2017 | Wassie et al. |
| 2017/0088881 | A1 | 3/2017 | Chee |
| 2017/0089811 | A1 | 3/2017 | Tillberg et al. |
| 2017/0159109 | A1 | 6/2017 | Zheng et al. |
| 2017/0166962 | A1 | 6/2017 | van Eijk et al. |
| 2017/0220733 | A1 | 8/2017 | Zhuang et al. |
| 2017/0233722 | A1 | 8/2017 | Seelig et al. |
| 2017/0241911 | A1 | 8/2017 | Rockel et al. |
| 2017/0283860 | A1 | 10/2017 | Kool et al. |
| 2017/0335297 | A1 | 11/2017 | Ha et al. |
| 2017/0335410 | A1 | 11/2017 | Driscoll et al. |
| 2017/0342405 | A1 | 11/2017 | Fu et al. |

(56) References Cited

U.S. PATENT DOCUMENTS

| | | | |
|---|---|---|---|
| 2017/0349940 | A1 | 12/2017 | Morin et al. |
| 2018/0051322 | A1 | 2/2018 | Church et al. |
| 2018/0057873 | A1 | 3/2018 | Zhou et al. |
| 2018/0080019 | A1 | 3/2018 | Blainey et al. |
| 2018/0088112 | A1 | 3/2018 | Fan et al. |
| 2018/0094316 | A1 | 4/2018 | Oliphant et al. |
| 2018/0112261 | A1 | 4/2018 | Van Driel et al. |
| 2018/0127817 | A1 | 5/2018 | Borchert et al. |
| 2018/0156784 | A1 | 6/2018 | Usmani et al. |
| 2018/0163265 | A1 | 6/2018 | Zhang et al. |
| 2018/0179591 | A1 | 6/2018 | van Eijk |
| 2018/0201925 | A1 | 7/2018 | Steemers et al. |
| 2018/0201980 | A1 | 7/2018 | Chee et al. |
| 2018/0208967 | A1 | 7/2018 | Larman et al. |
| 2018/0216161 | A1 | 8/2018 | Chen et al. |
| 2018/0216162 | A1 | 8/2018 | Belhocine et al. |
| 2018/0237864 | A1 | 8/2018 | Imler et al. |
| 2018/0245142 | A1 | 8/2018 | So et al. |
| 2018/0247017 | A1 | 8/2018 | van Eijk et al. |
| 2018/0291427 | A1 | 10/2018 | Edelman |
| 2018/0291439 | A1 | 10/2018 | van Eijk et al. |
| 2018/0305681 | A1 | 10/2018 | Jovanovich et al. |
| 2018/0312822 | A1 | 11/2018 | Lee et al. |
| 2018/0320226 | A1 | 11/2018 | Church et al. |
| 2018/0334670 | A1 | 11/2018 | Bharadwaj et al. |
| 2019/0055594 | A1 | 2/2019 | Samusik et al. |
| 2019/0064173 | A1 | 2/2019 | Bharadwaj et al. |
| 2019/0071656 | A1 | 3/2019 | Chang et al. |
| 2019/0085383 | A1 | 3/2019 | Church et al. |
| 2019/0119735 | A1 | 4/2019 | Deisseroth et al. |
| 2019/0135774 | A1 | 5/2019 | Orbai |
| 2019/0145982 | A1 | 5/2019 | Chee et al. |
| 2019/0161796 | A1 | 5/2019 | Hauling et al. |
| 2019/0177777 | A1 | 6/2019 | Chee |
| 2019/0177778 | A1 | 6/2019 | Chee |
| 2019/0177789 | A1 | 6/2019 | Hindson et al. |
| 2019/0177800 | A1 | 6/2019 | Boutet et al. |
| 2019/0194709 | A1 | 6/2019 | Church et al. |
| 2019/0203275 | A1 | 7/2019 | Frisen et al. |
| 2019/0218276 | A1 | 7/2019 | Regev et al. |
| 2019/0218608 | A1 | 7/2019 | Daugharthy et al. |
| 2019/0233878 | A1 | 8/2019 | Delaney et al. |
| 2019/0233880 | A1 | 8/2019 | Mir |
| 2019/0249226 | A1 | 8/2019 | Bent et al. |
| 2019/0262831 | A1 | 8/2019 | West et al. |
| 2019/0264268 | A1 | 8/2019 | Frisen et al. |
| 2019/0271028 | A1 | 9/2019 | Khafizov et al. |
| 2019/0271030 | A1 | 9/2019 | Chee |
| 2019/0271031 | A1 | 9/2019 | Chee |
| 2019/0300943 | A1 | 10/2019 | Chee et al. |
| 2019/0300944 | A1 | 10/2019 | Chee et al. |
| 2019/0300945 | A1 | 10/2019 | Chee et al. |
| 2019/0309353 | A1 | 10/2019 | Chee |
| 2019/0309354 | A1 | 10/2019 | Chee |
| 2019/0309355 | A1 | 10/2019 | Chee |
| 2019/0323071 | A1 | 10/2019 | Chee |
| 2019/0323088 | A1 | 10/2019 | Boutet et al. |
| 2019/0330617 | A1 | 10/2019 | Church et al. |
| 2019/0338353 | A1 | 11/2019 | Belgrader et al. |
| 2019/0360034 | A1 | 11/2019 | Zhou et al. |
| 2019/0360043 | A1 | 11/2019 | Pham et al. |
| 2019/0367969 | A1 | 12/2019 | Belhocine et al. |
| 2019/0367982 | A1 | 12/2019 | Belhocine et al. |
| 2019/0367997 | A1 | 12/2019 | Bent et al. |
| 2020/0002763 | A1 | 1/2020 | Belgrader et al. |
| 2020/0010891 | A1 | 1/2020 | Beechem et al. |
| 2020/0024641 | A1 | 1/2020 | Nolan et al. |
| 2020/0047010 | A1 | 2/2020 | Lee et al. |
| 2020/0048690 | A1 | 2/2020 | Chee |
| 2020/0053655 | A1 | 2/2020 | Ghosh et al. |
| 2020/0061064 | A1 | 2/2020 | Maciejewski et al. |
| 2020/0063191 | A1 | 2/2020 | Kennedy-Darling et al. |
| 2020/0063195 | A1 | 2/2020 | Chee |
| 2020/0063196 | A1 | 2/2020 | Chee |
| 2020/0071751 | A1 | 3/2020 | Daugharthy et al. |
| 2020/0080136 | A1 | 3/2020 | Zhang et al. |
| 2020/0109443 | A1 | 4/2020 | Chee |
| 2020/0123597 | A1 | 4/2020 | Daniel |
| 2020/0131570 | A1 | 4/2020 | Berti et al. |
| 2020/0140920 | A1 | 5/2020 | Pierce et al. |
| 2020/0173985 | A1 | 6/2020 | Dong et al. |
| 2020/0199565 | A1 | 6/2020 | Chen et al. |
| 2020/0199572 | A1 | 6/2020 | Kuersten et al. |
| 2020/0224244 | A1 | 7/2020 | Nilsson et al. |
| 2020/0239874 | A1 | 7/2020 | Mikkelsen |
| 2020/0239946 | A1 | 7/2020 | Dewal |
| 2020/0256867 | A1 | 8/2020 | Hennek et al. |
| 2020/0277663 | A1 | 9/2020 | Iyer |
| 2020/0277664 | A1 | 9/2020 | Frenz |
| 2020/0283852 | A1 | 9/2020 | Oliphant et al. |
| 2020/0299757 | A1 | 9/2020 | Chee et al. |
| 2020/0325531 | A1 | 10/2020 | Chee |
| 2020/0362398 | A1 | 11/2020 | Kishi et al. |
| 2020/0370095 | A1 | 11/2020 | Farmer et al. |
| 2020/0399687 | A1 | 12/2020 | Frisen et al. |
| 2020/0407781 | A1 | 12/2020 | Schnall-Levin |
| 2021/0010068 | A1 | 1/2021 | Chee et al. |
| 2021/0010070 | A1 | 1/2021 | Schnall-Levin et al. |
| 2021/0017587 | A1 | 1/2021 | Cai et al. |
| 2021/0095331 | A1 | 4/2021 | Fan et al. |
| 2021/0115504 | A1 | 4/2021 | Cai et al. |
| 2021/0123040 | A1 | 4/2021 | Macosko et al. |
| 2021/0130881 | A1 | 5/2021 | Cox |
| 2021/0140982 | A1 | 5/2021 | Uytingco et al. |
| 2021/0150707 | A1 | 5/2021 | Weisenfeld et al. |
| 2021/0155982 | A1 | 5/2021 | Yin et al. |
| 2021/0158522 | A1 | 5/2021 | Weisenfeld et al. |
| 2021/0172007 | A1 | 6/2021 | Chee et al. |
| 2021/0189475 | A1 | 6/2021 | Tentori et al. |
| 2021/0190770 | A1 | 6/2021 | Delaney et al. |
| 2021/0198741 | A1 | 7/2021 | Williams |
| 2021/0199660 | A1 | 7/2021 | Williams et al. |
| 2021/0207202 | A1 | 7/2021 | Chee |
| 2021/0214785 | A1 | 7/2021 | Stoeckius |
| 2021/0222235 | A1 | 7/2021 | Chee |
| 2021/0222241 | A1 | 7/2021 | Bharadwaj |
| 2021/0222242 | A1 | 7/2021 | Ramachandran Iyer |
| 2021/0222253 | A1 | 7/2021 | Uytingco |
| 2021/0223227 | A1 | 7/2021 | Stoeckius |
| 2021/0230584 | A1 | 7/2021 | Mikkelsen et al. |
| 2021/0230681 | A1 | 7/2021 | Patterson et al. |
| 2021/0230692 | A1 | 7/2021 | Daugharthy et al. |
| 2021/0237022 | A1 | 8/2021 | Bava |
| 2021/0238581 | A1 | 8/2021 | Mikkelsen et al. |
| 2021/0238664 | A1 | 8/2021 | Bava et al. |
| 2021/0238675 | A1 | 8/2021 | Bava |
| 2021/0238680 | A1 | 8/2021 | Bava |
| 2021/0247316 | A1 | 8/2021 | Bava |
| 2021/0255175 | A1 | 8/2021 | Chee et al. |
| 2021/0262018 | A1 | 8/2021 | Bava et al. |
| 2021/0262019 | A1 | 8/2021 | Alvarado Martinez et al. |
| 2021/0269864 | A1 | 9/2021 | Chee |
| 2021/0270822 | A1 | 9/2021 | Chee |
| 2021/0277460 | A1 | 9/2021 | Bava |
| 2021/0285036 | A1 | 9/2021 | Yin et al. |
| 2021/0285046 | A1 | 9/2021 | Chell et al. |
| 2021/0292748 | A1 | 9/2021 | Frisen et al. |
| 2021/0292822 | A1 | 9/2021 | Frisen et al. |
| 2021/0317510 | A1 | 10/2021 | Chee et al. |
| 2021/0317524 | A1 | 10/2021 | Lucero et al. |
| 2021/0324457 | A1 | 10/2021 | Ramachandran Iyer et al. |
| 2021/0332424 | A1 | 10/2021 | Schnall-Levin |
| 2021/0332425 | A1 | 10/2021 | Pfeiffer et al. |
| 2021/0348221 | A1 | 11/2021 | Chell et al. |
| 2022/0002791 | A1 | 1/2022 | Frisen et al. |
| 2022/0003755 | A1 | 1/2022 | Chee |
| 2022/0010367 | A1 | 1/2022 | Ramachandran Iyer et al. |
| 2022/0017951 | A1 | 1/2022 | Ramachandran Iyer et al. |
| 2022/0025446 | A1 | 1/2022 | Shah |
| 2022/0025447 | A1 | 1/2022 | Tentori et al. |
| 2022/0033888 | A1 | 2/2022 | Schnall-Levin et al. |
| 2022/0049293 | A1 | 2/2022 | Frenz et al. |
| 2022/0064630 | A1 | 3/2022 | Bent et al. |
| 2022/0081728 | A1 | 3/2022 | Williams |

(56) References Cited

U.S. PATENT DOCUMENTS

| | | | |
|---|---|---|---|
| 2022/0090058 | A1 | 3/2022 | Frisen et al. |
| 2022/0090175 | A1 | 3/2022 | Uytingco et al. |
| 2022/0090181 | A1 | 3/2022 | Gallant et al. |
| 2022/0098576 | A1 | 3/2022 | Dadhwal |
| 2022/0098661 | A1 | 3/2022 | Chew et al. |
| 2022/0106632 | A1 | 4/2022 | Galonska et al. |
| 2022/0106633 | A1 | 4/2022 | Engblom et al. |
| 2022/0112486 | A1 | 4/2022 | Ramachandran Iyer et al. |
| 2022/0112545 | A1 | 4/2022 | Chee |
| 2022/0119869 | A1 | 4/2022 | Ramachandran Iyer et al. |
| 2022/0127659 | A1 | 4/2022 | Frisen et al. |
| 2022/0127666 | A1 | 4/2022 | Katiraee et al. |
| 2022/0127672 | A1 | 4/2022 | Stoeckius |
| 2022/0145361 | A1 | 5/2022 | Frenz et al. |
| 2022/0154255 | A1 | 5/2022 | Chee et al. |
| 2022/0170083 | A1 | 6/2022 | Khaled et al. |
| 2022/0195422 | A1 | 6/2022 | Gallant et al. |
| 2022/0195505 | A1 | 6/2022 | Frisen et al. |
| 2022/0196644 | A1 | 6/2022 | Chee |
| 2022/0213526 | A1 | 7/2022 | Frisen et al. |
| 2022/0220544 | A1 | 7/2022 | Ach et al. |
| 2022/0241780 | A1 | 8/2022 | Tentori et al. |
| 2022/0267844 | A1 | 8/2022 | Ramachandran Iyer et al. |
| 2022/0282329 | A1 | 9/2022 | Chell et al. |
| 2022/0290217 | A1 | 9/2022 | Frenz et al. |
| 2022/0290219 | A1 | 9/2022 | Chee |
| 2022/0298560 | A1 | 9/2022 | Frisen et al. |
| 2022/0325325 | A1 | 10/2022 | Chee et al. |
| 2022/0326251 | A1 | 10/2022 | Uytingco et al. |
| 2022/0333171 | A1 | 10/2022 | Chee |
| 2022/0333191 | A1 | 10/2022 | Mikkelsen et al. |
| 2022/0333192 | A1 | 10/2022 | Uytingco |
| 2022/0333195 | A1 | 10/2022 | Schnall-Levin et al. |
| 2022/0334031 | A1 | 10/2022 | Delaney et al. |
| 2022/0348905 | A1 | 11/2022 | Dadhwal |
| 2022/0348992 | A1 | 11/2022 | Stoeckius et al. |
| 2022/0356464 | A1 | 11/2022 | Kim et al. |
| 2022/0364163 | A1 | 11/2022 | Stahl et al. |
| 2022/0389491 | A1 | 12/2022 | Chee |
| 2022/0389503 | A1 | 12/2022 | Mikkelsen et al. |
| 2022/0389504 | A1 | 12/2022 | Chew et al. |
| 2022/0403455 | A1 | 12/2022 | Ramachandran Iyer et al. |
| 2022/0404245 | A1 | 12/2022 | Chell et al. |
| 2023/0002812 | A1 | 1/2023 | Stoeckius et al. |
| 2023/0014008 | A1 | 1/2023 | Shastry |
| 2023/0017773 | A1 | 1/2023 | Kim et al. |
| 2023/0031305 | A1 | 2/2023 | Hernandez Neuta et al. |
| 2023/0033960 | A1 | 2/2023 | Gallant et al. |
| 2023/0034039 | A1 | 2/2023 | Shahjamali |
| 2023/0034216 | A1 | 2/2023 | Bava |
| 2023/0040363 | A1 | 2/2023 | Chee |
| 2023/0042088 | A1 | 2/2023 | Chee |
| 2023/0042817 | A1 | 2/2023 | Mignardi |
| 2023/0047782 | A1 | 2/2023 | Tentori et al. |
| 2023/0056549 | A1 | 2/2023 | Dadhwal |
| 2023/0064372 | A1 | 3/2023 | Chell et al. |
| 2023/0069046 | A1 | 3/2023 | Chew et al. |
| 2023/0077364 | A1 | 3/2023 | Patterson et al. |
| 2023/0080543 | A1 | 3/2023 | Katiraee et al. |
| 2023/0081381 | A1 | 3/2023 | Chew et al. |
| 2023/0100497 | A1 | 3/2023 | Frisen et al. |
| 2023/0107023 | A1 | 4/2023 | Chee |
| 2023/0111225 | A1 | 4/2023 | Chew et al. |
| 2023/0113230 | A1 | 4/2023 | Kim et al. |
| 2023/0126825 | A1 | 4/2023 | Nagendran et al. |
| 2023/0129552 | A1 | 4/2023 | Ramachandran Iyer |
| 2023/0135010 | A1 | 5/2023 | Tentori et al. |
| 2023/0143569 | A1 | 5/2023 | Iyer et al. |
| 2023/0145575 | A1 | 5/2023 | Gallant et al. |
| 2023/0147726 | A1 | 5/2023 | Hadrup et al. |
| 2023/0151412 | A1 | 5/2023 | Chee |
| 2023/0159994 | A1 | 5/2023 | Chee |
| 2023/0159995 | A1 | 5/2023 | Iyer et al. |
| 2023/0160008 | A1 | 5/2023 | Chell et al. |
| 2023/0175045 | A1 | 6/2023 | Katsori et al. |
| 2023/0183684 | A1 | 6/2023 | Gallant et al. |
| 2023/0183785 | A1 | 6/2023 | Frisen et al. |
| 2023/0194469 | A1 | 6/2023 | Tentori et al. |
| 2023/0194470 | A1 | 6/2023 | Kim et al. |
| 2023/0203478 | A1 | 6/2023 | Kim et al. |
| 2023/0212650 | A1 | 7/2023 | Chew et al. |
| 2023/0212655 | A1 | 7/2023 | Chee |
| 2023/0212656 | A1 | 7/2023 | Chow et al. |
| 2023/0220368 | A1 | 7/2023 | Kim |
| 2023/0220454 | A1 | 7/2023 | Bent et al. |
| 2023/0220455 | A1 | 7/2023 | Galonska et al. |
| 2023/0227811 | A1 | 7/2023 | Dadhwal |
| 2023/0228762 | A1 | 7/2023 | Uytingco et al. |
| 2023/0242973 | A1 | 8/2023 | Frisen et al. |
| 2023/0242976 | A1 | 8/2023 | Tentori et al. |
| 2023/0265488 | A1 | 8/2023 | Gohil et al. |
| 2023/0265489 | A1 | 8/2023 | Uytingco et al. |
| 2023/0265491 | A1 | 8/2023 | Tentori et al. |
| 2023/0267625 | A1 | 8/2023 | Tentori et al. |
| 2023/0279474 | A1 | 9/2023 | Katiraee |
| 2023/0279477 | A1 | 9/2023 | Kvastad et al. |
| 2023/0279481 | A1 | 9/2023 | Marrache et al. |
| 2023/0287399 | A1 | 9/2023 | Gallant et al. |
| 2023/0287475 | A1 | 9/2023 | Chell et al. |
| 2023/0287481 | A1 | 9/2023 | Katsori et al. |
| 2023/0295699 | A1 | 9/2023 | Sukovich et al. |
| 2023/0295722 | A1 | 9/2023 | Bharadwaj |
| 2023/0304072 | A1 | 9/2023 | Gohil et al. |
| 2023/0304074 | A1 | 9/2023 | Chee et al. |
| 2023/0304078 | A1 | 9/2023 | Frisen et al. |
| 2023/0313279 | A1 | 10/2023 | Giacomello et al. |
| 2023/0323340 | A1 | 10/2023 | Dadhwal |
| 2023/0323434 | A1 | 10/2023 | Yin et al. |
| 2023/0323436 | A1 | 10/2023 | Chee |
| 2023/0323447 | A1 | 10/2023 | Schnall-Levin et al. |
| 2023/0323453 | A1 | 10/2023 | Stoeckius |
| 2023/0332138 | A1 | 10/2023 | Kim et al. |
| 2023/0332211 | A1 | 10/2023 | Chee |
| 2023/0332212 | A1 | 10/2023 | Chew et al. |
| 2023/0332227 | A1 | 10/2023 | Ramachandran Iyer |
| 2023/0332247 | A1 | 10/2023 | Singh et al. |
| 2023/0351619 | A1 | 11/2023 | Tentori et al. |
| 2023/0358733 | A1 | 11/2023 | Chee |
| 2023/0366008 | A1 | 11/2023 | Chew et al. |
| 2023/0383285 | A1 | 11/2023 | Kim et al. |
| 2023/0383344 | A1 | 11/2023 | Stoeckius |
| 2023/0392204 | A1 | 12/2023 | Chell et al. |
| 2023/0393071 | A1 | 12/2023 | Bava |
| 2023/0407404 | A1 | 12/2023 | Baumgartner et al. |
| 2023/0416807 | A1 | 12/2023 | Chee |
| 2023/0416808 | A1 | 12/2023 | Sukovich et al. |
| 2023/0416850 | A1 | 12/2023 | Singh et al. |
| 2024/0002931 | A1 | 1/2024 | Bava |
| 2024/0011081 | A1 | 1/2024 | Chee |
| 2024/0011090 | A1 | 1/2024 | Chew et al. |
| 2024/0018572 | A1 | 1/2024 | Mignardi |
| 2024/0018575 | A1 | 1/2024 | Gallant et al. |
| 2024/0018589 | A1 | 1/2024 | Schnall-Levin et al. |
| 2024/0026445 | A1 | 1/2024 | Ramachandran Iyer et al. |
| 2024/0033743 | A1 | 2/2024 | Tentori et al. |
| 2024/0035937 | A1 | 2/2024 | Cox et al. |
| 2024/0043908 | A1 | 2/2024 | Chew et al. |
| 2024/0043925 | A1 | 2/2024 | Bent et al. |
| 2024/0052343 | A1 | 2/2024 | Gallant et al. |
| 2024/0053351 | A1 | 2/2024 | Uytingco et al. |
| 2024/0060115 | A1 | 2/2024 | Chee et al. |
| 2024/0067953 | A1 | 2/2024 | Mikkelsen et al. |
| 2024/0068016 | A1 | 2/2024 | Frisen et al. |
| 2024/0068017 | A1 | 2/2024 | Lundeberg et al. |
| 2024/0076723 | A1 | 3/2024 | Mignardi |
| 2024/0080346 | A1 | 3/2024 | Engblom et al. |
| 2024/0084365 | A1 | 3/2024 | Frisen et al. |
| 2024/0084366 | A1 | 3/2024 | Chee |
| 2024/0084383 | A1 | 3/2024 | Ramachandran Iyer et al. |
| 2024/0093274 | A1 | 3/2024 | Frisen et al. |
| 2024/0093290 | A1 | 3/2024 | Stahl et al. |
| 2024/0110228 | A1 | 4/2024 | Uytingco et al. |
| 2024/0124933 | A1 | 4/2024 | Chell et al. |
| 2024/0125772 | A1 | 4/2024 | Delaney et al. |

(56) References Cited

U.S. PATENT DOCUMENTS

| | | | |
|---|---|---|---|
| 2024/0141327 | A1 | 5/2024 | Kim et al. |
| 2024/0158838 | A1 | 5/2024 | Alvarado Martinez et al. |
| 2024/0175080 | A1 | 5/2024 | Galonska et al. |
| 2024/0182968 | A1 | 6/2024 | Bava |
| 2024/0191286 | A1 | 6/2024 | Boutet et al. |
| 2024/0200121 | A1 | 6/2024 | Boutet |
| 2024/0209425 | A1 | 6/2024 | Yin et al. |
| 2024/0218427 | A1 | 7/2024 | Sukovich et al. |
| 2024/0218432 | A1 | 7/2024 | Mielinis |
| 2024/0219701 | A1 | 7/2024 | Tentori et al. |
| 2024/0253036 | A1 | 8/2024 | Kim et al. |
| 2024/0263218 | A1 | 8/2024 | Katiraee et al. |
| 2024/0271190 | A1 | 8/2024 | Stoeckius et al. |
| 2024/0271195 | A1 | 8/2024 | Mikhaiel et al. |
| 2024/0279747 | A1 | 8/2024 | Williams |
| 2024/0287600 | A1 | 8/2024 | Iyer et al. |
| 2024/0294971 | A1 | 9/2024 | Galonska |
| 2024/0294974 | A1 | 9/2024 | Galonska et al. |
| 2024/0294975 | A1 | 9/2024 | Lin et al. |
| 2024/0301488 | A1 | 9/2024 | Stoeckius |
| 2024/0301489 | A1 | 9/2024 | Chew et al. |
| 2024/0360494 | A1 | 10/2024 | Costa et al. |
| 2024/0368711 | A1 | 11/2024 | Giacomello et al. |
| 2024/0377297 | A1 | 11/2024 | Cox et al. |
| 2024/0385088 | A1 | 11/2024 | Kim et al. |
| 2024/0392349 | A1 | 11/2024 | Frisen et al. |
| 2024/0392351 | A1 | 11/2024 | Chee |
| 2024/0392352 | A1 | 11/2024 | Stahl et al. |
| 2024/0392353 | A1 | 11/2024 | Engblom et al. |
| 2024/0401109 | A1 | 12/2024 | Kim et al. |
| 2024/0401117 | A1 | 12/2024 | Bava |
| 2024/0401118 | A1 | 12/2024 | Tentori et al. |
| 2024/0404301 | A1 | 12/2024 | Li et al. |
| 2024/0408593 | A1 | 12/2024 | Kim et al. |
| 2024/0416315 | A1 | 12/2024 | Bava |
| 2024/0417783 | A1 | 12/2024 | Chew et al. |
| 2024/0417784 | A1 | 12/2024 | Sukovich et al. |
| 2025/0002980 | A1 | 1/2025 | Tentori et al. |
| 2025/0002982 | A1 | 1/2025 | Stoeckius et al. |
| 2025/0003956 | A1 | 1/2025 | Delaney et al. |
| 2025/0019689 | A1 | 1/2025 | Galonska et al. |
| 2025/0019749 | A1 | 1/2025 | Katiraee et al. |
| 2025/0066762 | A1 | 2/2025 | Man et al. |
| 2025/0066770 | A1 | 2/2025 | Costa |
| 2025/0073719 | A1 | 3/2025 | Cox et al. |
| 2025/0075261 | A1 | 3/2025 | Kim |
| 2025/0101501 | A1 | 3/2025 | Chee |
| 2025/0101502 | A1 | 3/2025 | Chee |
| 2025/0101504 | A1 | 3/2025 | Nagendran et al. |
| 2025/0122564 | A1 | 4/2025 | Mignardi et al. |
| 2025/0122565 | A1 | 4/2025 | Schnall-Levin et al. |
| 2025/0129412 | A1 | 4/2025 | Uytingco et al. |
| 2025/0129421 | A1 | 4/2025 | Schnall-Levin et al. |
| 2025/0137043 | A1 | 5/2025 | Tentori |
| 2025/0145984 | A1 | 5/2025 | Ma et al. |
| 2025/0146057 | A1 | 5/2025 | Schnall-Levin et al. |
| 2025/0146058 | A1 | 5/2025 | Tentori |
| 2025/0146071 | A1 | 5/2025 | Schnall-Levin et al. |
| 2025/0146072 | A1 | 5/2025 | Schnall-Levin et al. |
| 2025/0154565 | A1 | 5/2025 | Chee |
| 2025/0154566 | A1 | 5/2025 | Chee |
| 2025/0154567 | A1 | 5/2025 | Chee |
| 2025/0154568 | A1 | 5/2025 | Frisen et al. |
| 2025/0154569 | A1 | 5/2025 | Stoeckius et al. |
| 2025/0154571 | A1 | 5/2025 | Ramachandran Iyer et al. |
| 2025/0154588 | A1 | 5/2025 | Ramachandran Iyer et al. |
| 2025/0155446 | A1 | 5/2025 | Uytingco et al. |
| 2025/0163501 | A1 | 5/2025 | Singh et al. |
| 2025/0163509 | A1 | 5/2025 | Daugharthy et al. |
| 2025/0171833 | A1 | 5/2025 | Frisen et al. |
| 2025/0171848 | A1 | 5/2025 | Chell et al. |
| 2025/0179475 | A1 | 6/2025 | Borgstrom et al. |
| 2025/0182305 | A1 | 6/2025 | Tentori et al. |
| 2025/0182503 | A1 | 6/2025 | Li et al. |
| 2025/0188526 | A1 | 6/2025 | Sukovich et al. |
| 2025/0189483 | A1 | 6/2025 | Kim et al. |
| 2025/0197847 | A1 | 6/2025 | Kim et al. |
| 2025/0197938 | A1 | 6/2025 | Bjorninen |
| 2025/0207125 | A1 | 6/2025 | Gupta et al. |
| 2025/0207182 | A1 | 6/2025 | Chee |
| 2025/0207183 | A1 | 6/2025 | Chee |
| 2025/0207195 | A1 | 6/2025 | Chell et al. |
| 2025/0208115 | A1 | 6/2025 | Bent |
| 2025/0215482 | A1 | 7/2025 | Mignardi et al. |
| 2025/0215484 | A1 | 7/2025 | Ramachandran Iyer et al. |
| 2025/0216300 | A1 | 7/2025 | Delaney et al. |
| 2025/0216303 | A1 | 7/2025 | Cox et al. |
| 2025/0223633 | A1 | 7/2025 | Frenz et al. |
| 2025/0230487 | A1 | 7/2025 | Chee et al. |
| 2025/0230498 | A1 | 7/2025 | Katiraee |
| 2025/0250621 | A1 | 8/2025 | Galonska et al. |
| 2025/0250632 | A1 | 8/2025 | Mignardi et al. |
| 2025/0257393 | A1 | 8/2025 | Katiraee et al. |
| 2025/0263791 | A1 | 8/2025 | Bava |
| 2025/0264411 | A1 | 8/2025 | Bava |
| 2025/0283154 | A1 | 9/2025 | Iyer et al. |
| 2025/0283157 | A1 | 9/2025 | Uytingco et al. |
| 2025/0297308 | A1 | 9/2025 | Tentori |
| 2025/0313890 | A1 | 10/2025 | Lundeberg et al. |
| 2025/0313892 | A1 | 10/2025 | Stoeckius |
| 2025/0340932 | A1 | 11/2025 | Chee |
| 2025/0340933 | A1 | 11/2025 | Giacomello et al. |
| 2025/0354931 | A1 | 11/2025 | Shah et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 105925671 | 9/2016 |
| CN | 107849606 | 3/2018 |
| CN | 108949924 | 12/2018 |
| EP | 1782737 | 5/2007 |
| EP | 1910562 | 4/2008 |
| EP | 1923471 | 5/2008 |
| EP | 1929039 | 6/2008 |
| EP | 2002017 | 12/2008 |
| EP | 2130913 | 12/2009 |
| EP | 2292788 | 3/2011 |
| EP | 2302070 | 3/2011 |
| EP | 2580351 | 4/2013 |
| EP | 2881465 | 6/2015 |
| EP | 3013984 | 5/2016 |
| EP | 3207134 | 7/2019 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 2000/017390 | 3/2000 |
| WO | WO 2000/063437 | 10/2000 |
| WO | WO 2001/006012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |

(56) References Cited

FOREIGN PATENT DOCUMENTS

| | | |
|---|---|---|
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2006/137733 | 12/2006 |
| WO | WO 2007/037678 | 4/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/075086 | 6/2008 |
| WO | WO 2008/093098 | 8/2008 |
| WO | WO 2009/032167 | 3/2009 |
| WO | WO 2009/036525 | 3/2009 |
| WO | WO 2009/137521 | 11/2009 |
| WO | WO 2009/152928 | 12/2009 |
| WO | WO 2010/019826 | 2/2010 |
| WO | WO 2010/027870 | 3/2010 |
| WO | WO 2010/088517 | 8/2010 |
| WO | WO 2010/126614 | 11/2010 |
| WO | WO 2010/127186 | 11/2010 |
| WO | WO 2011/008502 | 1/2011 |
| WO | WO 2011/062933 | 5/2011 |
| WO | WO 2011/068088 | 6/2011 |
| WO | WO 2011/127006 | 10/2011 |
| WO | WO 2011/155833 | 12/2011 |
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/159089 | 11/2012 |
| WO | WO 2013/022807 | 2/2013 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/060483 | 4/2014 |
| WO | WO 2014/071361 | 5/2014 |
| WO | WO 2014/130576 | 8/2014 |
| WO | WO 2014/144713 | 9/2014 |
| WO | WO 2014/152397 | 9/2014 |
| WO | WO 2014/210223 | 12/2014 |
| WO | WO 2014/210353 | 12/2014 |
| WO | WO 2015/031691 | 3/2015 |
| WO | WO 2015/069374 | 5/2015 |
| WO | WO 2015/117163 | 8/2015 |
| WO | WO 2015/161173 | 10/2015 |
| WO | WO 2016/033251 | 3/2016 |
| WO | WO 2016/077763 | 5/2016 |
| WO | WO 2016/100196 | 6/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/044993 | 3/2017 |
| WO | WO 2017/075293 | 5/2017 |
| WO | WO 2017/096158 | 7/2017 |
| WO | WO 2017/143155 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/085599 | 5/2018 |
| WO | WO 2018/089550 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/175779 | 9/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047004 | 3/2020 |
| WO | WO 2020/047010 | 3/2020 |
| WO | WO 2020/056381 | 3/2020 |
| WO | WO 2020/061066 | 3/2020 |
| WO | WO 2020/061108 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |

(56) References Cited

FOREIGN PATENT DOCUMENTS

| | | |
|---|---|---|
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/247593 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/032195 | 2/2022 |
| WO | WO 2022/060798 | 3/2022 |
| WO | WO 2022/060953 | 3/2022 |
| WO | WO 2022/061150 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2011/019964 | 6/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/034739 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/130019 | 7/2023 |
| WO | WO 2023/147355 | 8/2023 |
| WO | WO 2023/150098 | 8/2023 |
| WO | WO 2023/150163 | 8/2023 |
| WO | WO 2023/150171 | 8/2023 |
| WO | WO 2023/150763 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |
| WO | WO 2024/220882 | 10/2024 |
| WO | WO 2024/238900 | 11/2024 |
| WO | WO 2024/254316 | 12/2024 |
| WO | WO 2025/029605 | 2/2025 |
| WO | WO 2025/029627 | 2/2025 |
| WO | WO 2025/043076 | 2/2025 |
| WO | WO 2025/072119 | 4/2025 |
| WO | WO 2025/090912 | 5/2025 |
| WO | WO 2025/096581 | 5/2025 |
| WO | WO 2025/101864 | 5/2025 |

OTHER PUBLICATIONS

Asp et al., "A spatiotemporal organ-wide gene expression and cell atlas of the developing human heart," Cell, Dec. 12, 2019, 179(7):1647-1660.

Kuhn et al., "A novel, high-performance random array platform for quantitative gene expression profiling," Genome Res, 2004, 14:2347-2356.

10xGenomics.com, [online], "Visium Spatial Gene Expression Reagent Kits—User Guide," Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.

U.S. Appl. No. 63/033,348, filed Jun. 2, 2020, Bent.

Arslan et al., "Engineering of a superhelicase through conformational control (Supplementary Materials)," Science, Apr. 17, 2015, 348(6232):344-347, 18 pages.

Arslan et al., "Engineering of a superhelicase through conformational control," Science, Apr. 17, 2015, 348(6232):344-347.

Baner et al., "Signal amplification of padlock probes by rolling circle replication," Nucleic Acids Res., 1998, 26(22):5073-5078.

Borm et al., "High throughput Human embryo spatial transcriptome mapping by surface transfer of tissue RNA," Abstracts Selected Talks, Single Cell Genomics mtg, (SCG2019), 2019, 1 pages (Abstract Only).

Chen et al., "Efficient in situ barcode sequencing using padlock probe-based BaristaSeq," Nucleic Acids Res., 2018, 46(4): e22, 11 pages.

Codeluppi et al., "Spatial organization of the somatosensory cortex revealed by osmFISH," Nature Methods, Nov. 2018, 15:932-935.

Dean et al., "Rapid Amplification of Plasmid and Phage DNA Using Phi29 DNA Polymerase and Multiply-Primed Rolling Circle Amplification," Genome Research, Jun. 2001, 11:1095-1099.

Eng et al., "Transcriptome-scale super-resolved imaging in tissues by RNA seqFISH+," Nature, Apr. 2019, 568(7751):235-239, 37 pages.

Faruqi et al., "High-throughput genotyping of single nucleotide polymorphisms with rolling circle amplification," BMC Genomics, Aug. 2001, 2:4, 10 pages.

Gao et al., "A highly homogeneous expansion microscopy polymer composed of tetrahedron-like monomers," bioRxiv, Oct. 22, 2019, 23 pages (Preprint).

Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.

Goh et al., "Highly Specific Multiplexed RNA Imaging In Tissues With Split-FISH," Nat Methods, Jun. 15, 2020, 17(7):689-693, 21 pages.

Goransson et al., "A single molecule array for digital targeted molecular analyses," Nucleic Acids Res., Nov. 25, 2009, 37(1):e7, 9 pages.

Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.

Liu et al., "High-Spatial-Resolution Multi-Omnics Sequencing via Deterministic Barcoding in Tissue," Cell, Nov. 13, 2020, 183(6):1665-1681, 36 pages.

Liu et al., "Spatial transcriptome sequencing of FFPE tissues at cellular level," bioRxiv 788992, Oct. 14, 2020, 39 pages.

Mignardi et al., "Oligonucleotide gap-fill ligation for mutation detection and sequencing in situ," Nucleic Acids Research, Aug. 3, 2015, 43(22):e151, 12 pages.

(56) References Cited

OTHER PUBLICATIONS

Mohsen et al., "The Discovery of Rolling Circle Amplification and Rolling Circle Transcription," Acc Chem Res., Nov. 15, 2016, 49(11):2540-2550, 25 pages.
Nallur et al., "Signal amplification by rolling circle amplification on DNA microarrays," Nucleic Acids Res., Dec. 1, 2001, 29(23):e118, 9 pages.
Raj et al., "Imaging individual mRNA molecules using multiple singly labeled probes," Nature Methods, Oct. 2008, 5(10):877-879, 9 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Takei et al., "Integrated Spatial Genomics Reveals Global Architecture of Single Nuclei," Nature, Jan. 27, 2021, 590(7845):344-350, 53 pages.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Ergin et al., "Proteomic Analysis of PAXgene-Fixed Tissues," J Proteome Res., 2010, 9(10):5188-96.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Appella, "Non-natural nucleic acids for synthetic biology," Current Opinion in Chemical Biology, Dec. 2009, 13(5-6): 687-696.
Bunt et al., "FRET from single to multiplexed signaling events," Biophys Rev. Apr. 2017, 9(2): 119-129.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Ma et al., "Isothermal amplification method for next-generation sequencing," PNAS, Aug. 12, 2013, 110(35):14320-14323.
Marx, "Method of the Year: spatially resolved transcriptomics," Nature Methods, 2021, 18(1):9-14.
Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
Stickels et al., "Highly sensitive spatial transcriptomics at near-cellular resolution with Slide-seqV2," Nat Biotechnol., Mar. 2021, 39(3):313-319, 28 pages (Author Manuscript).
U.S. Appl. No. 16/353,937, filed Mar. 14, 2019, Frisen et al.
U.S. Appl. No. 17/707,189, filed Mar. 29, 2022, Chell et al.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
[No Author Listed], "Proseek® Multiplex 96×96 User Manual," Olink Proteomics, Olink Bioscience, Uppsala, Sweden, 2017, 20 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwdI9It/e54d99fb08a8f1500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwdI9It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_ VisiumSpatialGeneExpression_UserGuide_RevD.pdf>, 70 pages.
Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Andresen et al., "Helicase-dependent amplification: use in OnChip amplification and potential for point-of-care diagnostics," Expert Rev Mol Diagn., Oct. 2009, 9(7):645-650.
Aran et al., "xCell: digitally portraying the tissue cellular heterogeneity landscape, " Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al, "2D-PCR: a method of mapping DNA in tissue sections," Lab Chip, 2009, 9(24):3526-34.
Asp et al., "Spatially Resolved Transcriptomes-Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.

(56) References Cited

OTHER PUBLICATIONS

Atkinson, "Overview of Translation: Lecture Manuscript," U of Texas, 2000, DD, pp. 6.1-6.8.
Bailey et al., "Comprehensive Characterization of Cancer Driver Genes and Mutations," Cell, Apr. 2018, 173(2):371-385, 38 pages.
Bains et al., "A novel method for nucleic acid sequence determination," Journal of Theoretical Biology, 1988, 135(3), 303-7.
Balakrishnan et al., "Flap endonuclease 1," Annu Rev Biochem., Jun. 2013, 82:119-138.
Barnes, "PCR amplification of up to 35-kb DNA with high fidelity and high yield from lambda bacteriophage templates," Proc. Natl. Acad. Sci USA, 1994, 91(6):2216-2220.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Behan et al., "Prioritization of cancer therapeutic targets using CRISPR-Cas9 screens," Nature, Apr. 2019, 568:511-516.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Birney et al., "Identification and analysis of functional elements in 1% of the human genome by the ENCODE pilot project," Nature, 2007, 447(7146):799-816.
Blair et al., "Microarray temperature optimization using hybridization kinetics, " Methods Mol Biol., 2009, 529:171-96.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolognesi et al., "Multiplex Staining by Sequential Immunostaining and Antibody Removal on Routine Tissue Sections," J. Histochem. Cytochem., Aug. 2017, 65(8):431-444.
Bolotin et al., "MiXCR: software for comprehensive adaptive immunity profiling," Nat Methods., May 2015, 12(5):380-1.
Boulé et al., "Terminal deoxynucleotidyl transferase indiscriminately incorporates ribonucleotides and deoxyribonucleotides," J Biol Chem., Aug. 2001, 276(33):31388-93.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections," Biotechniques, 1998, 24(1):92-100.
Caliari et al., "A practical guide to hydrogels for cell culture," Nat Methods., Apr. 2016, 13(5):405-14.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "DNA hybridization detection in a microfluidic Channel using two fluorescently labelled nucleic acid probes," Biosensors and Bioelectronics, 2008, 23(12):1878-1882.
Chen et al., "Expansion microscopy," Science, 2015, 347(6221):543-548.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "µCB-seq: microfluidic cell barcoding and sequencing for high-resolution imaging and sequencing of single cells," Lab Chip, Nov. 2020, 20(21):3899-3913.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Chrisey et al., "Covalent attachment of synthetic DNA to self-assembled monolayer films," Nucleic Acids Res., Aug. 1996, 24(15):3031-9.
Ciaccio et al., "Systems analysis of EGF receptor signaling dynamics with microwestern arrays," Nat Methods, Feb. 2010, 7(2):148-55.
Constantine et al., "Use of genechip high-density oligonucleotide arrays for gene expression monitoring," Life Science News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Cunningham et al., "Ensembl 2019," Nucleic Acids Research, Nov. 2018, 47(D1):D745-751.

(56) References Cited

OTHER PUBLICATIONS

Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase, " BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Evers et al., "The effect of formaldehyde fixation on RNA: optimization of formaldehyde adduct removal," J Mol Diagn., May 2011, 13(3):282-8.
Fang et al., "A genetics-led approach defines the drug target landscape of 30 immune-related traits," Nature Genetics, Jun. 2019, 51(7):1082-1091, 15 pages.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Flicek et al., "Ensembl 2014," Nucleic Acids Res., Jan. 2014, 42(Database issue):D749-D755.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fu et al., "Continuous Polony Gels for Tissue Mapping with High Resolution and RNA Capture Efficiency," bioRxiv, 2021, 20 pages.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gansauge et al., "Single-stranded DNA library preparation from highly degraded DNA using T4 DNA ligase," Nucleic Acids Res., Jun. 2017, 45(10):e79, 10 pages.
Gao et al., "Q&A: Expansion microscopy," BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "Excess dNTPs minimize RNA hydrolysis during reverse transcription," Biotechniques, Nov. 2002, 33(5):984, 986, 988, 990.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.

(56) References Cited

OTHER PUBLICATIONS

Harrow et al., "GENCODE: The reference human genome annotation for The ENCODE Project," Genome Res., Sep. 2012, 22(9):1760-1774.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount Arabidopsis samples," Nature Protocols, 2006, 1(4):1939-1946.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hoadley et al., "Cell-of-Origin Patterns Dominate the Molecular Classification of 10,000 Tumors from 33 Types of Cancer," Cell, Apr. 2018, 173(2):291-304, 21 pages.
Hoffman et al., "Formaldehyde crosslinking: a tool for the study of chromatin complexes," J Biol Chem., Oct. 2015, 290(44):26404-11.
Hsuih et al., "Novel, Ligation-Dependent PCR Assay for Detection of Hepatitis C Virus in Serum," Journal of Clinical Microbiology, Mar. 1996, 34(3):501-507.
Hu et al., "High reproducibility using sodium hydroxide-stripped long oligonucleotide DNA microarrays," Biotechniques, Jan. 2005, 38(1):121-4.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Illumina.com [online], "Ribo-ZeroR rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Kandoth et al., "Mutational landscape and significance across 12 major cancer types," Nature, Oct. 2013, 502(7471):333-339, 20 pages.
Kap et al., "Histological assessment of PAXgene tissue fixation and stabilization reagents," PLOS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Ke et al., "In situ sequencing for RNA analysis in preserved tissue and cells," Nat Methods., Sep. 2013, Supplementary Materials, 29 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.
Kozlov et al., "A highly scalable peptide-based assay system for proteomics," PLoS ONE, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by chlorella virus DNA ligase and a novel iLock assay with improved direct RNA detection accuracy," Nucleic Acids Research, Oct. 2017, 45(18):e161, 9 pages.
Kumar et al., "Template-directed oligonucleotide strand ligation, covalent intramolecular DNA circularization and catenation using click chemistry," J Am Chem Soc., May 2007, 129(21):6859-64.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lahiani et al., "Enabling Histopathological Annotations on Immunofluorescent Images through Virtualization of Hematoxylin and Eosin," J Pathol Inform., Feb. 2018, 9:1, 8 pages.
Lampe et al., "A purified mariner transposase is sufficient to mediate transposition in vitro," EMBO J., Oct. 1996, 15(19):5470-9.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Lee et al., "Improving the efficiency of genomic loci capture using oligonucleotide arrays for high throughput resequencing," BMC Genomics, Dec. 2009, 10:646, 12 pages.

(56) References Cited

OTHER PUBLICATIONS

Leriche et al., "Cleavable linkers in chemical biology," Bioorganic & Medicinal Chemistry, 2012, 20:571-582.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Lizardi et al., "Mutation detection and single-molecule counting using isothermal rolling-circle amplification," Nat. Genet., 1998, 19(3):225-232.
Lou et al., "A review of room temperature storage of biospecimen tissue and nucleic acids for anatomic pathology laboratories and biorepositories," Clin Biochem., Mar. 2014, 47(4-5):267-73.
Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus, " Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck et al., "Immunohistochemical markers for quantitative studies of neurons and glia in human neocortex," J Histochem Cytochem, 2008, 56(3):201-21.
Lykidis et al., "Novel zinc-based fixative for high quality DNA, RNA and protein analysis," Nucleic Acids Res., Jun. 2007, 35(12):e85, 10 pages.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
McCloskey et al., "Encoding PCR products with batch-stamps and barcodes," Biochem. Genet., 2007, 45(11-12):761-767.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans-chromatin interaction networks using chromosome conformation capture (3C)," Methods Mol Biol., 2009, 464:105-21.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Miner et al., "Molecular barcodes detect redundancy and contamination in hairpin-bisulfite PCR," Nucleic Acids Res., Sep. 2004, 32(17):e135, 4 pages.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.
Mizusawa et al., "A bacteriophage lambda vector for cloning with BamHI and Sau3A," Gene, 1982, 20(3):317-322.
Morlan et al., "Selective depletion of rRNA enables whole transcriptome profiling of archival fixed tissue," PLoS One, Aug. 2012, 7(8):e42882, 8 pages.
Motea et al., "Terminal deoxynucleotidyl transferase: the story of a misguided DNA polymerase," Biochim Biophys Acta., May 2010, 1804(5):1151-66.
Mulder et al., "CapTCR-seq: hybrid capture for T-cell receptor repertoire profiling," Blood Advances, Dec. 2018, 2(23):3506-3514.
Nadji et al., "Immunohistochemistry of tissue prepared by a molecular-friendly fixation and processing system," Appl Immunohistochem Mol Morphol., Sep. 2005, 13(3):277-82.
Nandakumar et al., "How an RNA Ligase Discriminates RNA versus DNA Damage," Molecular Cell, 2004, 16:211-221.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nichols et al., "RNA Ligases," Curr Protoc Mol Biol., Oct. 2008, 84(1):3.15.1-3.15.4.
Niedringhaus et al., "Landscape of next-generation sequencing technologies," Anal Chem., Jun. 2011, 83(12):4327-41.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nilsson et al., "RNA-templated DNA ligation for transcript analysis," Nucleic Acids Res., Jan. 2001, 29(2):578-81.
Nowak et al., "Entering the Postgenome Era," Science, 1995, 270(5235):368-71.
Ohtsubo et al., "Bacterial insertion sequences," Curr Top Microbiol Immunol., 1996, 204:1-26.
Olivier, "The Invader assay for SNP genotyping," Mutat. Res., Jun. 2005, 573(1-2):103-110.

(56) References Cited

OTHER PUBLICATIONS

Ozsolak et al., "Digital transcriptome profiling from attomole-level RNA samples," Genome Res., Apr. 2010, 20(4):519-25.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.
Passow et al., "RNAlater and flash freezing storage methods nonrandomly influence observed gene expression in RNAseq experiments," bioRxiv, Jul. 2018, 28 pages.
PCT International Preliminary Report on Patentability in International Appln. No. PCT/EP2016/057355, dated Oct. 10, 2017, 7 pages.
PCT International Preliminary Report on Patentability in International Appln. No. PCT/US2019/048425, dated Mar. 2, 2021, 9 pages.
PCT International Preliminary Report on Patentability in International Appln. No. PCT/US2019/048434, dated Mar. 2, 2021, 15 pages.
PCT International Preliminary Report on Patentability in International Appln. No. PCT/US2021/018795, dated Sep. 1, 2022, 10 pages.
PCT International Preliminary Report on Patentability in International Appln. No. PCT/US2021/018816, dated Sep. 1, 2022, 9 pages.
PCT International Search Report and Written Opinion in International Appln. No. PCT/US2020/066681, dated Apr. 14, 2021, 17 pages.
PCT International Search Report and Written Opinion in International Appln. No. PCT/US2021/012659, dated Apr. 16, 2021, 15 pages.
PCT International Search Report and Written Opinion in International Appln. No. PCT/US2021/018795, dated May 12, 2021, 19 pages.
PCT International Search Report and Written Opinion in International Appln. No. PCT/US2022/028071, dated Aug. 25, 2022, 13 pages.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perler et al., "Intervening sequences in an Archaea DNA polymerase gen," Proc Natl Acad Sci USA, Jun. 1992, 89(12):5577-5581.
Perocchi et al., "Antisense artifacts in transcriptome microarray experiments are resolved by actinomycin D," Nucleic Acids Res., 2007, 35(19):e128, 7 pages.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Pirici et al., "Antibody elution method for multiple immunohistochemistry on primary antibodies raised in the same species and of the same subtypem," J. Histochem. Cytochem., Jun. 2009, 57(6):567-75.
Plasterk, "The Tc1/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Salmén et al., "Barcoded solid-phase RNA capture for Spatial Transcriptomics profiling in mammalian tissue sections," Nature Protocols, Oct. 2018, 13(11):2501-2534.
Sanchez-Vega et al., "Oncogenic Signaling Pathways in the Cancer Genome Atlas," Cell, Apr. 2018, 173(2):321-337.e10, 28 pages.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schouten et al., "Relative quantification of 40 nucleic acid sequences by multiplex ligation-dependent probe amplification," Nucleic Acids Res., Jun. 2002, 30(12):e57, 13 pages.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.

(56) References Cited

OTHER PUBLICATIONS

Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Slomovic et al., "Addition of poly(A) and poly(A)-rich tails during RNA degradation in the cytoplasm of human cells," Proc Natl Acad Sci USA, Apr. 2010, 107(16):7407-12.
Sountoulidis et al., "SCRINSHOT, a spatial method for single-cell resolution mapping of cell states in tissue sections," PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Sutherland et al., "Utility of formaldehyde cross-linking and mass spectrometry in the study of protein-protein interactions," J. Mass Spectrom., Jun. 2008, 43(6):699-715.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Thorsson et al., "The Immune Landscape of Cancer," Immunity, Apr. 2018, 48(4):812-830, 37 pages.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue, " PLoS ONE, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandenbroucke et al., "Quantification of splice variants using real-time PCR," Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "Imaging-based pooled CRISPR screening reveals regulators of IncRNA localization," Proc Natl Acad Sci USA, May 2019, 116(22):10842-10851.
Wang et al., "Optimization of Process Conditions for Infected Animal Tissues by Alkaline Hydrolysis Technology," Procedia Environmental Sciences, 2016, 31:366-374.
Wang et al., "Tagmentation-based whole-genome bisulfite sequencing," Nature Protocols, Oct. 2013, 8(10):2022-2032.
Wang et al., "High-fidelity mRNA amplification for gene profiling," Nature Biotechnology, Apr. 2000, 18(4):457-459.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.
Wohnhaas et al., "DMSO cryopreservation is the method of choice to preserve cells for droplet-based single-cell RNA sequencing," Scientific Reports, Jul. 2019, 9(1):10699, 14 pages.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.

(56) References Cited

OTHER PUBLICATIONS

Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples," Commun Biol., Nov. 2018, 1:209, 8 pages.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Yeakley et al., "Profiling alternative splicing on fiber-optic arrays," Nature biotechnology, 2002, 20:353-358.
Yeakley et al., "A trichostatin A expression signature identified by TempO-Seq targeted whole transcriptome profiling, " PLoS One, May 2017, 12(5):e0178302, 22 pages.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase, " PNAS, 2005, 102(44):15815-20.
Zhang et al., "Archaeal RNA ligase from Thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Genome-wide open chromatin regions and their effects on the regulation of silk protein genes in Bombyx mori," Sci Rep., Oct. 2017, 7(1):12919, 9 pages.
Zhang et al., "Multiplex ligation-dependent probe amplification (MLPA) for ultrasensitive multiplexed microRNA detection using ribonucleotide-modified DNA probest," Chem. Commun., 2013, 49:10013-10015.
Zhao et al., "Isothermal Amplification of Nucleic Acids," Chemical Reviews, Nov. 2015, 115(22):12491-12545.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
Hobro et al., "An evaluation of fixation methods: Spatial and compositional cellular changes observed by Raman imaging," Vibrational Spectroscopy, Jul. 2017, 91:31-45.
Landegren et al., "A Ligase-Mediated Gene Detection Technique," Science, 1988, 241(4869):1077-1080.
Schmidl et al., "ChIPmentation: fast, robust, low-input ChIP-seq for histones and transcription factors," Nature Methods, Oct. 2015, 12:963-965.
Bibikova et al., "Quantitative gene expression profiling in formalin-fixed paraffin-embedded tissues using universal bead arrays," The American Journal of Pathology, Nov. 1, 2004, 165(5):1799-1807.
Choi et al., "Multiplexed detection of mRNA using porosity-tuned hydrogel microparticles," Analytical chemistry, Sep. 28, 2012, 84(21):9370-9378.
Fan et al., "A versatile assay for high-throughput gene expression profiling on universal array matrices," Genome Research, May 1, 2004, 14(5):878-885.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Sun et al., "Statistical Analysis of Spatial Expression Pattern for Spatially Resolved Transcriptomic Studies," Nature Methods, Jan. 27, 2020, 17(2): 193-200.
Svensson et al., "SpatialDE: identification of spatially variable genes," Nature Methods, May 2018, 15:343-346, 15 pages.
Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.
Belton et al., "Hi-C: A comprehensive technique to capture the conformation of genomes," Methods, Nov. 2012, 58(3):268-276, 16 pages.
Bentzen et al., "Large-scale detection of antigen-specific T cells using peptide-MHC-I multimers labeled with DNA barcodes," Nat Biotechnol., Oct. 2016, 34(10):1037-1045, 12 pages.
Chen et al. "Arrayed profiling of multiple glycans on whole living cell surfaces." Analytical chemistry, Oct. 15, 2013, 85(22):11153-11158.
Fan et al., "Illumina Universal Bead Arrays," Methods in Enzymology, 2006, 410:57-73.
Hadrup et al., "Parallel detection of antigen-specific T-cell responses by multidimensional encoding of MHC multimers," Nat. Methods., Jul. 2009, 6(7), 520-526.
Mamedov et al., "Preparing unbiased T-cell receptor and antibody cDNA libraries for the deep next generation sequencing profiling," Frontiers in Immunol., Dec. 23, 2013, 4(456):1-10.
Oksuz et al., "Systematic evaluation of chromosome conformation capture assays," Nature Methods, Sep. 2021, 18:1046-1055.
Rohland et al., "Partial uracil-DNA-glycosylase treatment for screening of ancient DNA," Phil. Trans. R. Soc. B, Jan. 19, 2015, 370(1660): 20130624, 11 pages.
Su et al., "Restriction enzyme selection dictates detection range sensitivity in chromatin conformation capture-based variant-to-gene mapping approaches," bioRxiv, Dec. 15, 2020, 22 pages.
Howell et al., "iFRET: An Improved Fluorescence System for DNA-Melting Analysis," Genome Research, 2002, 12:1401-1407.
Nam et al., "Nanoparticle-Based Bio-Bar Codes for the Ultrasensitive Detection of Proteins," Science, Sep. 26, 2003, 301(5641):1884-1886.
Redmond et al., "Single-cell TCRseq: paired recovery of entire T-cell alpha and beta chain transcripts in T-cell receptors from single-cell RNAseq," Genome Med, 2016, 8:80, 12 pages.

Final library from GEX

+ Biotinylated hybridization bait pool

Hybridize baits & blockers to
single stranded library members

Pull down baits and hybridized library to
streptavidin beads

Wash beads to remove unbound probes

PCR on streptavidin beads to reamplify
targeted library

Final Library QC (Bioanalyzer, P5 - P7 qPCR)

Sequence targeted library

CAPTURING GENETIC TARGETS USING A HYBRIDIZATION APPROACH

CROSS-REFERENCE TO RELATED APPLICATION

Pursuant to 35 U.S.C. § 119(e), this application is a continuation of International Application PCT/US2021/018795, with an international filing date of Feb. 19, 2021, which claims priority to U.S. Provisional Patent Application No. 62/979,652, filed Feb. 21, 2020; U.S. Provisional Patent Application No. 62/980,124, filed Feb. 21, 2020; and U.S. Provisional Patent Application No. 63/077,019, filed Sep. 11, 2020. The contents of the foregoing applications are incorporated herein by reference in its entirety.

BACKGROUND

Cells within a tissue of a subject have differences in cell morphology and/or function due to varied analyte abundance (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provide a lot of analyte data for single cells, but fail to provide information regarding the position of the single cell in a parent biological sample (e.g., tissue sample).

Whole exome sequencing provides coverage for each transcripts in a sample. There is a need in the art for a transcriptome-specific method for the high-fidelity enrichment of nucleic acid molecules for targeted sequencing while reducing cost, maximizing efficiency, and minimizing redundancy.

SUMMARY

Disclosed herein is a method for identifying abundance and location of an analyte in a biological sample, the method comprising: (a) contacting a plurality of nucleic acids with a plurality of bait oligonucleotides, in some embodiments, the plurality of nucleic acids comprises an extended nucleic acid comprising (i) a spatial barcode or a complement thereof, and (ii) all or a portion of a sequence of the analyte, an analyte derivative, or a complement thereof; and a bait oligonucleotide of the plurality of bait oligonucleotides comprises: (i) a capture domain that hybridizes to all or a portion of the sequence of the analyte, the analyte derivative, or a complement thereof, and (ii) a molecular tag; (b) capturing the bait oligonucleotide bound to the extended nucleic acid using a substrate comprising an agent that binds to the molecular tag; and (c) determining (i) all or a portion of the sequence of the spatial barcode or the complement thereof, and (ii) all or a portion of the sequence of the extended nucleic acid, and using the determined sequences of (i) and (ii) to identify the abundance and the location of the analyte in the biological sample.

In some embodiments, the analyte is a nucleic acid.

In some embodiments, the method further comprises generating the plurality of nucleic acids, which comprises: (a) contacting the biological sample with a substrate comprising a plurality of attached capture probes, in some embodiments, a capture probe of the plurality comprises (i) the spatial barcode and (ii) a capture domain that binds to a sequence present in the nucleic acid; (b) hybridizing the capture probe to the nucleic acid; (c) extending a 3' end of the capture probe using the nucleic acid that is bound to the capture domain as a template to generate an extended capture probe; and (d) amplifying the extended capture probe to produce the extended nucleic acid.

In some embodiments, the extended nucleic acid is released from the extended capture probe.

In some embodiments, the analyte is a protein.

In some embodiments, the analyte derivative is an oligonucleotide comprising an analyte binding moiety barcode, and an analyte capture sequence.

In some embodiments, the method further comprises generating the plurality of nucleic acids, the method comprising: (a) contacting a plurality of analyte capture agents to the biological sample, in some embodiments, an analyte capture agent of the plurality of the analyte capture agents comprises (i) an analyte binding moiety that binds to the protein and (ii) the oligonucleotide comprising the analyte binding moiety barcode and the analyte capture sequence; (b) contacting the plurality of analyte capture agents to a substrate comprises a plurality of capture probes, in some embodiments, a capture probe of the plurality comprises the spatial barcode and a capture domain, in some embodiments, the capture domain binds to the analyte capture sequence; (c) extending a 3' end of the capture probe using the analyte binding moiety barcode as a template to generate an extended capture probe; and (d) amplifying the extended capture probe to produce the extended nucleic acid.

In some embodiments, the extended nucleic acid is released from the extended capture probe.

In some embodiments, step (a) and step (b) are performed at substantially the same time. In some embodiments, step (a) is performed prior to step (b). In some embodiments, step (b) is performed prior to step (a).

Also disclosed herein is a method for enriching an analyte or an analyte derivative in a biological sample, the method comprising: (a) contacting a plurality of nucleic acids with a plurality of bait oligonucleotides, in some embodiments, the plurality of nucleic acids comprises an extended nucleic acid comprising (i) a spatial barcode or a complement thereof, and (ii) all or a portion of a sequence of the analyte, an analyte derivative, or a complement thereof; and a bait oligonucleotide of the plurality of bait oligonucleotides comprises: (i) a capture domain that hybridizes to all or a portion of the sequence of the analyte, the analyte derivative, or a complement thereof, and (ii) a molecular tag; (b) capturing a complex of the bait oligonucleotide bound to the extended nucleic acid using a substrate comprising an agent that binds to the molecular tag; and (c) isolating the complex of the bait oligonucleotide bound to the extended nucleic acid, thereby enriching the analyte or the analyte derivative in the biological sample.

In some embodiments, the analyte is a nucleic acid.

In some embodiments, the method further comprises generating the plurality of nucleic acids, which comprises: (a) contacting the biological sample with a substrate comprising a plurality of attached capture probes, in some embodiments, a capture probe of the plurality comprises (i) the spatial barcode and (ii) a capture domain that binds to a sequence present in the nucleic acid; (b) hybridizing the capture probe to the nucleic acid; (c) extending a 3' end of the capture probe using the nucleic acid that is bound to the capture domain as a template to generate an extended capture probe; and (d) amplifying the extended capture probe to produce the extended nucleic acid.

In some embodiments, the extended nucleic acid is released from the extended capture probe.

In some embodiments, the analyte is a protein.

In some embodiments, the analyte derivative is an oligonucleotide comprising an analyte binding moiety barcode, and an analyte capture sequence.

In some embodiments, the method further comprises generating the plurality of nucleic acids, the method comprising: (a) contacting a plurality of analyte capture agents to the biological sample, in some embodiments, an analyte capture agent of the plurality of the analyte capture agents comprises (i) an analyte binding moiety that binds to the protein and (ii) the oligonucleotide comprising the analyte binding moiety barcode and the analyte capture sequence; (b) contacting the plurality of analyte capture agents to a substrate comprises a plurality of capture probes, in some embodiments, a capture probe of the plurality comprises the spatial barcode and a capture domain, in some embodiments, the capture domain binds to the analyte capture sequence; (c) extending a 3' end of the capture probe using the analyte binding moiety barcode as a template to generate an extended capture probe; and (d) amplifying the extended capture probe to produce the extended nucleic acid.

In some embodiments, the extended nucleic acid is released from the extended capture probe.

In some embodiments, step (a) and step (b) are performed at substantially the same time. In some embodiments, step (a) is performed prior to step (b). In some embodiments, step (b) is performed prior to step (a).

In some embodiments, the analyte from the biological sample is associated with a disease or condition.

In some embodiments, the capture domain of the bait oligonucleotide binds to a 3' portion, a 5' portion, an intron, an exon, an untranslated 3' region, or an untranslated 5' region of the sequence of the analyte, the analyte derivative, or a complement thereof.

In some embodiments, the capture domain of the bait oligonucleotide comprises a total of about 10 nucleotides to about 300 nucleotides.

In some embodiments, the molecular tag comprises a protein, a small molecule, a nucleic acid, or a carbohydrate.

In some embodiments, the molecular tag is streptavidin, avidin, biotin, or a fluorophore.

In some embodiments, the agent that binds to the molecular tag comprises a protein (e.g., an antibody), a nucleic acid, or a small molecule.

In some embodiments, the molecular tag is biotin and the agent that binds to the molecular tag is avidin or streptavidin.

In some embodiments, the agent that binds specifically to the molecular tag is attached to a substrate. In some embodiments, the substrate is a bead, a well, or a slide.

In some embodiments, the extended nucleic acid is a DNA molecule (e.g., a cDNA molecule).

In some embodiments, the extended nucleic acid further comprises a primer sequence or a complement thereof; a unique molecular sequence or a complement thereof; or an additional primer binding sequence or a complement thereof.

In some embodiments, the biological sample is a tissue sample selected from a formalin-fixed, paraffin-embedded (FFPE) tissue sample or a frozen tissue sample.

In some embodiments, the biological sample was previously stained using a detectable label, a hematoxylin and eosin (H&E) stain, immunofluorescence, or immunohistochemistry.

In some embodiments, the biological sample is a permeabilized biological sample.

In some embodiments, the determining step described herein comprises sequencing (i) all or a portion of the sequence of the spatial barcode or the complement thereof, and (ii) all or a portion of the sequence of the nucleic acid from the biological sample.

In some embodiments, the sequencing is high throughput sequencing.

In some embodiments, the analyte is dysregulated or differentially expressed in a cancer cell, an immune cell, a cellular signaling pathway, or a neurological cell.

Also disclosed herein is a method for identifying abundance and location of a nucleic acid in a biological sample, the method comprising: (a) contacting the biological sample with a substrate comprising a plurality of attached capture probes, in some embodiments, a capture probe of the plurality comprises (i) a spatial barcode and (ii) a capture domain that binds to a sequence present in the nucleic acid; (b) hybridizing the capture probe to the nucleic acid; (c) extending a 3' end of the capture probe using the nucleic acid that is bound to the capture domain as a template to generate an extended capture probe; and (d) amplifying the extended capture probe to produce the extended nucleic acid; in some embodiments, the extended nucleic acid comprises (i) the spatial barcode or a complement thereof, and (ii) all or a portion of a sequence of the nucleic acid, or a complement thereof; (e) releasing the extended nucleic acid from the extended capture probe; (f) contacting a plurality of the released nucleic acids comprising the extended nucleic acid from step (e) with a plurality of bait oligonucleotides, in some embodiments, a bait oligonucleotide of the plurality of bait oligonucleotides comprises: (i) a capture domain that hybridizes to all or a portion of the sequence of the nucleic acid, or a complement thereof, and (ii) a molecular tag; (g) capturing the bait oligonucleotide bound to the extended nucleic acid using a substrate comprising an agent that binds to the molecular tag; and (h) determining (i) all or a portion of the sequence of the spatial barcode or the complement thereof, and (ii) all or a portion of the sequence of the extended nucleic acid, and using the determined sequences of (i) and (ii) to identify the abundance and the location of the nucleic acid in the biological sample.

Also disclosed herein is a method for identifying abundance and location of a protein in a biological sample, the method comprising: (a) contacting a plurality of analyte capture agents to the biological sample, in some embodiments: an analyte capture agent of the plurality of the analyte capture agents comprises (i) an analyte binding moiety that binds to the protein and (ii) an oligonucleotide comprising an analyte binding moiety barcode and an analyte capture sequence; (b) contacting the plurality of analyte capture agents to a substrate comprises a plurality of capture probes, in some embodiments, a capture probe of the plurality comprises a spatial barcode and a capture domain, in some embodiments, the capture domain binds to the analyte capture sequence; (c) extending a 3' end of the capture probe using the analyte binding moiety barcode as a template to generate an extended capture probe; (d) amplifying the extended capture probe to produce the extended nucleic acid; in some embodiments, the extended nucleic acid comprises (i) the spatial barcode or a complement thereof, and (ii) all or a portion of a sequence of the oligonucleotide, or a complement thereof; (e) releasing the extended nucleic acid from the extended capture probe; (f) contacting a plurality of the released nucleic acids comprising the extended nucleic acid from step (e) with a plurality of bait oligonucleotides, in some embodiments, a bait oligonucleotide of the plurality of bait oligonucleotides comprises: (i) a capture domain that hybridizes to all or a portion of the sequence of the oligonucleotide, or a complement thereof, and (ii) a molecular tag; (g) capturing the bait oligonucleotide bound to the extended nucleic acid using a substrate comprising an agent that binds to the molecular tag; and (h) determining (i) all or a portion of the sequence of the spatial barcode or the complement thereof, and (ii) all or a portion of the sequence of the extended nucleic acid, and using the determined sequences of (i) and (ii) to identify the abundance and the location of the protein in the biological sample.

Also disclosed herein is a composition comprising a bait oligonucleotide and an extended nucleic acid, in some embodiments, the bait oligonucleotide is bound to the extended nucleic acid, in some embodiments, the extended nucleic acid comprises (i) a spatial barcode or a complement thereof, and (ii) all or a portion of a sequence of an analyte, an analyte derivative, or a complement thereof; and in some embodiments, the bait oligonucleotide comprises a molecular tag, in some embodiments, the molecular tag is selected from the group consisting of streptavidin, avidin, biotin, or a fluorophore.

In some embodiments, the bait oligonucleotide is bound to the extended nucleic acid by a capture domain that hybridizes to all or a portion of the sequence of the analyte, the analyte derivative, or a complement thereof.

In some embodiments, the composition as described herein further comprises an agent that binds to the molecular tag.

In some embodiments, the agent that binds to the molecular tag comprises a protein (e.g., an antibody), a nucleic acid, or a small molecule.

In some embodiments, the molecular tag is biotin and the agent that binds to the molecular tag is avidin or streptavidin.

In some embodiments, the composition as described herein further comprises a substrate, in some embodiments, the agent that binds to the molecular tag is attached to the substrate. In some embodiments, the substrate is a bead, a well, or a slide.

Also disclosed herein is a kit comprising: an array comprising a plurality of capture probes, in some embodiments, a capture probe of the plurality of capture probes comprises a spatial barcode and a capture domain; a plurality of bait oligonucleotides; and instructions for performing the method as described herein.

Also disclosed herein is a kit comprising: a plurality of analyte capture agents, in some embodiments, an analyte capture agent of the plurality of analyte capture agents comprises an analyte binding moiety, an analyte binding moiety barcode, and an analyte capture sequence; an array comprising a plurality of capture probes, in some embodiments, a capture probe of the plurality of capture probes comprises a spatial barcode and a capture domain; a plurality of bait oligonucleotides; and instructions for performing the method as described herein.

In some embodiments, the kit as described herein further comprises reagents and/or enzymes for performing the method.

Also disclosed herein is a method for identifying a location nucleic acid in a biological sample, the method comprising: (a) contacting a plurality of nucleic acids from a biological sample with a plurality of bait oligonucleotides, in some embodiments, a plurality of nucleic acids comprises (i) a spatial barcode or a complement thereof, and (ii) a portion of a sequence of a nucleic acid from a biological sample, or a complement thereof; and a bait oligonucleotide of the plurality of bait oligonucleotides comprises: a capture domain that binds specifically to all or a portion of the sequence of the nucleic acid from the biological sample, or a complement thereof, and a molecular tag; (b) capturing the bait oligonucleotide specifically bound to the nucleic acid using a substrate comprising an agent that binds specifically to the molecular tag; and (c) determining (i) all or a portion of the sequence of the spatial barcode or the complement thereof, and (ii) all or a portion of the sequence of the nucleic acid from the biological sample, and using the determined sequences of (i) and (ii) to identify the location of the nucleic acid in the biological sample.

In some embodiments, the capture domain of the bait oligonucleotide binds specifically to all or a portion of the sequence of the nucleic acid from the biological sample. In some embodiments, the capture domain of the bait oligonucleotide binds specifically to a 3' portion of the sequence of the nucleic acid from the biological sample or a complement thereof. In some embodiments, the capture domain of the bait oligonucleotide binds specifically to a 5' portion of the sequence of the nucleic acid from the biological sample or a complement thereof. In some embodiments, the capture domain of the bait oligonucleotide binds specifically to an intron in the sequence of the nucleic acid from the biological sample or a complement thereof. In some embodiments, the capture domain of the bait oligonucleotide binds specifically to an exon in the sequence of the nucleic acid from the biological sample or a complement thereof. In some embodiments, the capture domain of the bait oligonucleotide binds specifically to an untranslated 3' region of the nucleic acid from the biological sample or a complement thereof. In some embodiments, the capture domain of the bait oligonucleotide binds specifically to an untranslated 5' region of the nucleic acid from the biological sample or a complement thereof.

In some embodiments, the nucleic acid from the biological sample is associated with a disease or condition. In some embodiments, the nucleic acid from the biological sample comprises a mutation. In some embodiments, the nucleic acid from the biological sample comprises a single nucleotide polymorphism (SNP). In some embodiments, the nucleic acid from the biological sample comprises a trinucleotide repeat.

In some embodiments, the capture domain of the bait oligonucleotide comprises a total of about 10 nucleotides to about 300 nucleotides.

In some embodiments, the molecular tag comprises a moiety. In some embodiments, the moiety is streptavidin, avidin, biotin, or a fluorophore. In some embodiments, the molecular tag comprises a small molecule. In some embodiments, the molecular tag comprises a nucleic acid. In some embodiments, the molecular tag comprises a carbohydrate. In some embodiments, the molecular tag is positioned 5' to the capture domain in the bait oligonucleotide. In some embodiments, the molecular tag is position 3' to the capture domain in the bait oligonucleotide. In some embodiments, the agent that binds specifically to the molecular tag comprises a protein. In some embodiments, the protein is an antibody. In some embodiments, the agent that binds specifically to the molecular tag comprises a nucleic acid. In some embodiments, the agent that binds specifically to the molecular tag comprises a small molecule. In some embodiments, the agent that binds specifically to the molecular tag is attached to a substrate. In some embodiments, the substrate is a bead. In some embodiments, the substrate is a well. In some embodiments, the substrate is a slide.

In some embodiments, the nucleic acid is DNA. In some embodiments, the nucleic acid further comprises a functional sequence. In some embodiments, the functional sequence is a primer sequence or a complement thereof. In some embodiments, the nucleic acid further comprises a unique molecular sequence or a complement thereof. In some embodiments, the nucleic acid further comprises an additional primer binding sequence or a complement thereof.

In some embodiments, the biological sample is a tissue sample. In some embodiments, the tissue sample is a formalin-fixed, paraffin-embedded (FFPE) tissue sample or a frozen tissue sample. In some embodiments, the biological sample was previously stained using a detectable label. In some embodiments, the biological sample was previously stained. In some embodiments, the biological sample was previously stained using hematoxylin and eosin (H&E). In some embodiments, the biological sample was previously stained using immunofluorescence or immunohistochemistry. In some embodiments, the biological sample is a permeabilized biological sample that has been permeabilized with a permeabilization agent selected from an organic solvent, a cross-linking agent, a detergent, and an enzyme, or a combination thereof. In some embodiments, the permeabilization agent is a cross-linking agent. In some embodiments, the analyte is an RNA molecule. In some embodiments, the RNA molecule is an mRNA molecule.

In some embodiments, the determining in step (c) comprises sequencing (i) all or a portion of the sequence of the spatial barcode or the complement thereof, and (ii) all or a portion of the sequence of the nucleic acid from the biological sample. In some embodiments, the sequencing is high throughput sequencing. In some embodiments, the sequencing comprises ligating an adapter to the nucleic acid.

In some embodiments, the method further comprises generating the plurality of nucleic acids comprises: (a) contacting the biological sample with a substrate comprising a plurality of attached capture probes, in some embodiments, a capture probe of the plurality comprises (i) the spatial barcode and (ii) a capture domain that binds specifically to a sequence present in the analyte; (b) extending a 3' end of the capture probe using the analyte that is specifically bound to the capture domain as a template to generate an extended capture probe; and (c) amplifying the extended capture probe to produce the nucleic acid. In some embodiments, the amplifying is isothermal.

In some embodiments, the produced nucleic acid is released from the extended capture probe.

In some embodiments, the nucleic acid is dysregulated or differentially expressed in a cancer cell. In some embodiments, the nucleic acid is dysregulated or differentially expressed in an immune cell. In some embodiments, the nucleic acid is dyregulated in a cellular signaling pathway. In some embodiments, the nucleic acid is dyregulated or differentially expressed in a neurological cell.

Also disclosed herein is a method for identifying a location of a nucleic acid in a biological sample, the method comprising: (a) contacting a plurality of nucleic acids with a plurality of bait oligonucleotides, in some embodiments, a nucleic acid of the plurality of nucleic acids comprises (i) a spatial barcode or a complement thereof, and (ii) a portion of a binding moiety barcode, or a complement thereof; and a bait oligonucleotide of the plurality of bait oligonucleotides comprises: a capture domain that binds specifically (i) all of a portion of the nucleic acid, or a complement thereof, and/or (ii) all or a portion of the binding moiety barcode, or a complement thereof, and a molecular tag; (b) capturing a complex of the bait oligonucleotide specifically bound to the nucleic acid or a complement thereof, or a complex of the bait oligonucleotide specifically bound to the analyte binding moiety barcode or a complement thereof, using a substrate comprising an agent that binds specifically to the molecular tag; and (c) determining (i) all or a portion of the sequence of the nucleic acid or the complement thereof, and/or (ii) all or a portion of the sequence of the analyte binding moiety barcode or the complement thereof, and using the determined sequences of (i) and (ii) to identify the location of the nucleic acid in the biological sample.

In some embodiments, the capture domain of the bait oligonucleotide binds specifically to all or a portion of the nucleic acid sequence from the biological sample. In some embodiments, the capture domain of the bait oligonucleotide binds specifically to all or a portion of the analyte binding moiety barcode.

In some embodiments, the nucleic acid from the biological sample is associated with a disease or condition.

In some embodiments, the capture domain of the bait oligonucleotide comprises a total of about 10 nucleotides to about 300 nucleotides.

In some embodiments, the molecular tag comprises a protein. In some embodiments, the protein is streptavidin, avidin, or biotin. In some embodiments, the molecular tag comprises a small molecule. In some embodiments, the molecular tag comprises a nucleic acid. In some embodiments, the molecular tag comprises a carbohydrate. In some embodiments, the molecular tag is positioned 5' to the domain in the bait oligonucleotide. In some embodiments, the molecular tag is position 3' to the domain in the bait oligonucleotide. In some embodiments, the agent that binds specifically to the molecular tag comprises a protein. In some embodiments, the protein is an antibody. In some embodiments, the agent that binds specifically to the molecular tag comprises a nucleic acid. In some embodiments, the agent that binds specifically to the molecular tag comprises a small molecule.

In some embodiments, the agent that binds specifically to the molecular tag is attached to a substrate. In some embodiments, the substrate is a bead. In some embodiments, the substrate is a well. In some embodiments, the substrate is a slide.

In some embodiments, the nucleic acid is DNA. In some embodiments, the nucleic acid further comprises a primer binding sequence or a complement thereof. In some embodiments, the nucleic acid further comprises a unique molecular sequence or a complement thereof. In some embodiments, the nucleic acid further comprises an additional primer binding sequence or a complement thereof.

In some embodiments, the biological sample is a tissue sample. In some embodiments, the tissue sample is a formalin-fixed, paraffin-embedded (FFPE) tissue sample or a frozen tissue sample. In some embodiments, the biological sample was previously stained using a detectable label. In some embodiments, the biological sample was previously stained. In some embodiments, the biological sample was previously stained using hematoxylin and eosin (H&E). In some embodiments, the biological sample was previously stained using immunofluorescence or immunohistochemistry. In some embodiments, the biological sample is a permeabilized biological sample that has been permeabilized with a permeabilization agent selected from an organic solvent, a cross-linking agent, a detergent, and an enzyme, or a combination thereof. In some embodiments, the permeabilization agent is selected from an organic solvent, a cross-linking agent, a detergent, and an enzyme, or a combination thereof. In some embodiments, the analyte is an RNA molecule. In some embodiments, the RNA molecule is an mRNA molecule.

In some embodiments, the determining in step (c) comprises sequencing (i) all or a portion of the sequence of the nucleic acid or the complement thereof, and (ii) all or a portion of the sequence of the analyte binding moiety barcode. In some embodiments, the sequencing is high throughput sequencing. In some embodiments, the sequencing comprises ligating an adapter to the nucleic acid.

In some embodiments, the method further comprises generating the plurality of nucleic acids comprises: (a) contacting a plurality of capture agents to the biological sample disposed on a substrate, in some embodiments, a capture agent of the plurality of the capture agents comprises (i) a binding moiety that binds specifically to the nucleic acid in the biological sample, (ii) a binding moiety barcode; and (iii) a capture sequence; and the substrate comprises a plurality of capture probes, in some embodiments, a capture probe of the plurality comprises a spatial barcode and a capture domain, in some embodiments, the capture domain binds specifically to the analyte capture sequence; and (b) extending a 3' end of the capture probe using the analyte binding moiety barcode as a template to generate an extended capture probe; and (c) amplifying the extended capture probe to produce the nucleic acid. In some embodiments, the amplifying is isothermal.

In some embodiments, the produced nucleic acid is released from the extended capture probe. In some embodiments, the nucleic acid is a nucleic acid that is dysregulated or differentially expressed in a cancer cell. In some embodiments, the nucleic acid is a nucleic acid that is dysregulated or differentially expressed in an immune cell. In some embodiments, the nucleic acid is a nucleic acid that is dyregulated in a cellular signaling pathway. In some embodiments, the nucleic acid is a nucleic acid that is dyregulated or differentially expressed in a neurological cell.

Also disclosed herein is a method for enriching a nucleic acid in a biological sample, the method comprising: (a) contacting a plurality of nucleic acids with a plurality of bait oligonucleotides, in some embodiments, a nucleic acid of the plurality of nucleic acids comprises (i) a spatial barcode or a complement thereof, and (ii) a portion of a binding moiety barcode, or a complement thereof; and a bait oligonucleotide of the plurality of bait oligonucleotides comprises: a capture domain that binds specifically (i) all of a portion of the nucleic acid, or a complement thereof, and/or (ii) all or a portion of the binding moiety barcode, or a complement thereof, and a molecular tag; (b) capturing a complex of the bait oligonucleotide specifically bound to the nucleic acid or a complement thereof, or a complex of the bait oligonucleotide specifically bound to the analyte binding moiety barcode or a complement thereof, using a substrate comprising an agent that binds specifically to the molecular tag; and (c) isolating the complex of the bait oligonucleotide specifically bound to the nucleic acid or a complement thereof, or a complex of the bait oligonucleotide specifically bound to the analyte binding moiety barcode or a complement thereof, thereby enriching the nucleic acid in the biological sample.

In some embodiments, the capture domain of the bait oligonucleotide binds specifically to all or a portion of the nucleic acid sequence from the biological sample. In some embodiments, the capture domain of the bait oligonucleotide binds specifically to all or a portion of the analyte binding moiety barcode. In some embodiments, the nucleic acid from the biological sample is associated with a disease or condition. In some embodiments, the capture domain of the bait oligonucleotide comprises a total of about 10 nucleotides to about 300 nucleotides.

In some embodiments, the molecular tag comprises a protein. In some embodiments, the protein is streptavidin, avidin, or biotin. In some embodiments, the molecular tag comprises a small molecule. In some embodiments, the molecular tag comprises a nucleic acid. In some embodiments, the molecular tag comprises a carbohydrate. In some embodiments, the molecular tag is positioned 5' to the domain in the bait oligonucleotide. In some embodiments, the molecular tag is position 3' to the domain in the bait oligonucleotide. In some embodiments, the agent that binds specifically to the molecular tag comprises a protein. In some embodiments, the protein is an antibody. In some embodiments, the agent that binds specifically to the molecular tag comprises a nucleic acid. In some embodiments, the agent that binds specifically to the molecular tag comprises a small molecule. In some embodiments, the agent that binds specifically to the molecular tag is attached to a substrate. In some embodiments, the substrate is a bead. In some embodiments, the substrate is a well. In some embodiments, the substrate is a slide.

In some embodiments, the nucleic acid is DNA. In some embodiments, the nucleic acid further comprises a primer binding sequence or a complement thereof. In some embodiments, the nucleic acid further comprises a unique molecular sequence or a complement thereof. In some embodiments, the nucleic acid further comprises an additional primer binding sequence or a complement thereof.

In some embodiments, the biological sample is a tissue sample. In some embodiments, the tissue sample is a formalin-fixed, paraffin-embedded (FFPE) tissue sample or a frozen tissue sample. In some embodiments, the biological sample was previously stained using a detectable label. In some embodiments, the biological sample was previously stained. In some embodiments, biological sample was previously stained using hematoxylin and eosin (H&E). In some embodiments, the biological sample was previously stained using immunofluorescence or immunohistochemistry.

In some embodiments, the biological sample is a permeabilized biological sample that has been permeabilized with a permeabilization agent selected from an organic solvent, a cross-linking agent, a detergent, and an enzyme, or a combination thereof. In some embodiments, the permeabilization agent is selected from an organic solvent, a cross-linking agent, a detergent, and an enzyme, or a combination thereof.

In some embodiments, the analyte is an RNA molecule. In some embodiments, the RNA molecule is an mRNA molecule.

In some embodiments, the method further comprises generating the plurality of nucleic acids comprises: (a) contacting a plurality of capture agents to the biological sample disposed on a substrate, in some embodiments, a capture agent of the plurality of the capture agents comprises (i) a binding moiety that binds specifically to the nucleic acid in the biological sample, (ii) a binding moiety barcode; and (iii) a capture sequence; and the substrate comprises a plurality of capture probes, in some embodiments, a capture probe of the plurality comprises a spatial barcode and a capture domain, in some embodiments, the capture domain binds specifically to the analyte capture sequence; and (b) extending a 3' end of the capture probe using the analyte binding moiety barcode as a template to generate an extended capture probe; and (c) amplifying the extended capture probe to produce the nucleic acid. In some embodiments, the amplifying is isothermal.

In some embodiments, the produced nucleic acid is released from the extended capture probe.

In some embodiments, the nucleic acid is a nucleic acid that is dysregulated or differentially expressed in a cancer cell. In some embodiments, the nucleic acid is a nucleic acid that is dysregulated or differentially expressed in an immune cell. In some embodiments, the nucleic acid is a nucleic acid that is dyregulated in a cellular signaling pathway. In some embodiments, the nucleic acid is a nucleic acid that is dyregulated or differentially expressed in a neurological cell.

Also disclosed herein is a method for identifying a location of a nucleic acid in a biological sample, the method comprising: (a) contacting a plurality of capture agents to the biological sample disposed on a substrate, in some embodiments, a capture agent of the plurality of the capture agents comprises (i) a binding moiety that binds specifically to the nucleic acid in the biological sample, (ii) a binding moiety barcode; and (iii) a capture sequence; and the substrate comprises a plurality of capture probes, in some embodiments, a capture probe of the plurality comprises a spatial barcode and a capture domain, in some embodiments, the capture domain binds specifically to the analyte capture sequence; and (b) extending a 3' end of the capture probe using the analyte binding moiety barcode as a template to generate an extended capture probe; and (c) amplifying the extended capture probe to produce the nucleic acid; in some embodiments, the nucleic acid comprises (i) a spatial barcode or a complement thereof, and (ii) a portion of an analyte binding moiety barcode, or a complement thereof; (d) releasing the produced nucleic acid from the extended capture probe; (e) contacting a plurality of released nucleic acids from step (d) with a plurality of bait oligonucleotides, in some embodiments, a bait oligonucleotide of the plurality of bait oligonucleotides comprises: a capture domain that binds specifically (i) all of a portion of the nucleic acid, or a complement thereof, and/or (ii) all or a portion of the analyte binding moiety barcode, or a complement thereof, and a molecular tag; (f) capturing a complex of the bait oligonucleotide specifically bound to the nucleic acid or a complement thereof, or a complex of the bait oligonucleotide specifically bound to the analyte binding moiety barcode or a complement thereof, using a substrate comprising an agent that binds specifically to the molecular tag; and (g) determining (i) all or a portion of the sequence of the nucleic acid or the complement thereof, and/or (ii) all or a portion of the sequence of the analyte binding moiety barcode or the complement thereof, and using the determined sequences of (i) and (ii) to identify the location of the nucleic acid in the biological sample.

Also disclosed herein is a composition comprising a bait oligonucleotide bound to a nucleic acid, in some embodiments, the nucleic acid comprises (i) a spatial barcode or a complement thereof, and (ii) a portion of an analyte binding moiety barcode, or a complement thereof.

In some embodiments, the bait oligonucleotide is bound to the nucleic acid by a capture domain that binds specifically (i) all of a portion of the nucleic acid, and/or (ii) all or a portion of the analyte binding moiety barcode, or a complement thereof.

In some embodiments, the composition further comprises a molecular tag. In some embodiments, the composition further comprises an agent that binds specifically to the molecular tag. In some embodiments, the molecular tag comprises a protein. In some embodiments, the protein is streptavidin, avidin, or biotin. In some embodiments, the molecular tag comprises a small molecule. In some embodiments, the molecular tag comprises a nucleic acid. In some embodiments, the molecular tag comprises a carbohydrate. In some embodiments, the molecular tag is positioned 5' to the domain in the bait oligonucleotide. In some embodiments, the molecular tag is position 3' to the domain in the bait oligonucleotide.

In some embodiments, the agent comprises streptavidin, avidin, or biotin. In some embodiments, the agent that binds specifically to the molecular tag comprises a protein. In some embodiments, the protein is an antibody. In some embodiments, the agent that binds specifically to the molecular tag comprises a nucleic acid. In some embodiments, the agent that binds specifically to the molecular tag comprises a small molecule.

In some embodiments, the composition further comprises a substrate. In some embodiments, the substrate is a bead. In some embodiments, the substrate is a well. In some embodiments, the substrate is a slide.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

As used herein, the term "analyte derivative" refers to a molecule (e.g., a nucleic acid or protein molecule) that is derived from an analyte (e.g., a nucleic acid), or conveys information (e.g., identity information) that corresponds to an analyte (e.g., a protein). In some embodiments, the analyte derivative comprises all or a portion of the analyte (e.g., a nucleic acid) described herein. In some embodiments, the analyte derivative comprises all or a portion of the analyte capture agent (e.g., all or a portion of the analyte capture moiety, the analyte binding moiety barcode, and/or the analyte capture sequence) described herein.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIG. 15C demonstrates the UMI correlation between FIG. 15A and FIG. 15B.

DETAILED DESCRIPTION

I. Introduction

Figure 1:
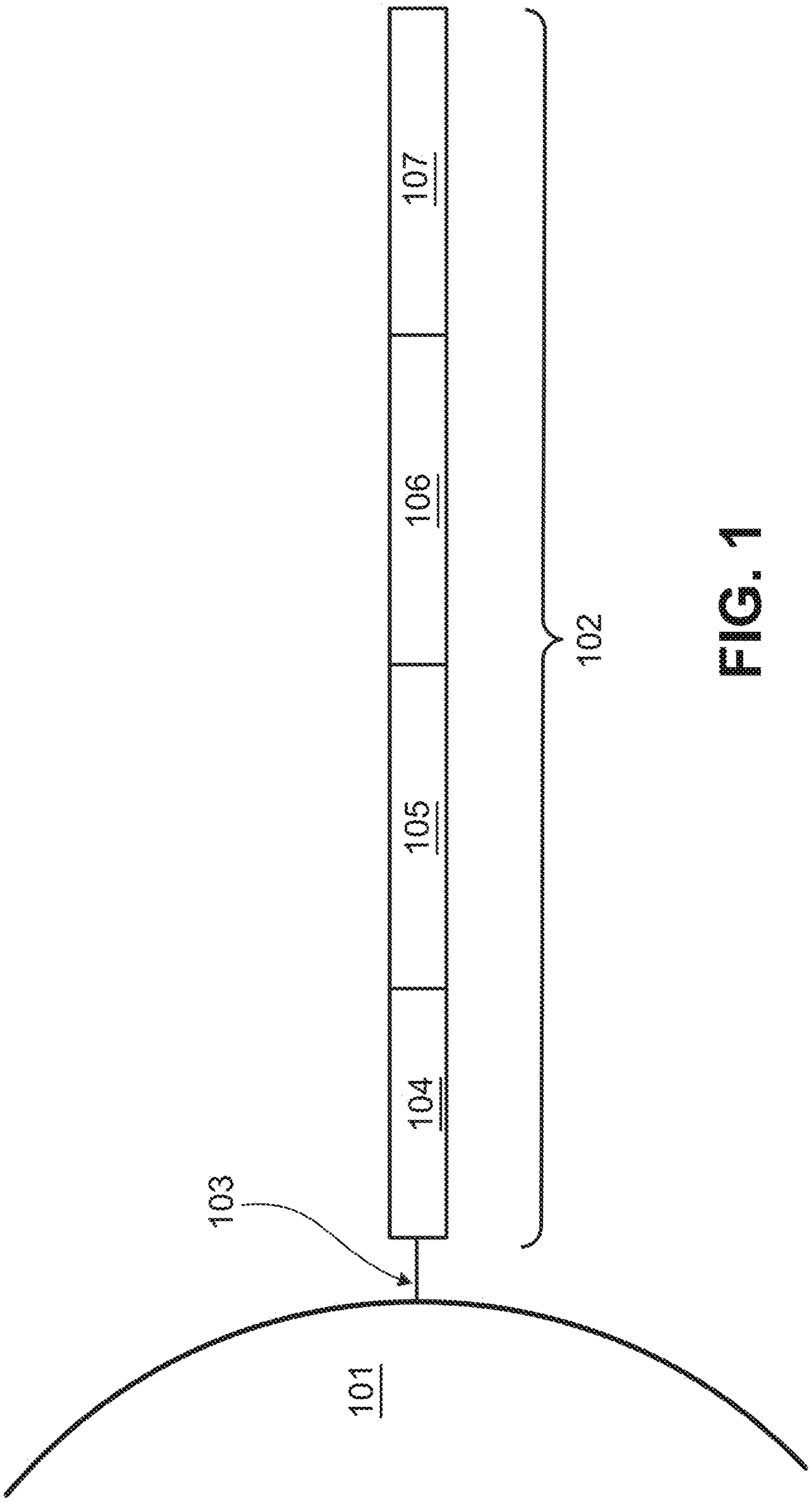
FIG. 1 is a schematic diagram showing an example of a barcoded capture probe, as described herein.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodriques et al., Science 363 (6434):1463-1467, 2019; Lee et al., Nat. Protoc. 10 (3):442-458, 2015; Trejo et al., PLOS ONE 14 (2):e0212031, 2019; Chen et al., Science 348 (6233): aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a connected probe (e.g., a ligation product) or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)).

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that are useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte.

In some embodiments, the capture probe comprises one or more additional functional sequences that can be located, for example between the spatial barcode 105 and the UMI sequence 106, between the UMI sequence 106 and the capture domain 107, or following the capture domain 107. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 is common to all of the probes attached to a given feature. In some embodiments, the UMI sequence 106 of a capture probe attached to a given feature is different from the UMI sequence of a different capture probe attached to the given feature.

Figure 2:
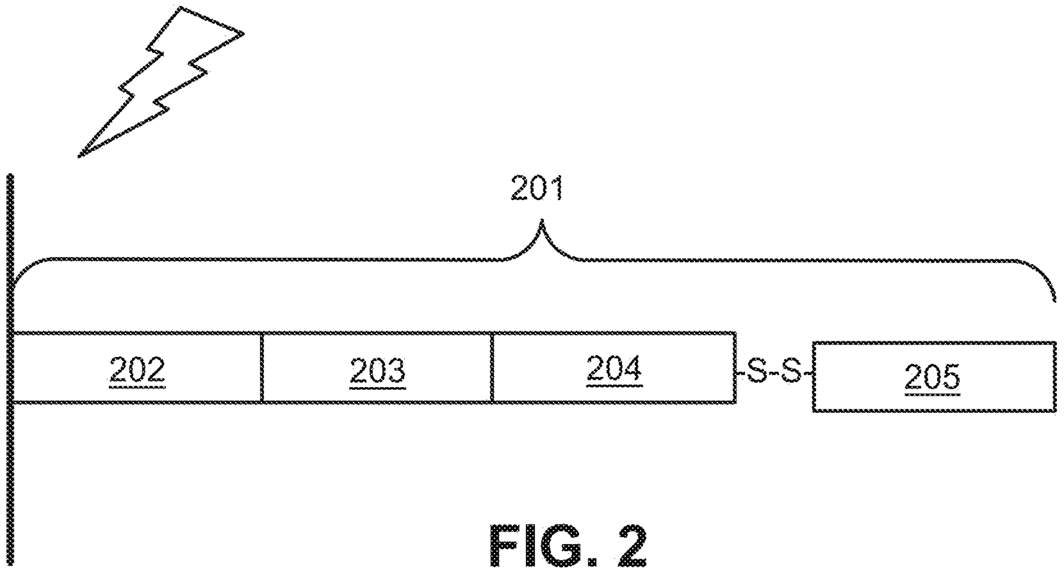
FIG. 2 is a schematic illustrating a cleavable capture probe, wherein the cleaved capture probe can enter into a non-permeabilized cell and bind to target analytes within the sample.

FIG. 2 is a schematic illustrating a cleavable capture probe, wherein the cleaved capture probe can enter into a non-permeabilized cell and bind to analytes within the sample. The capture probe 201 contains a cleavage domain 202, a cell penetrating peptide 203, a reporter molecule 204, and a disulfide bond (—S—S—). 205 represents all other parts of a capture probe, for example a spatial barcode and a capture domain.

Figure 3:
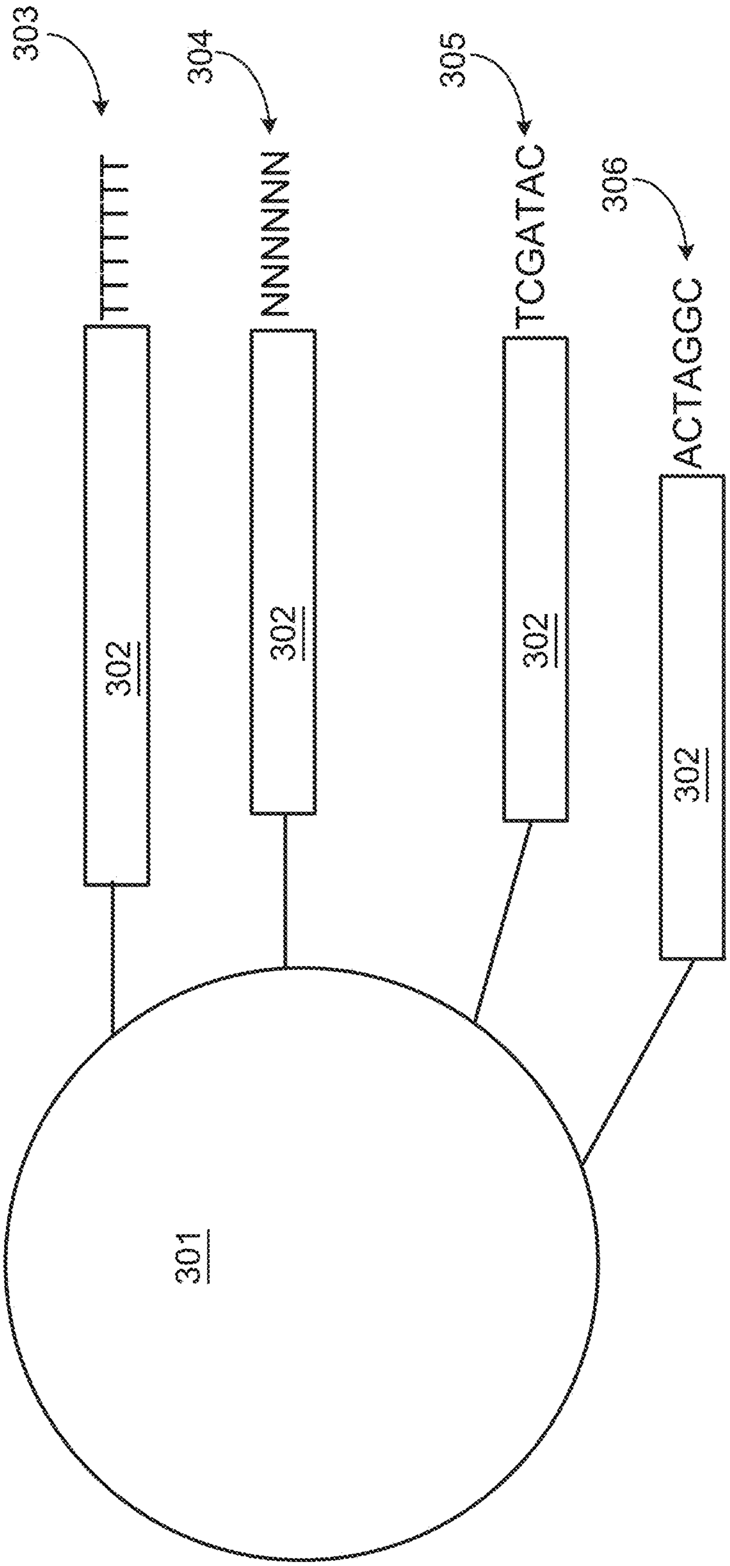
FIG. 3 is a schematic diagram of an exemplary multiplexed spatially-barcoded feature.

FIG. 3 is a schematic diagram of an exemplary multiplexed spatially-barcoded feature. In FIG. 3, the feature 301 can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may be coupled to four different types of spatially-barcoded capture probes, each type of spatially-barcoded capture probe possessing the spatial barcode 302. One type of capture probe associated with the feature includes the spatial barcode 302 in combination with a poly(T) capture domain 303, designed to capture mRNA target analytes. A second type of capture probe associated with the feature includes the spatial barcode 302 in combination with a random N-mer capture domain 304 for gDNA analysis. A third type of capture probe associated with the feature includes the spatial barcode 302 in combination with a capture domain complementary to a capture handle sequence of an analyte capture agent of interest 305. A fourth type of capture probe associated with the feature includes the spatial barcode 302 in combination with a capture domain that can specifically bind a nucleic acid molecule 306 that can function in a CRISPR assay (e.g., CRISPR/Cas9). While only four different capture probe-barcoded constructs are shown in FIG. 3, capture-probe barcoded constructs can be tailored for analyses of any given analyte associated with a nucleic acid and capable of binding with such a construct. For example, the schemes shown in FIG. 3 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MHC multimers described herein), and a V (D) J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents. See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) a capture handle sequence (e.g., an analyte capture sequence). As used herein, the term "analyte binding moiety barcode" refers to a barcode that is associated with or otherwise identifies the analyte binding moiety. As used herein, the term "analyte capture sequence" or "capture handle sequence" refers to a region or moiety configured to hybridize to, bind to, couple to, or otherwise interact with a capture domain of a capture probe. In some embodiments, a capture handle sequence is complementary to a capture domain of a capture probe. In some cases, an analyte binding moiety barcode (or portion thereof) may be able to be removed (e.g., cleaved) from the analyte capture agent.

Figure 4:
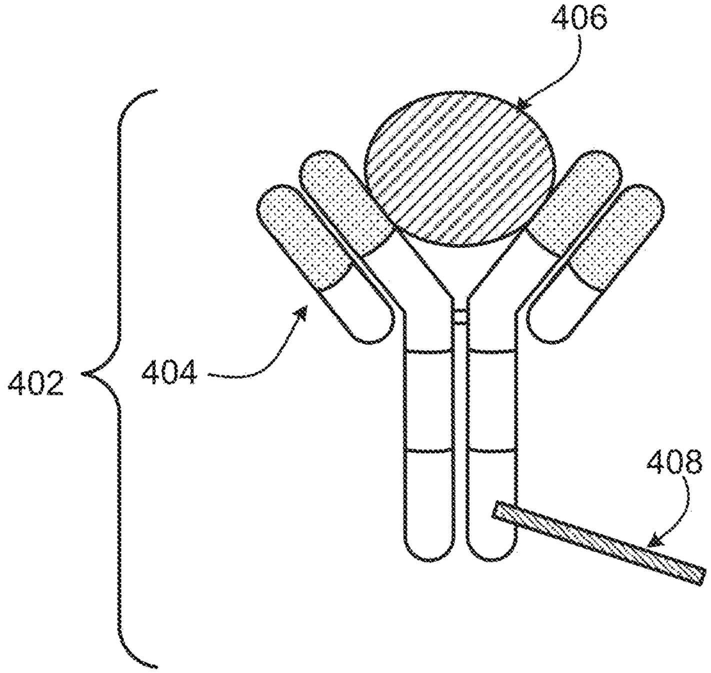
FIG. 4 is a schematic diagram of an exemplary analyte capture agent.

FIG. 4 is a schematic diagram of an exemplary analyte capture agent 402 comprised of an analyte-binding moiety 404 and an analyte binding moiety barcode domain 408. The exemplary analyte-binding moiety 404 is a molecule capable of binding to an analyte 406 and the analyte capture agent is capable of interacting with a spatially-barcoded capture probe. The analyte-binding moiety can bind to the analyte 406 with high affinity and/or with high specificity. The analyte capture agent can include an analyte binding moiety barcode domain 408, a nucleotide sequence (e.g., an oligonucleotide), which can hybridize to at least a portion or an entirety of a capture domain of a capture probe. The analyte binding moiety barcode domain 408 can comprise an analyte binding moiety barcode and a capture handle sequence described herein. The analyte-binding moiety 404 can include a polypeptide and/or an aptamer. The analyte-binding moiety 404 can include an antibody or antibody fragment (e.g., an antigen-binding fragment).

Figure 5:
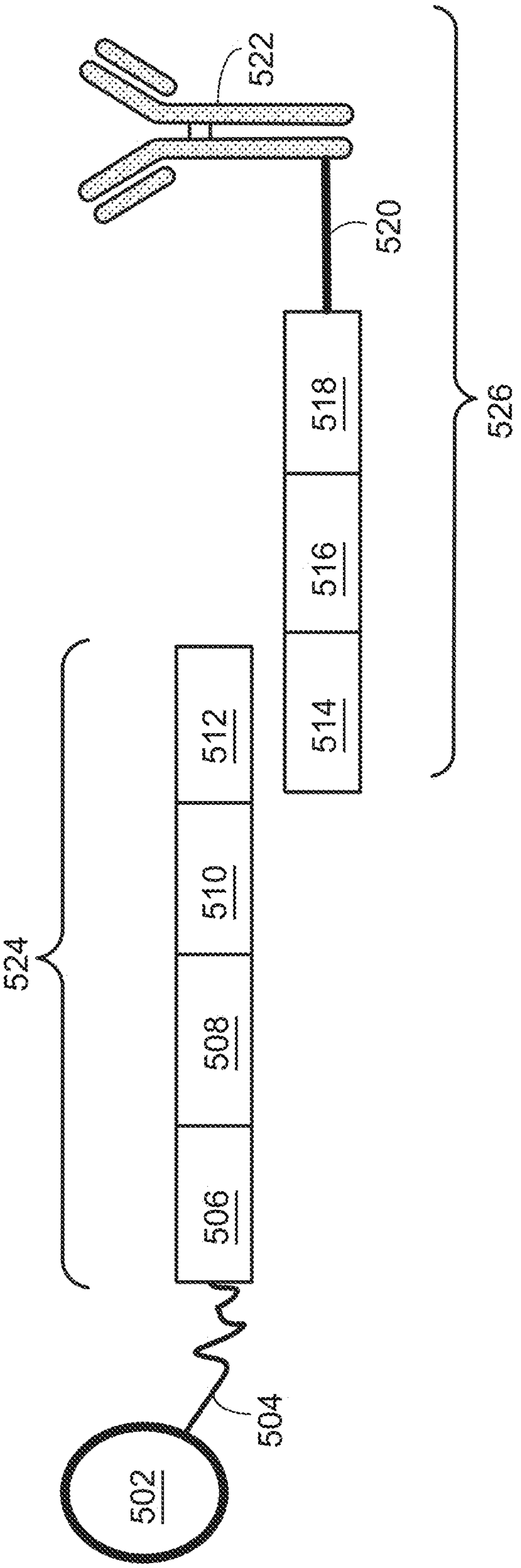
FIG. 5 is a schematic diagram depicting an exemplary interaction between a feature-immobilized capture probe 524 and an analyte capture agent 526.

FIG. 5 is a schematic diagram depicting an exemplary interaction between a feature-immobilized capture probe 524 and an analyte capture agent 526. The feature-immobilized capture probe 524 can include a spatial barcode 508 as well as functional sequences 506 and UMI 510, as described elsewhere herein. The capture probe can also include a capture domain 512 that is capable of binding to an analyte capture agent 526. The analyte capture agent 526 can include a functional sequence 518, analyte binding moiety barcode 516, and a capture handle sequence 514 that is capable of binding to the capture domain 512 of the capture probe 524. The analyte capture agent can also include a linker 520 that allows the capture agent barcode domain 516 to couple to the analyte binding moiety 522.

Figure 6A:
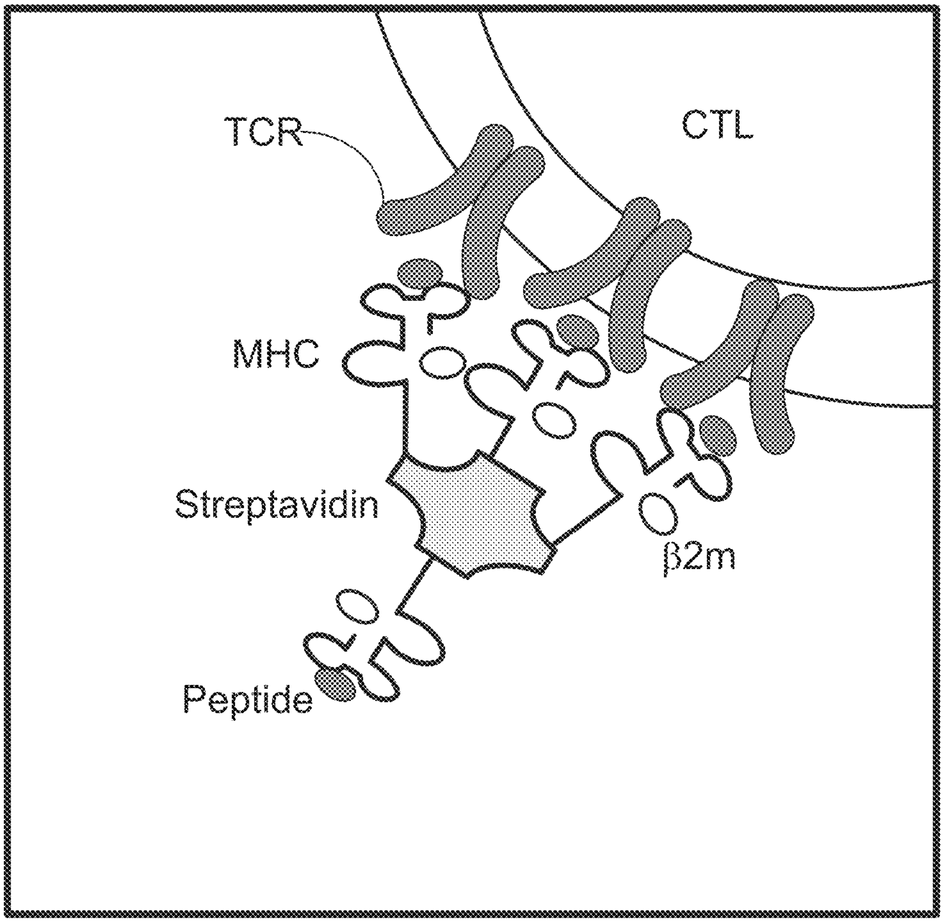
FIGS. 6A-6C are schematics illustrating how streptavidin cell tags can be utilized in an array-based system to produce a spatially-barcoded cells or cellular contents.
Figure 6B:
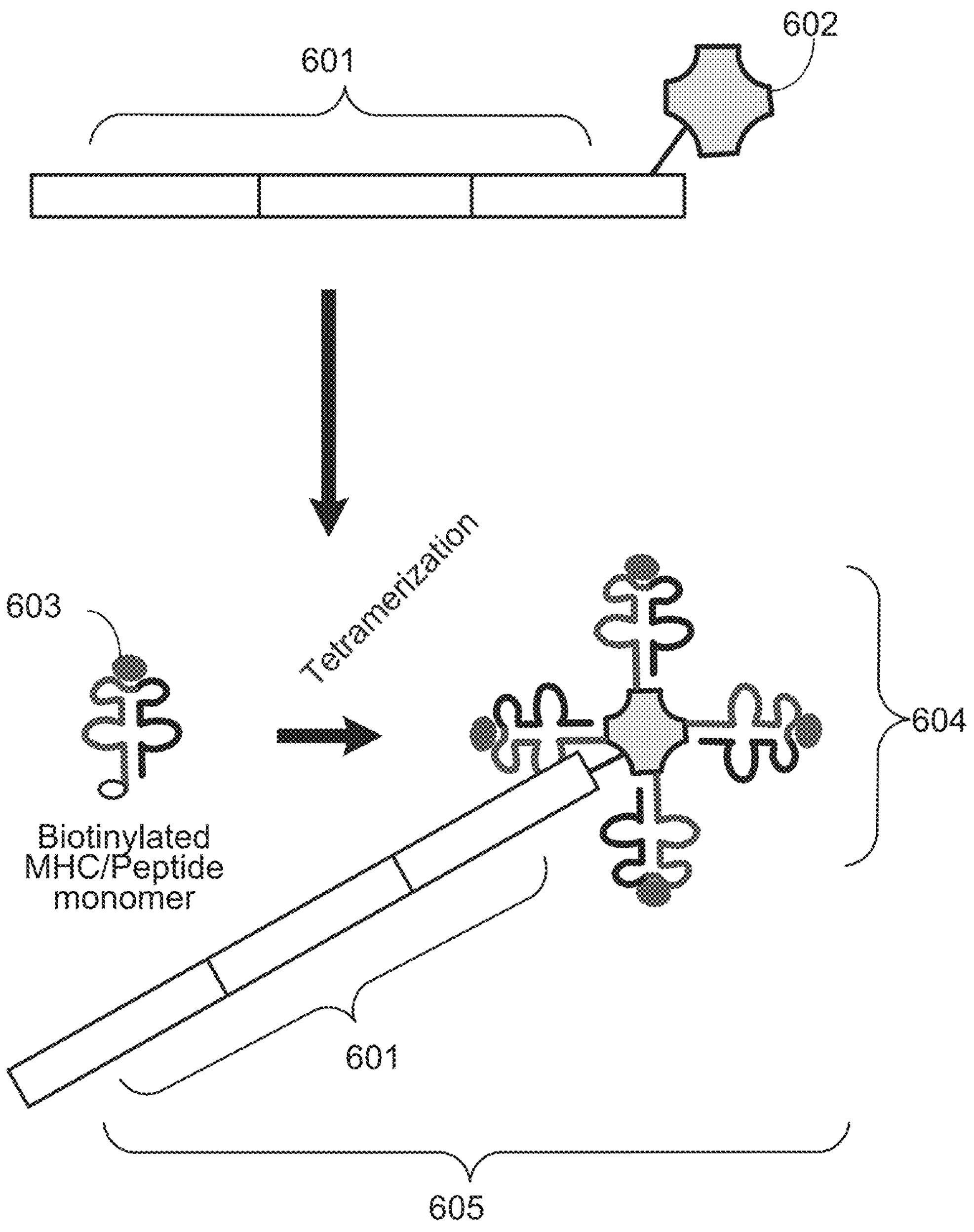
Figure 6C:
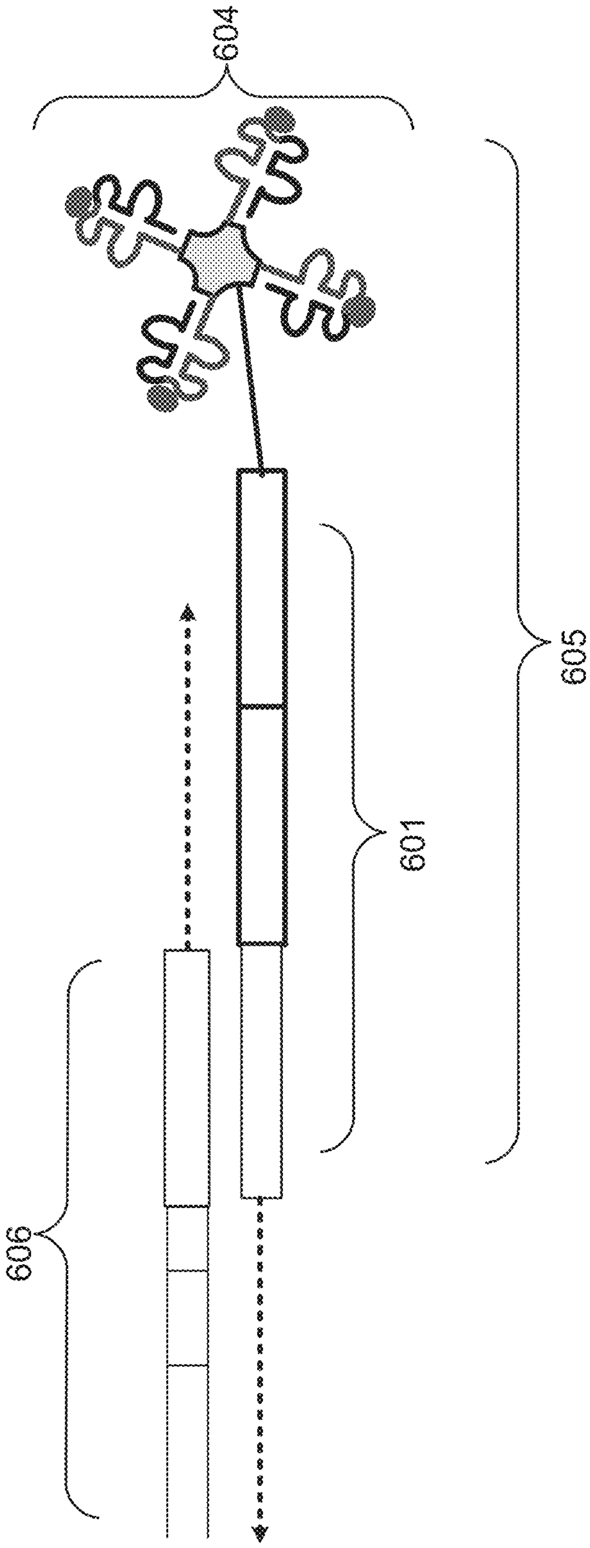

FIGS. 6A, 6B, and 6C are schematics illustrating how streptavidin cell tags can be utilized in an array-based system to produce a spatially-barcoded cell or cellular contents. For example, as shown in FIG. 6A, peptide-bound major histocompatibility complex (MHC) can be individually associated with biotin (β2m) and bound to a streptavidin moiety such that the streptavidin moiety comprises multiple pMHC moieties. Each of these moieties can bind to a TCR such that the streptavidin binds to a target T-cell via multiple MCH/TCR binding interactions. Multiple interactions synergize and can substantially improve binding affinity. Such improved affinity can improve labelling of T-cells and also reduce the likelihood that labels will dissociate from T-cell surfaces. As shown in FIG. 6B, a capture agent barcode domain 601 can be modified with streptavidin 602 and contacted with multiple molecules of biotinylated MHC 603 such that the biotinylated MHC 603 molecules are coupled with the streptavidin conjugated capture agent barcode domain 601. The result is a barcoded MHC multimer complex 605. As shown in FIG. 6B, the capture agent barcode domain sequence 601 can identify the MHC as its associated label and also includes optional functional sequences such as sequences for hybridization with other oligonucleotides. As shown in FIG. 6C, one example oligonucleotide is capture probe 606 that comprises a complementary sequence (e.g., rGrGrG corresponding to C C C), a barcode sequence and other functional sequences, such as, for example, a UMI, an adapter sequence (e.g., comprising a sequencing primer sequence (e.g., R1 or a partial R1 ("pR1"), R2), a flow cell attachment sequence (e.g., P5 or P7 or partial sequences thereof)), etc. In some cases, capture probe 606 may at first be associated with a feature (e.g., a gel bead) and released from the feature. In other embodiments, capture probe 606 can hybridize with a capture agent barcode domain 601 of the MHC-oligonucleotide complex 605. The hybridized oligonucleotides (Spacer C C C and Spacer rGrGrG) can then be extended in primer extension reactions such that constructs comprising sequences that correspond to each of the two spatial barcode sequences (the spatial barcode associated with the capture probe, and the barcode associated with the MHC-oligonucleotide complex) are generated. In some cases, one or both of these corresponding sequences may be a complement of the original sequence in capture probe 606 or capture agent barcode domain 601. In other embodiments, the capture probe and the capture agent barcode domain are ligated together. The resulting constructs can be optionally further processed (e.g., to add any additional sequences and/or for clean-up) and subjected to sequencing. As described elsewhere herein, a sequence derived from the capture probe 606 spatial barcode sequence may be used to identify a feature and the sequence derived from spatial barcode sequence on the capture agent barcode domain 601 may be used to identify the particular peptide MHC complex 604 bound on the surface of the cell (e.g., when using MHC-peptide libraries for screening immune cells or immune cell populations).

Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a connected probe (e.g., a ligation product) or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form a connected probe (e.g., a ligation product) with a template (e.g., a DNA or RNA template, such as an analyte or an intermediate agent, or portion thereof), thereby creating ligation products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their colocalization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45 (14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly (A) sequence, a non-homopolymeric sequence). After hybridization to the analyte, a ligase (e.g., SplintR ligase) ligates the two oligonucleotides together, creating a connected probe (e.g., a ligation product). In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the connected probe (e.g., a ligation product) is released from the analyte. In some instances, the connected probe (e.g., a ligation product) is released using an endonuclease (e.g., RNAse H). The released connected probe (e.g., a ligation product) can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), the Targeted Gene Expression-Spatial User Guide (e.g., Rev A, dated October 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e) (ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

The sandwich process is described in PCT Patent Application Publication No. WO 2020/123320, which is incorporated by reference in its entirety.

II. Targeted Spatial Gene Expression Profiling by Hybridization and Capture of Spatial cDNA (a) Introduction Spatial analysis methods using capture probes and/or analyte capture agents provide information regarding the abundance and location of an analyte (e.g., a nucleic acid or protein). Traditionally, the sequencing result contains unwanted genes, ribosomal or mitochondrial transcripts, and other reads that are not of interest. Detection of the analytes of interest largely depends, at least in part, on the sequencing capacity of all captured analytes on the array. Disclosed herein are methods and compositions for capturing target analytes of interest using bait oligonucleotides that are specific to the target analytes of interest. In this way, the sequencing result contains a higher percentage of reads from the target analytes of interest, which increases the spatial resolution and sequencing cost of the target analytes of interest.

Disclosed herein are methods of capturing target analytes of interest using bait oligonucleotides that are specific to the target analytes of interest. As disclosed herein, bait oligonucleotides are short (40 bp to 160 bp) oligonucleotides that hybridize to transcribed (e.g., mRNA) sequences in order to detect the mRNA, and the expression thereof. It has been identified that bait oligonucleotides can hybridize to the 5' end of a transcript, the 3' end of the transcript, or any intervening sequence of the transcript. In particular, designing probes to hybridize to an intervening sequence of a transcript (i.e., not the 5' end and not the 3' end) has certain advantages. For example, many transcripts in the human genome have varying sequences at the 5' and 3' end. Thus, designing baits that would target intervening transcript sequences, and particularly conserved sequences, could allow a single bait to hybridize to multiple isoforms of the same gene. Thus, disclosed herein are compositions and methods that comprise bait oligonucleotides that hybridize to multiple isoforms of the same gene.

Accordingly, provided herein are methods that comprise designing and using probes (e.g., bait oligonucleotides, nucleic acid baits, and the like) to capture full-length (e.g., unfragmented) cDNA for sequencing analysis, rather than bait oligonucleotides for capturing final library fragments encompassing 3' UTRs. By targeting full-length cDNA, it is possible to utilize the more reliably annotated regions of the target gene, such as coding sequences, for each transcript (e.g., isoform) of the respective gene. Accordingly, steps for identifying a target of interest in a sample using this method include, but are not limited to, preparation of a nucleic acid library so that nucleic acid baits can hybridize to one or more target analytes; hybridization of the nucleic acid baits to the one or more target analytes; and determining the location and abundance of the target analyte in the biological sample.

Also featured herein are methods of detecting analytes of interest that have been captured by a capture probe on a substrate (i.e., a spatial array). In some instances, target analytes of interest are identified using probes (e.g., nucleic acid baits) after the analytes of interest are captured on a spatial array. Thus, steps for identifying a target of interest in a sample using this method include, but are not limited to, capture of an analyte in a sample using a capture probe; amplification of the hybridized capture probe/analyte product to create a cDNA library; preparation of the cDNA library in order that nucleic acid baits can hybridize to one or more target analytes; hybridization of the nucleic acid baits to the one or more target analytes; and determining the location and abundance of the target analyte in the biological sample.

Profiling the phenotype of a biological sample using either of the methods described above and as further elucidated herein helps to avoid confounding biological factors, such as detection of strongly expressed genes that are not relevant to a study or cell-cycle phenotypes that could mask biological variance. In addition, enhancing detection of one or more target analytes helps to dramatically reduce sequencing cost to obtain information from a panel of genes of interest, by minimizing the number of reads spent on non-panel genes (e.g., ribosomal protein transcripts, mitochondrial transcripts, etc.). As such, the methods described herein are further cost effective.

(b) Biological Samples, Analytes, and Preparation of the Same (i) Biological Samples and Analytes In some embodiments, the biological sample used in the methods disclosed herein is a cell culture sample. In some instances, the biological sample is a tissue sample. In some embodiments, the biological sample is a section of a tissue sample. In some embodiments, the biological sample is a fresh tissue sample. In some embodiments, the biological sample is a fresh-frozen tissue sample. In some embodiments, the biological sample is a tissue sample that has been formalin-fixed and paraffin-embedded (FFPE) (i.e., an FFPE sample). In some embodiments, the biological sample is a tissue sample embedded in optimal cutting temperature (OCT) compound. In some embodiments, the biological sample has been previously stained (e.g., immunohistochemistry (IHC) or histological staining) and imaged, and optionally, destained.

In some instances, a biological sample is obtained from the subject for analysis using any of a variety of techniques including, but not limited to, biopsy, surgery, and laser capture microscopy (LCM), and generally includes cells and/or other biological material from the subject. A biological sample can also be obtained from a prokaryote such as a bacterium, e.g., *Escherichia coli*, Staphylococci or *Mycoplasma pneumoniae*; an Archaea; a virus such as Hepatitis C virus or human immunodeficiency virus; or a viroid. A biological sample can also be obtained from a eukaryote, such as a patient derived organoid (PDO) or patient derived xenograft (PDX) for example. Biological samples can be from mammals, such as humans, non-human mammals (e.g., mice), etc. Subjects from which biological samples can be obtained can be healthy or asymptomatic individuals, individuals that have or are suspected of having a disease (e.g., a patient with a disease such as cancer) or a pre-disposition to a disease, and/or individuals that are in need of therapy or suspected of needing therapy.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions.

Biological samples can be derived from a homogeneous culture or population of the subjects or organisms mentioned herein or alternatively from a collection of several different organisms, for example, in a community or ecosystem. In some embodiments, the biological sample is a human sample.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells.

Biological samples can also include fetal cells. For example, a procedure such as amniocentesis can be performed to obtain a fetal cell sample from maternal circulation. Sequencing of fetal cells can be used to identify any of a number of genetic disorders, including, e.g., aneuploidy such as Down's syndrome, Edwards syndrome, and Patau syndrome. Further, cell surface features of fetal cells can be used to identify any of a number of disorders or diseases.

Biological samples can also include immune cells. Sequence analysis of the immune repertoire of such cells, including genomic, proteomic, and cell surface features, can provide a wealth of information to facilitate an understanding in the status and function of the immune system. By way of example, determining the status (e.g., negative or positive) of minimal residue disease (MRD) in a multiple myeloma (MM) patient following autologous stem cell transplantation is considered a predictor of MRD in the MM patient (see, e.g., U.S. Patent Application Publication No. 2018/0156784, the entire contents of which are incorporated herein by reference).

Examples of immune cells in a biological sample include, but are not limited to, B cells, T cells (e.g., cytotoxic T cells, natural killer T cells, regulatory T cells, and T helper cells), natural killer cells, cytokine induced killer (CIK) cells, myeloid cells, such as granulocytes (basophil granulocytes, eosinophil granulocytes, neutrophil granulocytes/hypersegmented neutrophils), monocytes/macrophages, mast cells, thrombocytes/megakaryocytes, and dendritic cells.

In some embodiments, the biological sample is affixed to a slide. In some embodiments, the sample is stained prior to creation of the library of nucleic acids (e.g., plurality of nucleic acids). In some embodiments, the biological sample is stained while the biological sample is on the slide. In some embodiments, the stained biological sample is imaged prior to creation of the library of nucleic acids (e.g., plurality of nucleic acids).

In some embodiments, staining includes biological staining techniques such as H&E staining. In some embodiments, staining includes identifying analytes using fluorescently conjugated antibodies (e.g., immunofluorescence). In some embodiments, a biological sample is stained using two or more different types of stains, or two or more different staining techniques (e.g., IF, IHC, and/or H&E staining). For example, a biological sample can be prepared by staining and imaging using one technique (e.g., H&E staining and bright field imaging), destained (e.g., quenching or photobleaching), followed by staining and imaging using another technique (e.g., IHC/IF staining and fluorescence microscopy) for the same biological sample.

In some embodiments, biological samples can be destained prior to creation of the spatial library of nucleic acids. Methods of destaining or discoloring a biological sample are known in the art, and generally depend on the nature of the stain(s) applied to the biological sample.

In some embodiments, the analyte in the biological sample is a nucleic acid. In some embodiments, the analyte (e.g., nucleic acid) is obtained from the biological sample. In some embodiments, the nucleic acid is DNA (e.g., genomic DNA, mitochondrial DNA, or exosomal DNA). In some embodiments, the nucleic acid is RNA. In some embodiments, the RNA is mRNA. Additional examples of RNA such as various types of coding and non-coding RNA. Examples of the different types of RNA analytes include messenger RNA (mRNA), ribosomal RNA (rRNA), transfer RNA (tRNA), microRNA (miRNA), and viral RNA. The RNA can be a transcript (e.g., present in a tissue section). The RNA can be small (e.g., less than 200 nucleic acid bases in length) or large (e.g., RNA greater than 200 nucleic acid bases in length). Small RNAs mainly include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments, the nucleic acid comprises DNA. Examples of DNA include genomic DNA, methylated DNA, specific methylated DNA sequences, fragmented DNA, mitochondrial DNA, in situ synthesized PCR products, and RNA/DNA hybrids.

(ii) Imaging and Staining

In some instances, biological samples can be stained using a wide variety of stains and staining techniques. In some instances, the biological sample is a section of a tissue (e.g., a 10 μm section). In some instances, the biological sample is dried after placement onto a glass slide. In some instances, the biological sample is dried at 42° C. In some instances, drying occurs for about 1 hour, about 2, hours, about 3 hours, or until the sections become transparent. In some instances, the biological sample can be dried overnight (e.g., in a desiccator at room temperature).

In some embodiments, a sample can be stained using any number of biological stains, including but not limited to, acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, or safranin. In some instances, the methods disclosed herein include imaging the biological sample. In some instances, imaging the sample occurs prior to deaminating the biological sample. In some instances, the sample can be stained using known staining techniques, including Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation. In some instances, the stain is an H&E stain.

In some embodiments, the biological sample can be stained using a detectable label (e.g., radioisotopes, fluorophores, chemiluminescent compounds, bioluminescent compounds, and dyes) as described elsewhere herein. In some embodiments, a biological sample is stained using only one type of stain or one technique. In some embodiments, staining includes biological staining techniques such as H&E staining. In some embodiments, staining includes identifying analytes using fluorescently-conjugated antibodies. In some embodiments, a biological sample is stained using two or more different types of stains, or two or more different staining techniques. For example, a biological sample can be prepared by staining and imaging using one technique (e.g., H&E staining and brightfield imaging), followed by staining and imaging using another technique (e.g., IHC/IF staining and fluorescence microscopy) for the same biological sample.

In some embodiments, biological samples can be destained. Methods of destaining or decoloring a biological sample are known in the art, and generally depend on the nature of the stain(s) applied to the sample. For example, H&E staining can be destained by washing the sample in HCl, or any other acid (e.g., selenic acid, sulfuric acid, hydroiodic acid, benzoic acid, carbonic acid, malic acid, phosphoric acid, oxalic acid, succinic acid, salicylic acid, tartaric acid, sulfurous acid, trichloroacetic acid, hydrobromic acid, hydrochloric acid, nitric acid, orthophosphoric acid, arsenic acid, selenous acid, chromic acid, citric acid, hydrofluoric acid, nitrous acid, isocyanic acid, formic acid, hydrogen selenide, molybdic acid, lactic acid, acetic acid, carbonic acid, hydrogen sulfide, or combinations thereof). In some embodiments, destaining can include 1, 2, 3, 4, 5, or more washes in an acid (e.g., HCl). In some embodiments, destaining can include adding HCl to a downstream solution (e.g., permeabilization solution). In some embodiments, destaining can include dissolving an enzyme used in the disclosed methods (e.g., pepsin) in an acid (e.g., HCl) solution. In some embodiments, after destaining hematoxylin with an acid, other reagents can be added to the destaining solution to raise the pH for use in other applications. For example, SDS can be added to an acid destaining solution in order to raise the pH as compared to the acid destaining solution alone. As another example, in some embodiments, one or more immunofluorescence stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., J. Histochem. Cytochem. 2017; 65 (8): 431-444, Lin et al., Nat Commun. 2015; 6:8390, Pirici et al., J. Histochem. Cytochem. 2009; 57:567-75, and Glass et al., J. Histochem. Cytochem. 2009; 57:899-905, the entire contents of each of which are incorporated herein by reference.

In some embodiments, immunofluorescence or immunohistochemistry protocols (direct and indirect staining techniques) can be performed as a part of, or in addition to, the exemplary spatial workflows presented herein. For example, tissue sections can be fixed according to methods described herein. The biological sample can be transferred to an array (e.g., capture probe array), wherein analytes (e.g., proteins) are probed using immunofluorescence protocols. For example, the sample can be rehydrated, blocked, and permeabilized (3×SSC, 2% BSA, 0.1% Triton X, 1 U/μl RNAse inhibitor for 10 minutes at 4° C.) before being stained with fluorescent primary antibodies (1:100 in 3×SSC, 2% BSA, 0.1% Triton X, 1 U/μl RNAse inhibitor for 30 minutes at 4° C.). The biological sample can be washed, coverslipped (in glycerol+1 U/μl RNAse inhibitor), imaged (e.g., using a confocal microscope or other apparatus capable of fluorescent detection), washed, and processed according to analyte capture or spatial workflows described herein.

In some instances, a glycerol solution and a cover slip can be added to the sample. In some instances, the glycerol solution can include a counterstain (e.g., DAPI).

As used herein, an antigen retrieval buffer can improve antibody capture in IF/IHC protocols. An exemplary protocol for antigen retrieval can be preheating the antigen retrieval buffer (e.g., to 95° C.), immersing the biological sample in the heated antigen retrieval buffer for a predetermined time, and then removing the biological sample from the antigen retrieval buffer and washing the biological sample.

In some embodiments, optimizing permeabilization can be useful for identifying intracellular analytes. Permeabilization optimization can include selection of permeabilization agents, concentration of permeabilization agents, and permeabilization duration. Tissue permeabilization is discussed elsewhere herein.

In some embodiments, blocking an array and/or a biological sample in preparation of labeling the biological sample decreases nonspecific binding of the antibodies to the array and/or biological sample (decreases background). Some embodiments provide for blocking buffers/blocking solutions that can be applied before and/or during application of the label, wherein the blocking buffer can include a blocking agent, and optionally a surfactant and/or a salt solution. In some embodiments, a blocking agent can be bovine serum albumin (BSA), serum, gelatin (e.g., fish gelatin), milk (e.g., non-fat dry milk), casein, polyethylene glycol (PEG), polyvinyl alcohol (PVA), or polyvinylpyrrolidone (PVP), biotin blocking reagent, a peroxidase blocking reagent, levamisole, Carnoy's solution, glycine, lysine, sodium borohydride, pontamine sky blue, Sudan Black, trypan blue, FITC blocking agent, and/or acetic acid. The blocking buffer/blocking solution can be applied to the array and/or biological sample prior to and/or during labeling (e.g., application of fluorophore-conjugated antibodies) to the biological sample.

(iii) Preparation of Sample for Application of Probes

In some instances, the biological sample is deparaffinized. Deparaffinization can be achieved using any method known in the art. For example, in some instances, the biological sample is treated with a series of washes that include xylene and various concentrations of ethanol. In some instances, methods of deparaffinization include treatment with xylene (e.g., three washes at 5 minutes each). In some instances, the methods further include treatment with ethanol (e.g., 100% ethanol, two washes 10 minutes each; 95% ethanol, two washes 10 minutes each; 70% ethanol, two washes 10 minutes each; 50% ethanol, two washes 10 minutes each). In some instances, after ethanol washes, the biological sample can be washed with deionized water (e.g., two washes for 5 minutes each). It is appreciated that one skilled in the art can adjust these methods to optimize deparaffinization.

In some instances, the biological sample is decrosslinked. In some instances, the biological sample is decrosslinked in a solution containing TE buffer (comprising Tris and EDTA). In some instances, the TE buffer is basic (e.g., at a pH of about 9). In some instances, decrosslinking occurs at about 50° C. to about 80° C. In some instances, decrosslinking occurs at about 70° C. In some instances, decrosslinking occurs for about 1 hour at 70° C. Just prior to decrosslinking, the biological sample can be treated with an acid (e.g., 0.1M HCl for about 1 minute). After the decrosslinking step, the biological sample can be washed (e.g., with 1×PBST).

In some instances, the methods of preparing a biological sample for probe application include permeabilizing the sample. In some instances, the biological sample is permeabilized using a phosphate buffer. In some instances, the phosphate buffer is PBS (e.g., 1×PBS). In some instances, the phosphate buffer is PBST (e.g., 1×PBST). In some instances, the permeabilization step is performed multiple times (e.g., 3 times at 5 minutes each).

In some instances, the methods of preparing a biological sample for probe application include steps of equilibrating and blocking the biological sample. In some instances, equilibrating is performed using a pre-hybridization (pre-Hyb) buffer. In some instances, the pre-Hyb buffer is RNase-free. In some instances, the pre-Hyb buffer contains no bovine serum albumin (BSA), solutions like Denhardt's, or other potentially nuclease-contaminated biological materials.

In some instances, the equilibrating step is performed multiple times (e.g., 2 times at 5 minutes each; 3 times at 5 minutes each). In some instances, the biological sample is blocked with a blocking buffer. In some instances, the blocking buffer includes a carrier such as tRNA, for example yeast tRNA such as from brewer's yeast (e.g., at a final concentration of 10-20 μg/mL). In some instances, blocking can be performed for 5, 10, 15, 20, 25, or 30 minutes.

Any of the foregoing steps can be optimized for performance. For example, one can vary the temperature. In some instances, the pre-hybridization methods are performed at room temperature. In some instances, the pre-hybridization methods are performed at 4° C. (in some instances, varying the timeframes provided herein).

(c) Nucleic Acid Library Preparation (i) Single Cell Library Preparation

Disclosed herein are methods of preparing a library of nucleic acids (e.g., a plurality of nucleic acids) from a cell or population of cells. In some embodiments, the biological sample can be derived from a cell culture grown in vitro. Samples derived from a cell culture can include one or more suspension cells which are anchorage-independent within the cell culture. Examples of such cells include, but are not limited to, cell lines derived from hematopoietic cells, and from the following cell lines: Colo205, CCRF-CEM, HL-60, K562, MOLT-4, RPMI-8226, SR, HOP-92, NCI-H322M, and MALME-3M.

Samples derived from a cell culture can include one or more adherent cells which grow on the surface of the vessel that contains the culture medium. Non-limiting examples of adherent cells include DU145 (prostate cancer) cells, H295R (adrenocortical cancer) cells, HeLa (cervical cancer) cells, KBM-7 (chronic myelogenous leukemia) cells, LNCaP (prostate cancer) cells, MCF-7 (breast cancer) cells, MDA-MB-468 (breast cancer) cells, PC3 (prostate cancer) cells, SaOS-2 (bone cancer) cells, SH-SY5Y (neuroblastoma, cloned from a myeloma) cells, T-47D (breast cancer) cells, THP-1 (acute myeloid leukemia) cells, U87 (glioblastoma) cells, National Cancer Institute's 60 cancer cell line panel (NCI60), vero (African green monkey Chlorocebus kidney epithelial cell line) cells, MC3T3 (embryonic calvarium) cells, GH3 (pituitary tumor) cells, PC12 (pheochromocytoma) cells, dog MDCK kidney epithelial cells, *Xenopus* A6 kidney epithelial cells, zebrafish AB9 cells, and Sf9 insect epithelial cells.

Additional examples of samples considered as a cell or population of cells include, without limitation, those listed in Table 1 in priority documents U.S. Provisional Patent Application Nos. 62/979,652; 62/980,124; and 63/077,019, each of which is incorporated by reference in its entirety. It is appreciated that a cell population used in single-cell library preparation can be from any of the cells or cell culture populations disclosed herein.

In some embodiments, the library of nucleic acids (e.g., a plurality of nucleic acids) include one or more nucleic acids of interest, whose detection can be enhanced using hybridization methods. Analytes can be isolated, amplified, and/or otherwise processed for subsequent analysis, such as fragmentation and sequencing library preparation.

In some embodiments, the biological sample is permeabilized using any method described herein. A biological sample is permeabilized to allow analytes to be released from one or more cells within the biological sample. In some embodiments, obtaining the pool of analytes (e.g., mRNA) from the biological sample comprises any method of nucleic acid extraction and/or isolation known in the art and/or described herein. In some embodiments, analytes released and obtained from the one or more cells can be amplified. In some embodiments, the pool of poly-adenylated mRNA is obtained from the biological sample in preparation for a sequencing method (e.g., by any method encompassed in a sequencing library preparation workflow).

Additional reagents can be added to a biological sample to perform various functions prior to analysis of the sample. In some embodiments, DNase and RNase inactivating agents or inhibitors, and/or chelating agents such as EDTA, can be added to the sample. In some embodiments, the sample can be treated with one or more enzymes. For example, one or more endonucleases to fragment DNA or RNA, and DNA polymerase enzymes, used to amplify nucleic acids can be added. Enzymes that can be added to the sample include, but are not limited to, polymerases, transposases, ligases, DNAses, and RNAses.

In some embodiments, reverse transcriptase enzymes can be added to the sample, including enzymes with terminal transferase activity, primers, and switch oligonucleotides. Template switching can be used to increase the length of a cDNA, e.g., by appending a predefined nucleic acid sequence to the cDNA from which nucleic acid extension can proceed.

In some embodiments, obtaining the plurality of cDNA sequences comprises performing first-strand cDNA synthesis via reverse transcription of the corresponding pool of analytes (e.g., poly-adenylated mRNA). In some such embodiments, the cDNA is generated using a poly (T) containing primer. In some embodiments, the generated cDNA is barcoded using a capture probe, featuring a barcode sequence (and optionally, a UMI sequence) that hybridizes with at least a portion of the generated cDNA. In some embodiments, the generated cDNA is appended with a unique molecular identifier (UMI) using a capture probe featuring a UMI that hybridizes with at least a portion of the generated cDNA. In some embodiments, a template switching oligonucleotide hybridizes to a poly (C) tail added to a 3' end of the cDNA by a reverse transcriptase enzyme. In some such embodiments, the original mRNA template and template switching oligonucleotide is denatured from the cDNA, and the barcoded capture probe with optional UMI hybridizes with the cDNA to generate a complement of the cDNA.

In some embodiments, obtaining the plurality of cDNA sequences further comprises amplification (e.g., PCR amplification) and/or adaptor extension of each cDNA sequence in the plurality of cDNA sequences. In some embodiments, the adaptor extension occurs prior to cDNA amplification. In some such embodiments, the adaptor extension occurs during the first-strand cDNA synthesis. In some such embodiments, the adaptor extension occurs by hybridization of the RNA molecule to a capture probe. In some other embodiments, the adaptor extension occurs by hybridization of a cDNA molecule to a capture probe.

In some embodiments, the plurality of cDNA sequences is not fragmented, such that each cDNA sequence in the plurality of cDNA sequences is a full-length cDNA sequence. In some such embodiments, the plurality of cDNA sequences comprises intermediate products of a gene expression library preparation workflow (e.g., unfragmented cDNA sequences generated using a method for 3' gene expression library preparation).

In some embodiments, the plurality of cDNA sequences comprises a first subset of cDNA sequences, where each respective cDNA sequence in the first subset of cDNA sequences maps to a respective gene in a plurality of genes. The plurality of genes can be a targeted gene panel (e.g., a panel of genes of interest). In some embodiments, the plurality of genes is between five genes and twenty thousand genes. In some embodiments, the plurality of genes is between one hundred genes and ten thousand genes. In some embodiments, the plurality of genes is between five hundred genes and two thousand genes. In some embodiments, the plurality of genes is more than 10, more than 50, more than 100, more than 500, more than 1000, more than 2000, more than 5000, more than 10000, more than 15000, or more than 20000 genes.

In some embodiments, the plurality of cDNA sequences comprises a second subset of cDNA sequences, where each respective cDNA sequence in the second subset of cDNA sequences maps to a portion of a reference genome not represented by the plurality of genes to which the first subset of cDNA sequences is mapped. The second subset of cDNA sequences can include cDNA sequences that map to off-target regions of the reference genome and/or other genes not included in a targeted gene panel.

In some embodiments, the plurality of cDNA sequences consists of the first subset of cDNA sequences and the second subset of cDNA sequences. In some such embodiments, each cDNA sequence in the plurality of cDNA sequences maps to either a gene of interest or to an off-target region of a reference genome.

Each respective gene in the plurality of genes can be characterized by any number of transcripts. For example, in some embodiments, three or more transcripts correspond to each respective gene. In some embodiments, five or more transcripts correspond to each respective gene. In some embodiments, 2, 3, 4, 5, 6, 7, 8, 9, 10 or more transcripts correspond to each respective gene. In some embodiments, the corresponding plurality of transcripts of a respective gene in the plurality of genes comprises a plurality of isoforms of the respective gene.

Isoforms of a gene refer to mRNA molecules (and the corresponding cDNA molecules) that originate from the same genomic locus but comprise different nucleic acid sequences, including but not limited to transcription start sites (TSSs), protein coding DNA sequences (CDSs), and/or untranslated regions (UTRs). These differences are caused by alternative splicing, variable promoter usage, gene fusions or deletions, single nucleotide polymorphisms (SNPs), and/or other mutations or post-transcriptional genetic modifications. Isoforms of a gene may have different functional capacities due to the differences in mRNA sequence of the coding sequences and/or the cis-regulatory elements in the promoter sequences.

The identification of different isoforms of a gene is an essential step in accurately enriching for cDNA sequences of the respective gene. For example, where the diverging nucleic acid sequences of two or more isoforms of a target gene include different transcription start sites and/or untranslated regions, bait probes complementary to the 3' or 5' annotated ends of the gene may fail to capture all of the possible isoforms. This can occur if a nucleic acid bait is designed to hybridize to a region of a first isoform that extends beyond either of the terminal ends of a second isoform. While minimal bait probe sets are desirable for cost-effective and streamlined targeted sequencing analysis, in some cases where two or more isoforms have such drastically different lengths that they do not overlap, it may be necessary to design a plurality of nucleic acid baits such that each isoform can be bound and enriched. In some such cases, each non-overlapping isoform hybridizes to a different, unique bait probe.

Therefore, proper annotation of the genomic regions spanned by each isoform (e.g., the coding and/or non-coding sequences) is necessary to ensure that bait probe design generates a plurality of bait probes in which every transcript for the target gene is represented (e.g., hybridizable).

In some embodiments, each transcript in the plurality of transcripts is protein coding. Alternatively, one or more transcripts in the plurality of transcripts can comprise a non-coding sequence (e.g., a 3' or 5' untranslated region). For example, one or more transcripts in the plurality of transcripts can comprise a 3' UTR sequence downstream of a stop codon, or a 5' UTR upstream of a start codon. In some embodiments, one or more transcripts in the plurality of transcripts is protein coding but comprises an incomplete coding sequence. For example, in some such embodiments, a transcript in the plurality of transcripts corresponding to the respective gene is coding sequence (CDS) 3' incomplete, CDS 5' incomplete, or both CDS 3' and 5' incomplete. As used herein, CDS 3' incomplete refers to a protein-coding transcript that does not include the stop codon due to incomplete evidence. As used herein, CDS 5' incomplete refers to a protein-coding transcript that does not include a start codon due to incomplete evidence.

In some embodiments, reference databases are useful for aligning transcripts corresponding to the respective gene, such as the reference genome GENCODE Release 33 (GRCh38.p13). For instance, annotations for a respective gene are available as a reference database within the GENCODE Consortium, In other instances, annotations for a respective gene are available through the Ensembl project See, Harrow et al., 2012, "GENCODE: The reference human genome annotation for The ENCODE Project," Genome Res. 22 (9): 1760-1774: doi:10.1101/gr.135350.111; and Flicek et al., 2014, "Ensembl 2014," Nucleic Acids Res. 42 (Database issue):D749-D755: doi:10.1093/nar/gkt1196, the entire contents of which are incorporated herein by reference.

(ii) Spatial Library Preparation

Disclosed herein are methods of generating a plurality of extended nucleic acids (e.g., any of the extended nucleic acids described herein) for detection of analytes that include proteins and nucleic acids. In some instances, the methods include detection of nucleic acids. In some embodiments, the methods include detection of proteins.

As used herein, an "extended nucleic acid" refers to a nucleic acid having additional nucleotides added to the terminus (e.g., 3' or 5' end) of the nucleic acid thereby extending the overall length of the nucleic acid.

Disclosed herein are methods of preparing a library of target nucleic acids using bait oligonucleotides, wherein the library of target nucleic acids is initially prepared from nucleic acids that were hybridized to capture probes on a spatial array (i.e., a substrate). For example, captured nucleic acid sequences on a substrate can be put through a spatial workflow providing resultant nucleic acids that can be isolated, amplified, and/or otherwise processed for subsequent analysis, such as fragmentation and sequencing library preparation. Capture probes, substrates, and arrays have been described in previous sections of this application above and are incorporated into this section.

In some instances, embodiments of any of the methods described herein can include contacting a biological sample with a substrate comprising a plurality of attached capture probes, wherein a capture probe of the plurality comprises (i) a spatial barcode and (ii) a capture domain that binds specifically to a sequence present in an analyte (e.g., a nucleic acid); extending a 3' end of the capture probe using the analyte that is specifically bound to the capture domain as a template to generate an extended capture probe; and amplifying the extended capture probe. In some instances, embodiments of any of the methods described herein can include contacting a plurality of analyte capture agents to a biological sample, wherein an analyte capture agent of the plurality of the analyte capture agents comprises (i) an analyte binding moiety that binds to the analyte (e.g., a protein) and (ii) an oligonucleotide comprising an analyte binding moiety barcode and an analyte capture sequence; contacting the plurality of analyte capture agents to a substrate comprises a plurality of capture probes, wherein a capture probe of the plurality comprises a spatial barcode and a capture domain, wherein the capture domain binds to the analyte capture sequence; extending a 3' end of the capture probe using the analyte binding moiety barcode as a template to generate an extended capture probe; and amplifying the extended capture probe. Individual method steps and system features can be present in combination in many different embodiments; the specific combinations described herein do not in any way limit other combinations of steps and features.

Analytes can be captured on an array when contacting a biological sample with, e.g., a substrate (e.g., an array) comprising capture probes. Capture probes interact with analytes released from the biological sample through a capture domain, described throughout this application, to capture analytes. For example, a capture domain captures analytes via hybridization to a nucleic acid sequence in a target nucleic acid molecule from a biological sample. In some instances, the sequence complementary to the capture domain is a poly-adenylated (poly (A)) sequence. In some instances, the sequence complementary to the capture domain is designed to be specific to a sequence of interest (i.e., in a target analyte).

In the setting of nucleic acid detection, the nucleic acid analyte hybridizes directly to the capture probes on the array (e.g., a substrate). In the setting of protein detection, referring to FIG. 4, an analyte binding moiety 402 comprises a protein-binding moiety 404 and an oligonucleotide 408. In some instances, the analyte binding moieties are added to the biological sample. After association of the protein with the protein-binding moiety 404, the oligonucleotide is captured by a capture domain of the array (e.g., a substrate). Thus, the analyte binding moiety as used herein can be considered an analyte derivative, and its oligonucleotide can be captured and analyzed in a similar way that a nucleic acid analyte can be analyzed. Embodiments for analyte binding moieties has been described previously e.g., in WO 2020/176788 and/or U.S. Patent Application Publication No. 2020/0277663, each of which is incorporated by reference in its entirety.

Alternatively, a proxy for an analyte, can be captured by a capture domain on a capture probe on an array. For example, two probes can hybridize to target nucleic acids such that they can be ligated together to create a ligation product that can serve as a proxy of the target sequence. The ligation product can comprise a sequence that is substantially complementary to the capture domain of the capture probe on the array. The ligation product can be captured on the array and serve as a proxy for the presence of the target nucleic. In some embodiments, the sample is stained prior to creation of the nucleic acid library. In some embodiments, the biological sample is stained while the biological sample is on the slide. In some embodiments, the stained biological sample is imaged prior to creation of the nucleic acid library. In some embodiments, staining includes biological staining techniques such as H&E staining. In some embodiments, staining includes identifying analytes using fluorescently conjugated antibodies (e.g., immunofluorescence). In some embodiments, a biological sample is stained using two or more different types of stains, or two or more different staining techniques (e.g., IF, IHC, and/or H&E staining). For example, a biological sample can be prepared by staining and imaging using one technique (e.g., H&E staining and bright field imaging), destained (e.g., quenching or photobleaching), followed by staining and imaging using another technique (e.g., IHC/IF staining and fluorescence microscopy) for the same biological sample.

In some embodiments, prior to interaction with capture probes on the array, target-specific reactions are performed in the biological sample to enhance detection of one or more targets of interest. Examples of target specific reactions include, but are not limited to, ligation of target specific adaptors, probes and/or other oligonucleotides, target specific amplification using primers specific to one or more nucleic acid analytes, and target-specific detection using in situ hybridization, DNA microscopy, and/or antibody detection. In some embodiments, a capture probe includes capture domains targeted to target-specific products (e.g., amplification or ligation). A target analyte can then be captured by a capture probe (e.g., as described throughout herein).

In some embodiments, the methods provided herein include a permeabilizing step in order to release the analytes from the biological sample. In some embodiments, permeabilization occurs using a protease. In some embodiments, the protease is an endopeptidase. Endopeptidases that can be used include but are not limited to trypsin, chymotrypsin, elastase, thermolysin, pepsin, clostripan, glutamyl endopeptidase (GluC), ArgC, peptidyl-asp endopeptidase (ApsN), endopeptidase LysC and endopeptidase LysN. In some embodiments, the endopeptidase is pepsin.

In some embodiments, methods provided herein include permeabilization of the biological sample such that the capture probe can more easily bind to the analyte or analyte derivative (i.e., compared to no permeabilization). In some embodiments, reverse transcription (RT) reagents can be added to permeabilized biological samples. Incubation with the RT reagents can produce spatially-barcoded full-length cDNA from the captured analytes (e.g., polyadenylated mRNA). Second strand reagents (e.g., second strand primers, enzymes) can be added to the biological sample on the substrate to initiate second strand synthesis.

In some instances, the permeabilization step includes application of a permeabilization buffer to the biological sample. In some instances, the permeabilization buffer includes a buffer (e.g., Tris pH 7.5), $MgCl_2$, sarkosyl detergent (e.g., sodium lauroyl sarcosinate) or other detergent, enzyme (e.g., proteinase K, pepsin, collagenase, etc.), and nuclease free water. In some instances, the permeabilization step is performed at 37° C. In some instances, the permeabilization step is performed for about 20 minutes to 2 hours (e.g., about 20 minutes, about 30 minutes, about 40 minutes, about 50 minutes, about 1 hour, about 1.5 hours, or about 2 hours). In some instances, the releasing step is performed for about 40 minutes.

After permeabilization, in some instances, the analytes are captured by the capture probes and/or analyte capture agents. In some embodiments, such methods of increasing capture efficiency of a spatial array described herein includes contacting the spatial array with the biological sample and allowing the analyte to interact with the capture probes and/or analyte capture agents.

In some embodiments, the capture probe hybridized to the analyte can be extended using a polymerase (e.g., a reverse transcriptase) using the hybridized analyte as a template, to generate an extended capture probe. In some embodiments, a 3' end of the capture probe hybridized to the analyte can be extended using a polymerase (e.g., a reverse transcriptase) using the hybridized analyte as a template, to generate an extended capture probe. In some embodiments, a 5' end of the capture probe hybridized to the analyte can be extended using a polymerase (e.g., a reverse transcriptase) using the hybridized analyte as a template, to generate an extended capture probe. The extended capture probe can be amplified (e.g., via second strand synthesis) to generate a single-stranded nucleic acid comprising a sequence that is complementary to the extended capture probe. The single-stranded nucleic acid comprising a sequence that is complementary to the extended capture probe can be used to generate or can be a part of a nucleic acid library.

After hybridization of the analyte to the capture probe, the hybridized product is amplified. For example, obtaining the library of cDNA sequences further comprises amplification (e.g., PCR amplification) and/or adaptor extension of the cDNA sequences. In some embodiments, the adaptor extension occurs prior to cDNA amplification. In some such embodiments, the adaptor extension occurs during the first-strand cDNA synthesis.

In some embodiments, the method includes amplifying all or part of the analyte using isothermal amplification or non-isothermal amplification. In some embodiments, the amplifying creates an amplified product that includes (i) all or part of a sequence of the analyte or the analyte derivative bound to the capture probe, or a complement thereof, and (ii) all or a part of the sequence of the spatial barcode, or a complement thereof. In some embodiments, the determining step includes sequencing. A non-limiting example of sequencing that can be used to determine the sequence of the analyte, the analyte derivative, and/or spatial barcodes is in situ sequencing. In some embodiments, in situ sequencing is performed via sequencing-by-synthesis (SBS), sequential fluorescence hybridization, sequencing by ligation, nucleic acid hybridization, or high-throughput digital sequencing techniques. In some embodiments the analyte is RNA or DNA. In some embodiments, the analyte is a protein.

In some embodiments, after contacting a biological sample with a substrate that includes capture probes, a removal step can optionally be performed to remove all or a portion of the biological sample from the substrate. In some embodiments, the removal step includes enzymatic and/or chemical degradation of cells of the biological sample. For example, the removal step can include treating the biological sample with an enzyme (e.g., a proteinase, e.g., proteinase K) to remove at least a portion of the biological sample from the substrate. In some embodiments, the removal step can include ablation of the tissue (e.g., laser ablation).

In some embodiments, provided herein are methods for spatially detecting an analyte (e.g., detecting the location of an analyte, e.g., a biological analyte) from a biological sample (e.g., present in a biological sample), the method comprising: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein the capture probes capture the biological analyte; and (d) analyzing the captured biological analyte, thereby spatially detecting the biological analyte; wherein the biological sample is fully or partially removed from the substrate.

In some embodiments, a biological sample is not removed from the substrate. For example, the biological sample is not removed from the substrate prior to releasing a capture probe (e.g., a capture probe bound to an analyte) from the substrate. In some embodiments, such releasing comprises cleavage of the capture probe from the substrate (e.g., via a cleavage domain). In some embodiments, such releasing does not comprise releasing the capture probe from the substrate (e.g., a copy of the capture probe bound to an analyte can be made and the copy can be released from the substrate, e.g., via denaturation). In some embodiments, the biological sample is not removed from the substrate prior to analysis of an analyte bound to a capture probe after it is released from the substrate. In some embodiments, the biological sample remains on the substrate during removal of a capture probe from the substrate and/or analysis of an analyte bound to the capture probe after it is released from the substrate. In some embodiments, the biological sample remains on the substrate during removal (e.g., via denaturation) of a copy of the capture probe (e.g., complement). In some embodiments, analysis of an analyte bound to capture probe from the substrate can be performed without subjecting the biological sample to enzymatic and/or chemical degradation of the cells (e.g., permeabilized cells) or ablation of the tissue (e.g., laser ablation).

In some embodiments, at least a portion of the biological sample is not removed from the substrate. For example, a portion of the biological sample can remain on the substrate prior to releasing a capture probe (e.g., a capture probe bound to an analyte) from the substrate and/or analyzing an analyte bound to a capture probe released from the substrate. In some embodiments, at least a portion of the biological sample is not subjected to enzymatic and/or chemical degradation of the cells (e.g., permeabilized cells) or ablation of the tissue (e.g., laser ablation) prior to analysis of an analyte bound to a capture probe from the substrate.

In some embodiments, provided herein are methods for spatially detecting an analyte (e.g., detecting the location of an analyte, e.g., a biological analyte) from a biological sample (e.g., present in a biological sample) that include: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; where the biological sample is not removed from the substrate.

In some embodiments, provided herein are methods for spatially detecting a biological analyte of interest from a biological sample that include: (a) staining and imaging a biological sample on a substrate; (b) providing a solution comprising a permeabilization reagent to the biological sample on the substrate; (c) contacting the biological sample with an array on a substrate, wherein the array comprises one or more capture probe pluralities thereby allowing the one or more pluralities of capture probes to capture the biological analyte of interest; and (d) analyzing the captured biological analyte, thereby spatially detecting the biological analyte of interest; where the biological sample is not removed from the substrate.

In some embodiments, the method further includes subjecting a region of interest in the biological sample to spatial transcriptomic analysis. In some embodiments, one or more of the capture probes includes a capture domain. In some embodiments, one or more of the capture probes comprises a unique molecular identifier (UMI). In some embodiments, one or more of the capture probes comprises a cleavage domain. In some embodiments, the cleavage domain comprises a sequence recognized and cleaved by uracil-DNA glycosylase, apurinic/apyrimidinic (AP) endonuclease (APE1), U uracil-specific excision reagent (USER), and/or an endonuclease VIII. In some embodiments, one or more capture probes do not comprise a cleavage domain and is not cleaved from the array.

In some embodiments, a capture probe can be extended (an "extended capture probe," e.g., as described herein). For example, extending a capture probe can include generating cDNA from a captured (hybridized) RNA. This process involves synthesis of a complementary strand of the hybridized nucleic acid, e.g., generating cDNA based on the captured RNA template (the RNA hybridized to the capture domain of the capture probe). Thus, in an initial step of extending a capture probe, e.g., the cDNA generation, the captured (hybridized) nucleic acid, e.g., RNA, acts as a template for the extension, e.g., reverse transcription, step.

In some embodiments, the capture probe is extended using reverse transcription. For example, reverse transcription includes synthesizing cDNA (complementary or copy DNA) from RNA, e.g., (messenger RNA), using a reverse transcriptase. In some embodiments, reverse transcription is performed while the tissue is still in place, generating an analyte library, where the analyte library includes the spatial barcodes from the adjacent capture probes. In some embodiments, the capture probe is extended using one or more DNA polymerases.

In some embodiments, a capture domain of a capture probe includes a primer for producing the complementary strand of a nucleic acid hybridized to the capture probe, e.g., a primer for DNA polymerase and/or reverse transcription. The nucleic acid, e.g., DNA and/or cDNA, molecules generated by the extension reaction incorporate the sequence of the capture probe. The extension of the capture probe, e.g., a DNA polymerase and/or reverse transcription reaction, can be performed using a variety of suitable enzymes and protocols.

In some embodiments, a full-length DNA (e.g., cDNA) molecule is generated. In some embodiments, a "full-length" DNA molecule refers to the whole of the captured nucleic acid molecule. However, if a nucleic acid (e.g., RNA) was partially degraded in the tissue sample, then the captured nucleic acid molecules will not be the same length as the initial RNA in the tissue sample. In some embodiments, the 3' end of the extended probes, e.g., first strand cDNA molecules, is modified. For example, a linker or adaptor can be ligated to the 3' end of the extended probes. This can be achieved using single stranded ligation enzymes such as T4 RNA ligase or Circligase™ (available from Lucigen, Middleton, WI). In some embodiments, template switching oligonucleotides are used to extend cDNA in order to generate a full-length cDNA (or as close to a full-length cDNA as possible). In some embodiments, a second strand synthesis helper probe (a partially double stranded DNA molecule capable of hybridizing to the 3' end of the extended capture probe), can be ligated to the 3' end of the extended probe, e.g., first strand cDNA, molecule using a double stranded ligation enzyme such as T4 DNA ligase. Other enzymes appropriate for the ligation step are known in the art and include, e.g., Tth DNA ligase, Taq DNA ligase, *Thermococcus* sp. (strain 9°N) DNA ligase (9°N™ DNA ligase, New England Biolabs), Ampligase™ (available from Lucigen, Middleton, WI), and SplintR (available from New England Biolabs, Ipswich, MA). In some embodiments, a polynucleotide tail, e.g., a poly (A) tail, is incorporated at the 3' end of the extended probe molecules. In some embodiments, the polynucleotide tail is incorporated using a terminal transferase active enzyme.

In some embodiments, double-stranded extended capture probes are treated to remove any unextended capture probes prior to amplification and/or analysis, e.g., sequence analysis. This can be achieved by a variety of methods, e.g., using an enzyme to degrade the unextended probes, such as an exonuclease enzyme, or purification columns.

In some embodiments, extended capture probes are amplified to yield quantities that are sufficient for analysis, e.g., via DNA sequencing. In some embodiments, the first strand of the extended capture probes (e.g., DNA and/or cDNA molecules) acts as a template for the amplification reaction (e.g., a polymerase chain reaction).

In some embodiments, the amplification reaction incorporates an affinity group onto the extended capture probe (e.g., RNA-cDNA hybrid) using a primer including the affinity group. In some embodiments, the primer includes an affinity group and the extended capture probes includes the affinity group. The affinity group can correspond to any of the affinity groups described previously.

In some embodiments, the extended capture probes including the affinity group can be coupled to a substrate specific for the affinity group. In some embodiments, the substrate can include an antibody or antibody fragment. In some embodiments, the substrate includes avidin or streptavidin and the affinity group includes biotin. In some embodiments, the substrate includes maltose and the affinity group includes maltose-binding protein. In some embodiments, the substrate includes maltose-binding protein and the affinity group includes maltose. In some embodiments, amplifying the extended capture probes can function to release the extended probes from the surface of the substrate, insofar as copies of the extended probes are not immobilized on the substrate.

In some embodiments, the extended capture probe or complement or amplicon thereof is released. The step of releasing the extended capture probe or complement or amplicon thereof from the surface of the substrate can be achieved in a number of ways. In some embodiments, an extended capture probe or a complement thereof is released from the array by nucleic acid cleavage and/or by denaturation (e.g., by heating to denature a double-stranded molecule).

In some embodiments, the extended capture probe or complement or amplicon thereof is released from the surface of the substrate (e.g., array) by physical means. For example, where the extended capture probe is indirectly immobilized on the array substrate, e.g., via hybridization to a surface probe, it can be sufficient to disrupt the interaction between the extended capture probe and the surface probe. Methods for disrupting the interaction between nucleic acid molecules include denaturing double stranded nucleic acid molecules are known in the art. A straightforward method for releasing the DNA molecules (i.e., of stripping the array of extended probes) is to use a solution that interferes with the hydrogen bonds of the double stranded molecules. In some embodiments, the extended capture probe is released by an applying heated solution, such as water or buffer, of at least 85° C., e.g., at least 90, 91, 92, 93, 94, 95, 96, 97, 98, or 99° C. In some embodiments, a solution including salts, surfactants, etc. that can further destabilize the interaction between the nucleic acid molecules is added to release the extended capture probe from the substrate.

In some embodiments, where the extended capture probe includes a cleavage domain, the extended capture probe is released from the surface of the substrate by cleavage. For example, the cleavage domain of the extended capture probe can be cleaved by any of the methods described herein. In some embodiments, the extended capture probe is released from the surface of the substrate, e.g., via cleavage of a cleavage domain in the extended capture probe, prior to the step of amplifying the extended capture probe.

In some embodiments, where a sample is barcoded directly via hybridization with capture probes or analyte capture agents hybridized, bound, or associated with either the cell surface, or introduced into the cell, as described above, sequencing can be performed on the intact sample.

A wide variety of different sequencing methods can be used to analyze the barcoded analyte or moiety. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based single plex methods, emulsion PCR), and/or isothermal amplification. Non-limiting examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, sequence by synthesis sequencing, nanopore sequencing, and Polony sequencing), ligation methods, and microarray methods.

(iii) Processing of Nucleic Acid Libraries

In some embodiments, after creation of the library of nucleic acids (e.g., plurality of nucleic acids), one or more bait oligonucleotides (e.g., from one or more panels as described herein) are hybridized to a plurality of nucleic acids. The nucleic acids include all or a portion of a sequence of an analyte of interest or a complement thereof and/or include all or a portion of a spatial barcode of interest or a complement thereof. In some embodiments, one or more bait oligonucleotides are hybridized to the nucleic acid including all or a portion of a sequence of analyte of interest or a complement thereof.

In some instances, one or more libraries of nucleic acids are pooled. In some instances, one or more libraries are incubated with Cot DNA (e.g., human Cot DNA). In some instances, one or more libraries are incubated with universal blocker nucleic acids, which hybridize to one or more well-expressed nucleic acids to prevent hybridization of unwanted nucleic acids to bait oligonucleotides.

In other embodiments, prior to hybridization of the bait oligonucleotides, the library, the nucleic acid(s), or the enriched nucleic acid(s) can be quantified using quantitative PCR (qPCR). In some embodiments, the library, the nucleic acid(s), or the enriched nucleic acid(s) can be fragmented. In some embodiments, the library, the nucleic acid(s), or the enriched nucleic acid(s) can be fragmented by enzyme-based methods (e.g., by restriction enzymes, nicking enzymes and/or transposases). In some embodiments, the library, the nucleic acid(s), or the enriched nucleic acid(s) can be fragmented by endonucleases. In some embodiments, the library, the nucleic acid(s), or the enriched nucleic acid(s) can be fragmented by mechanical shearing (e.g., acoustic shearing, hydrodynamic shearing, and/or nebulization). In some embodiments, the library, the nucleic acid(s), or the enriched nucleic acid(s) can be fragmented by combined enzyme-based methods and mechanical shearing. In some embodiments, the library, the nucleic acid(s), or the enriched nucleic acid(s) can be further processed via end-repair, poly-A tailing, or a combination thereof. In some embodiments, adaptors are ligated to each nucleic acid or enriched nucleic acid sequence. In some embodiments, the adaptors can be ligated to the 3' end of the nucleic acid or enriched nucleic acid sequence. In some embodiments, the adaptors can be ligated to the 5' end of the nucleic acid sequence or enriched nucleic acid sequence. In some embodiments, the adaptors can be nucleic acid sequences that add a function, e.g., spacer sequences, primer sequences/sites, barcode sequences, unique molecular identifier (UMI) sequences, linkers, and/or sequencing adaptors.

In some embodiments, the methods disclosed herein include sample index (SI) PCR, which adds nucleic acid sequences (e.g., barcodes) to the 5' and/or 3' ends of a nucleic acid sequence or an enriched nucleic acid sequence. In some instances, a SI-PCR reaction is performed at 67° C. In some embodiments, SI-PCR is a PCR reaction that introduces sample index sequences (e.g., i5 and i7) to the 5' and/or 3' ends of a nucleic acid sequence or an enriched nucleic acid sequence. In some embodiments, methods for SI-PCR add the i5 sample index sequence. In some embodiments, methods for SI-PCR add the i7 sample index sequence. In some embodiments, a P5 adapter is added to a nucleic acid sequence or an enriched nucleic acid sequence. In some embodiments, a P7 adapter is added to a nucleic acid sequence or an enriched nucleic acid sequence. In some embodiments, SI-PCR is performed before bait oligonucleotide enrichment of a nucleic acid of interest. In some embodiments, SI-PCR is performed after bait oligonucleotide enrichment of a nucleic acid of interest.

In some embodiments, the nucleic acid of interest (before or after enrichment using a bait oligonucleotide) or a library generated from the same can be dried. In some embodiments, drying includes a dehydrating process such as heat, a vacuum, lyophilization, desiccation, filtration, and air-drying. In some instances, a vacuum centrifuge is used to dry the sample. In some instances, drying is performed at about 50° C., about 55° C., about 60° C., about 63° C., about 65° C., about 67° C., about 70° C., or about 75° C. In some embodiments, drying can be performed for at least 1 hour, at least 2 hours, at least 3 hours or at least 4 hours. A sample can be stored (e.g., at −20° C.) if the sample is not used immediately. In some embodiments, the nucleic acid of interest (before or after enrichment using a bait oligonucleotide) or a library generated from the same is not dried.

(d) Targeted Capture of Analytes Using Hybridization of Bait Oligonucleotides

After preparation of a nucleic acid library from a biological sample, the library can be incubated with a plurality of bait oligonucleotides in order to selectively enrich the library for targets of interest. Target analytes can be isolated from the library, creating an enriched population of target analytes. While whole transcriptome spatial analysis is very informative, a more targeted gene enrichment allows for the spatial localization of a subset of targets that are of particular interest, for example for cancer or disease detection of related cancer or disease related genes and gene expression. As such, a research can focus on a subset of genes of interest and maximize spatial knowledge of those genes while minimizing costs and reagents associated with spatial whole transcriptomic workflows.

(i) Design of Bait Oligonucleotides

In some embodiments, bait oligonucleotide sets are designed to target and hybridize to a plurality of nucleic acids (e.g., to prepared spatial libraries, e.g., to prepared cDNA libraries). In some embodiments, bait oligonucleotide sets hybridize to targeted nucleic acids (e.g., cDNA) from a more expansive set of library nucleic acids. In some embodiments, the hybridized product (e.g., the bait oligonucleotide and hybridized nucleic acid) are then captured by streptavidin beads. In some embodiments, the hybridized product (e.g., the bait oligonucleotide and hybridized nucleic acid) are then captured by avidin beads. Unhybridized nucleic acids are washed away. The targeted product is reamplified and sequenced. In some embodiments, the reamplifed targeted product can be fragmented, ligated with adaptor sequences, and amplified by SI-PCR.

Disclosed herein are methods to design and test candidate bait oligonucleotide sequences. Candidate bait oligonucleotide sequences are designed so that each bait oligonucleotide sequence theoretically hybridizes to a unique target of interest. Accordingly, the designed bait oligonucleotides are at least 40 nucleotides in length. To identify a bait oligonucleotide of interest, at unique 40 nucleotide sections of the human transcriptome are identified and aligned to the genome using an aligner designed for aligning RNA-seq data. In some embodiments, bait oligonucleotides are designed to hybridize to a particular exon. In some embodiments, bait oligonucleotides are designed to span an exon-exon junction. In some embodiments, bait oligonucleotides can hybridize to a target, allowing for identification of splicing and alternative splicing transcripts in the transcriptome. Using the alignments, sequences that align to the genome one or more times are identified and cataloged. Each bait designed can be tested against (i.e., compared to) a sequence identified in the genome. If the sequences in the bait oligonucleotide and in the genome do not match, then the bait can be tested in one or more panels as disclosed herein.

The present disclosure provides a method to design nucleic acid baits for full-length cDNA comprising obtaining a coding sequence for each transcript (e.g., isoform) of each target gene in a targeted gene panel. Where the coding sequence is less than a threshold length (e.g., 120 base pairs), a full mRNA sequence can be used instead. The method further comprises, for each 120 base pair sub-sequence in each coding sequence, obtaining a count of the number of transcripts in which the 120 base pair sub-sequence occurs. Each sub-sequence is ranked by the obtained count and a first sub-sequence is selected from the sub-sequence that occurs in the maximal number of transcripts for the respective gene. The first sub-sequence is further subjected to filtering criteria (e.g., uniqueness, mappability, absence of repetitive subsequences, and/or overall GC content). In some embodiments, if the first sub-sequence fails to satisfy one or more filtering criteria, the first sub-sequence is rejected and a new first sub-sequence is selected from the sub-sequence that occurs in the maximal number of transcripts for the respective gene that further satisfies the filtering criteria. In some embodiments, if the first sub-sequence fails to satisfy one or more filtering criteria, the first sub-sequence is modified (e.g., by truncating the first sub-sequence such that it satisfies the one or more filtering criteria and/or by shifting the first sub-sequence along the reference genome such that it satisfies the one or more filtering criteria).

The method further comprises selecting a second sub-sequence from the sub-sequence that occurs in the maximal number of remaining transcripts for the respective gene (e.g., other than the transcripts in which the first sub-sequence occurred). The method is iterated for all remaining transcripts until no transcripts remain (e.g., at least one sub-sequence in the plurality of selected sub-sequence occurs in each transcript in the plurality of transcripts for the target gene).

The method provided in the present disclosure improves upon the current technology by utilizing full-length cDNA sequences rather than 3' fragmented sequencing libraries, allowing access to larger regions of reliably annotated sequences for nucleic acid bait design. For example, full-length cDNA sequences comprise coding sequences, which are generally well-annotated, ensuring better targeted hybridization results and on-target rates.

Full-length cDNA sequences include common sequences shared across transcripts (e.g., isoforms), allowing the design of nucleic acid baits that can target multiple transcripts and reduce the number of nucleic acid baits required by 10-fold. The resulting plurality of nucleic acid baits can thus be downsized and streamlined, leading to higher efficiency and reduced costs for users desiring nucleic acid baits for large and/or custom targeted gene panels. As an example, whereas a plurality of nucleic acid baits conventionally “tiled” for 1× coverage of a 1000-gene panel would comprise between 38,000 and 68,000 nucleic acid baits, a plurality of nucleic acid baits designed using the presently disclosed method for the same 1000-gene panel would comprise between 2,500 and 4,000 nucleic acid baits. Furthermore, the presently disclosed method can be performed for any application in which targeted analysis is desired (e.g., single cell RNA sequencing and/or spatial gene expression profiling). In some instances, the plurality of nucleic acid baits comprises at least 500, at least 1000, at least 2000, at least 3000, at least 4000, or at least 5000 nucleic acid baits.

In some instances, each respective nucleic acid bait in the plurality of nucleic acid baits that hybridizes to a cDNA sequence mapping to a respective gene in the plurality of genes (i) selectively hybridizes to a first subset of transcripts, in a corresponding plurality of subsets of transcripts in the plurality of transcripts corresponding to the respective gene, or (ii) selectively hybridizes to another subset of transcripts, other than the first subset of transcripts, in the corresponding plurality of subsets of transcripts in the plurality of transcripts corresponding to the respective gene. Each respective transcript in the corresponding plurality of transcripts of each respective gene in the plurality of genes is hybridizable to a nucleic acid bait in the plurality of nucleic acid baits.

For example, a nucleic acid bait can hybridize to (e.g., can comprise nucleic acid sequences complementary to) one or more nucleic acid sequences corresponding to a target gene. In some cases, the one or more nucleic acid sequences that hybridize to the nucleic acid bait represent a corresponding one or more transcripts, or isoforms, of the target gene. As used herein, a subset of transcripts (e.g., a subset of isoforms) is defined as the group of transcripts (e.g., isoforms) for the target gene that hybridize to a respective nucleic acid bait.

In some embodiments, a nucleic acid bait that hybridizes to a cDNA sequence for a target gene selectively hybridizes to each transcript in the plurality of transcripts for the respective gene. For example, a single nucleic acid bait can be hybridized to all isoforms for a target gene, such that the first subset of isoforms consists of the plurality of isoforms for the target gene. In some such instances, no other subset of isoforms is defined (e.g., the plurality of isoforms can be grouped into only a single or first subset of isoforms).

In some instances, the plurality of transcripts for a target gene can be subdivided into a plurality of subsets of transcripts. The plurality of subsets of transcripts can include a first and a second subset of transcripts.

In some embodiments, each subset of transcripts in the plurality of subsets of transcripts is defined as the group of transcripts to which a respective nucleic acid bait hybridizes. In such cases, the first subset of transcripts is defined as the group of transcripts to which at least a first nucleic acid bait hybridizes, and the second subset of transcripts is defined as the group of transcripts to which at least a second nucleic acid bait hybridizes. For example, a first group of transcripts (e.g., isoforms) for the target gene that hybridize to a first nucleic acid bait is defined as a first subset of transcripts (e.g., a first subset of isoforms). Furthermore, a second group of transcripts (e.g., isoforms) for the target gene that hybridize to a second nucleic acid bait is defined as a second subset of transcripts (e.g., a second subset of isoforms).

In some embodiments, the second subset of transcripts consists of transcripts not included in the first subset of transcripts (e.g., a first subset and a second subset of isoforms can comprise mutually exclusive groups of isoforms).

In some instances, a first subset of isoforms can be selected by counting matches for each possible sub-sequence, of a given length, of a candidate bait sequence (e.g., sub-sequences of a target gene coding sequence or mRNA sequence).

Hybridization matching between each possible bait sub-sequence and each position across each isoform is performed iteratively for every isoform for the respective gene. The number of isoforms that match (e.g., comprise a complementary sequence to) each bait sub-sequence is tallied, the bait sub-sequence with the highest number of matches is selected as the first nucleic acid bait, and the subset of isoforms that match the first nucleic acid bait is defined as the first subset of isoforms. In some instances, when the corresponding first subset of isoforms fails to account for all the isoforms for the target gene, the process is repeated for all remaining isoforms that failed to match with the first nucleic acid bait. Thus, the bait sub-sequence with the highest number of matches to the remaining isoforms (e.g., the isoforms not included in the first subset of isoforms) is selected as the second nucleic acid bait, and the second subset of isoforms that match the second nucleic acid bait is defined as the second subset of isoforms.

In some instances, the process can be repeated as many times as necessary until a plurality of nucleic acid baits are identified such that all transcripts in the plurality of transcripts for the respective gene is hybridizable to at least one nucleic acid bait in the plurality of nucleic acid baits.

In some cases, the plurality of subsets of transcripts includes at least one, at least two, at least three, at least four, at least five, at least six, at least seven, at least eight, at least nine, or at least ten subsets of transcripts. In some embodiments, each subset of transcripts corresponds to a single nucleic acid bait. In some alternative embodiments, each subset of transcripts corresponds to a plurality of nucleic acid baits.

In some embodiments, a subset of transcripts other than the first subset of transcripts consists of one or more, two or more, three or more, four or more, five or more, six or more, seven or more, eight or more, nine or more, or ten or more transcripts. In some embodiments, the plurality of nucleic acid baits comprises at least $2\times10^3$, at least $3\times10^3$, at least $4\times10^3$, at least $5\times10^3$, at least $1\times10^4$, at least $2\times10^4$, at least $3\times10^4$, at least $4\times10^4$, at least $5\times10^4$, at least $6\times10^4$, at least $7\times10^4$, or at least $1\times10^5$ nucleic acid baits.

In some embodiments, the plurality of nucleic acid baits includes a minimum number of baits necessary to selectively hybridize to each respective transcript in the corresponding plurality of transcripts for a respective gene in the plurality of genes. For example, each respective transcript in the corresponding plurality of transcripts of each respective gene in the plurality of genes is hybridizable to at least one nucleic acid bait in the plurality of nucleic acid baits.

In some embodiments, each nucleic acid bait in the plurality of nucleic acid baits is hybridizable to a single transcript in the plurality of transcripts, and the number of nucleic acid baits in the plurality of nucleic acid baits is equal to the number of transcripts in the plurality of transcripts for each respective gene in the plurality of genes. In some embodiments, each nucleic acid bait in the plurality of nucleic acid baits is hybridizable to a plurality of transcripts, and the number of nucleic acid baits in the plurality of nucleic acid baits is less than the number of transcripts in the plurality of transcripts for each respective gene in the plurality of genes.

In some such embodiments, the bait coverage for each respective transcript in the plurality of transcripts for the respective gene is less than 1×. In some such embodiments, the bait coverage for each respective isoform in the plurality of isoforms for the first genetic target is less than 0.8×, less than 0.6×, less than 0.4×, less than 0.2×, or less than 0.1×.

In some embodiments, each respective nucleic acid bait in the plurality of nucleic acid baits shares less than a threshold percentage of sequence identity to any other nucleic acid bait in the plurality of nucleic acid baits. For instance, in some embodiments, each respective nucleic acid bait in the plurality of nucleic acid baits shares less than 100 percent, less than 98 percent, less than 96 percent, less than 94 percent, less than 92 percent, less than 90 percent, less than 88 percent, less than 86 percent, less than 84 percent, less than 82 percent, less than 80, less than 70 percent, less than 60 percent, less than 50 percent, or less than 40 percent identity to any other nucleic acid bait in the plurality of nucleic acid baits. In some embodiments, the threshold percentage of sequence identity is ten percent, twenty percent, thirty percent, or between five and fifty percent. In some embodiments, the threshold of shared sequence identity between a respective nucleic acid bait in the plurality of nucleic acid baits to any other nucleic acid bait in the plurality of nucleic acid baits determines the level of cross-hybridization of each respective nucleic acid bait to off-target sequence reads. In some embodiments, each respective nucleic acid bait in the plurality of nucleic acid baits comprises a nucleic acid sequence that has a minimal identity to the reference genome of at least 90%. In some embodiments, each respective nucleic acid bait in the plurality of nucleic acid baits comprises a nucleic acid sequence that has a minimal identity to the reference genome of at least 90%, at least 91%, at least 92%, at least 93%, at least 94%, at least 95%, at least 96%, at least 97%, at least 98%, or at least 99%.

In some embodiments, each respective nucleic acid bait in the plurality of nucleic acid baits that hybridizes to a transcript in the plurality of transcripts of the respective gene has a Tm with respect to the transcript that is between a first threshold temperature and a second threshold temperature. In some such embodiments, the first threshold temperature is between 55° C. and 85° C. and the second threshold temperature is between 90° C. and 110° C. In some instances, hybridization occurs at 65° C. In some instances, hybridization occurs at 60° C.

In some embodiments, each respective nucleic acid bait in the plurality of nucleic acid baits hybridizes to a region of the respective gene that is at least a minimum threshold distance away from any annotated start and/or stop sites of the respective gene. In some embodiments, a respective nucleic acid bait in a plurality of nucleic acid baits for a respective sequence read in a plurality of sequence reads mapping to a respective gene is located at a position that is at least a minimum threshold distance from the 3' end of the respective sequence read. In some such embodiments, off-target hybridization of a respective nucleic acid bait to a respective cDNA sequence can occur where there are unannotated poly-A sites or poly-A sequences present in the genomic exon and/or mRNA sequence that cause oligo-dT mispriming. As a result, in some such embodiments, the optimal position for nucleic acid bait hybridization to a corresponding cDNA sequence is located at a position that is at least a minimum threshold distance from the 3' end. Non-limiting examples of a minimum threshold distance are from 100 to 200 base pairs (bp), from 200 to 300 bp, from 300 to 400 bp, from 400 to 500 bp, from 500 to 600 bp, from 600 to 700 bp, from 700 to 800 bp, from 800 to 900 bp, from 900 to 1000 bp, or more than 1000 bp. In some embodiments, the percentage of cDNA sequences that preferentially hybridize to nucleic acid baits at positions at least a minimum threshold distance away from the 3' end is between 0% and 10%, between 10% and 20%, or between 20% and 30%. In addition, in some embodiments, nucleic acid baits comprising unannotated poly-A sites or poly-A sequences in the mRNA sequence are removed from the plurality of nucleic acid baits. In some instances, if the sequences in the bait oligonucleotide and in the genome match, then a modified bait is designed. To prepare a modified bait, one can slide the initial sequence +/−40 bp from the original position to identify a potentially new bait oligonucleotide. With each design, the new bait oligonucleotide is tested against the genome. After all such candidates are cataloged, the bait oligonucleotides that are ultimately included in one or more panels described herein are ordered (i.e., ranked) based on the bait oligonucleotide length (i.e., a longer bait is prioritized) and then by distance to the original intended position (with priority to sequences closer to the original intended position). However, if no bait meets the required criteria, that bait is dropped and no bait is designed at that position.

In some embodiments, the bait oligonucleotide sequence is 40 nucleotides long. In some embodiments, the bait oligonucleotide sequence is between 40 and 160 nucleotides long. In some embodiments, the bait oligonucleotide sequence is between 40 and 120 nucleotides long. In some embodiments, the bait oligonucleotide sequence is about 40, about 41, about 42, about 43, about 44, about 45, about 46, about 47, about 48, about 49, about 50, about 51, about 52 about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, about 151, about 152, about 153, about 154, about 155, about 156, about 157, about 158, about 159, or about 160 nucleotides long. In some instances, bait oligonucleotides are single stranded, 120 nucleotide-long DNA oligonucleotides with a 5' biotin modification. In some instances, each bait targets a unique library molecule. Bait oligonucleotides can span all mature mRNA sequences, including UTRs and all annotated isoforms.

In some embodiments, a bait oligonucleotide of the plurality of bait oligonucleotides includes a domain that binds specifically to all or a portion of the spatial barcode or a complement thereof. In some embodiments, a bait oligonucleotide of the plurality of bait oligonucleotides includes a domain that binds specifically to all or a portion of the sequence of the analyte from the biological sample, or a complement thereof. In some embodiments, a bait oligonucleotide of the plurality of bait oligonucleotides includes a domain that binds specifically to all or a portion of the spatial barcode or a complement thereof and all or a portion of the sequence of the analyte from the biological sample, or a complement thereof. In some embodiments, the domain of the bait oligonucleotide hybridizes to an analyte of interest. In some embodiments, the domain of the bait oligonucleotide binds specifically to an analyte of interest. In some embodiments, the domain of the bait oligonucleotide binds specifically to all or a portion of the spatial barcode or a complement thereof. In some embodiments, the domain of the bait oligonucleotide binds specifically to all or a portion of the sequence of the analyte from the biological sample. In some embodiments, the domain of the bait oligonucleotide binds specifically to a 3' portion of the sequence of the analyte from the biological sample or a complement thereof. In some embodiments, the domain of the bait oligonucleotide binds specifically to a 5' portion of the sequence of the analyte from the biological sample or a complement thereof. In some embodiments, the domain of the bait oligonucleotide binds specifically to an intron in the sequence of the analyte from the biological sample or a complement thereof. In some embodiments, the domain of the bait oligonucleotide binds specifically to an exon in the sequence of the analyte from the biological sample or a complement thereof. In some embodiments, the domain of the bait oligonucleotide binds specifically to an untranslated 3' region of the analyte from the biological sample or a complement thereof. In some embodiments, the domain of the bait oligonucleotide binds specifically to an untranslated 5' region of the analyte from the biological sample or a complement thereof.

In some embodiments, the domain of the bait oligonucleotide sequence is 40 nucleotides long. In some embodiments, the domain of the bait oligonucleotide sequence is between 40 and 160 nucleotides long. In some embodiments, the domain of the bait oligonucleotide sequence is between 40 and 120 nucleotides long. In some embodiments, the domain of the bait oligonucleotide sequence is about 40, about 41, about 42, about 43, about 44, about 45, about 46, about 47, about 48, about 49, about 50, about 51, about 52 about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, about 151, about 152, about 153, about 154, about 155, about 156, about 157, about 158, about 159, or about 160 nucleotides long.

In some embodiments, the analyte from the biological sample is associated with a disease or condition. In some embodiments, the analyte from the biological sample comprises a mutation. In some embodiments, the analyte from the biological sample comprises a single nucleotide polymorphism (SNP). In some embodiments, the analyte from the biological sample comprises a trinucleotide repeat.

In some embodiments, the domain of the bait oligonucleotide hybridizes to a particular exon of a transcript (i.e., an mRNA molecule). For example, a transcript can be processed such that an exon that would otherwise be excised during a normal setting is included in the mature mRNA product in a different setting (e.g., a pathological setting such as cancer). In some embodiments, the domain of the bait oligonucleotide identifies (e.g., hybridizes to) one or more isoforms or an analyte, but not others. In some embodiments, for example, a bait oligonucleotide hybridizes to a particular exon that is detected in a pathological setting (e.g., cancer).

In some embodiments, there is more than one bait oligonucleotide for a particular analyte of interest in a panel. For example, an analyte can undergo alternate splicing (e.g., as in an mRNA molecule). In some embodiments, different baits could detect and enhance particular transcripts, thereby detecting whether a particular exon is included in an analyte. Thus, in some embodiments, a panel will include at least 2, at least 3, at least 4, at least 5, at least 6, at least 7, at least 8, at least 9, at least 10, or more bait oligonucleotides for one analyte.

In some embodiments, a bait oligonucleotide is fully complementary (i.e., 100% complementary) to a portion of a target analyte. In some embodiments, a bait oligonucleotide is partially complementary (i.e., less than 100% complementary) to a portion of a target analyte. In some embodiments, a bait oligonucleotide has at least 75%, at least 80%, at least 85%, at least 90%, at least 91%, at least 92%, at least 93%, at least 94%, at least 95%, at least 96%, at least 97%, at least 98%, or at least 99% sequence identity to a portion of a target analyte.

In some embodiments, a bait oligonucleotide is partially complementary (i.e., less than 100% complementary) to a portion of a target analyte. In some embodiments, a bait oligonucleotide is partially complementary (i.e., less than 100% complementary) to a portion of a target analyte. In some embodiments, part of the bait oligonucleotide hybridizes to a portion of a target analyte. In some embodiments, part of the bait oligonucleotide has at least 75%, at least 80%, at least 85%, at least 90%, at least 91%, at least 92%, at least 93%, at least 94%, at least 95%, at least 96%, at least 97%, at least 98%, or at least 99% sequence identity to a portion of a target analyte.

Bait oligonucleotides are included in one or more panels (e.g., cohorts). Panels include groups of bait oligonucleotides that target a particular cohort of analytes. For example, a panel can include a set of bait oligonucleotides that is particular to a pathological setting. In some embodiments, more than one panel (e.g., set of bait oligonucleotides) can be used to enhance detection of analytes. For example, in some embodiments, at least 1, at least 2, at least 3, at least 4, at least 5, or more panels (e.g., set of bait oligonucleotides) can be used to enhance detection of analytes.

In some embodiments, a panel includes bait oligonucleotides that hybridize and enhance detection of analytes dysregulated in cancer (e.g., a cancer panel). In some embodiments, the cancer panel allows for quantitative analysis of analytes aberrantly expressed in the cancer transcriptome while avoiding the excess costs and time associated with sequencing an entire exome. The bait oligonucleotides and target analytes for an exemplary cancer panel are provided in Table 1. In some embodiments, the bait oligonucleotides in the cancer panel can include detection of dysregulated analytes associated with biological processes such as apoptosis, metabolism, cell cycle (e.g., checkpoint analytes), DNA damage and repair, hypoxia, and stress toxicity. More specifically, the bait oligonucleotides in the cancer panel target cancer-specific analytes such as analytes that function in pathways that include but are not limited to the Myc pathway, Hippo pathway, RTK/RAS pathway, TP53 and TP53-associate pathway, TFGβ pathway, and Wnt pathway. The bait oligonucleotides in the cancer panel also can detect cancer hot spots, tumor suppressor analytes, and immune-dysregulated analytes. The bait oligonucleotides and target analytes for an exemplary cancer panel were disclosed in U.S. Appl. No. 62/970,066 (Titled "Capturing Targeted Genetic Targets Using A Hybridization/Capture Approach") and U.S. Appl. No. 62/929,686, (Titled "Capturing Targeted Genetic Targets Using A Hybridization/Capture Approach"), each of which is incorporated by reference in its entirety.

In some embodiments, a panel includes bait oligonucleotides that hybridize and enhance detection of analytes associated with immunological dysregulation (e.g., an immunology panel). In some embodiments, the immunology panel allows for quantitative analysis of analytes associated with immune-dysregulation while avoiding the excess costs and time associated with sequencing an entire exome. The bait oligonucleotides and target analytes for an exemplary immunology panel are provided in Table 2. In some embodiments, the bait oligonucleotides in the immunology panel can include detection of dysregulated analytes associated with biological processes such as B cell function, T cell function, cell cycle, cell signaling, interleukin signaling, and metabolism. More specifically, bait oligonucleotides target analytes that include but are not limited to transcription factors, T cell activation markers, antigen presentation genes, metabolic genes, and SIRP family members. In some embodiments, the immunology panel has applications to detect associated with immunological dysregulation to examine innate immunity, adaptive immunity, one or more inflammatory responses, detection of one or more infectious diseases (e.g., a bacterial infection; a viral infection), and immune response in a transplant recipient. More specifically, the bait oligonucleotides in the immunology panel target immune-specific biomarkers that include but are not limited to lineage markers, tissue markers, and cancer markers. In some embodiments, the bait oligonucleotides enhance detection of analytes expressed in bone marrow, gut, lung, salivary gland, intestine, lymph node, stem cells, or a combination thereof. The bait oligonucleotides and target analytes for an exemplary immunology panel were disclosed in U.S. Appl. No. 62/970,066 (Titled "Capturing Targeted Genetic Targets Using A Hybridization/Capture Approach") and U.S. Appl. No. 62/929,686, (Titled "Capturing Targeted Genetic Targets Using A Hybridization/Capture Approach"), each of which is incorporated by reference in its entirety.

In some embodiments, a panel includes bait oligonucleotides that hybridize and enhance detection of analytes that detect pathway dysregulation (e.g., a pathway panel or a gene signature panel). In some embodiments, the pathway panel allows for quantitative analysis of analytes associated with pathway dysregulation while avoiding the excess costs and time associated with sequencing an entire exome. The bait oligonucleotides and target analytes for an exemplary pathway panel are provided in Table 3. In some embodiments, the bait oligonucleotides in the pathway panel can include detection of dysregulated analytes associated with complex signal transduction pathways. The target analytes include analytes specific to disease or drug targets; G-protein coupled receptors (GPCRs), one or more kinases; one or more epigenetic markers; or one or more checkpoint analytes. Analytes detected by bait oligonucleotides in the pathway panel include but are not limited to tissue markers of cancer dysregulation, central nervous system dysregulation, inflammation dysregulation, metabolic dysregulation, cardiovascular dysregulation, respiratory dysregulation, and reproductive dysregulation. The bait oligonucleotides and target analytes for an exemplary pathway panel were disclosed in U.S. Appl. No. 62/970,066 (Titled "Capturing Targeted Genetic Targets Using A Hybridization/Capture Approach") and U.S. Appl. No. 62/929,686, (Titled "Capturing Targeted Genetic Targets Using A Hybridization/Capture Approach"), each of which is incorporated by reference in its entirety.

In some embodiments, a panel includes bait oligonucleotides that hybridize and enhance detection of analytes that detect neurological development and/or dysregulation. In some embodiments, a panel includes bait oligonucleotides that hybridize and enhance detection of analytes that detect neurological development. In some embodiments, a panel includes bait oligonucleotides that hybridize and enhance detection of analytes that detect neurological dysregulation. In some embodiments, a panel includes bait oligonucleotides that hybridize and enhance detection of analytes that detect neurological development and dysregulation. In some embodiments, the neurological panel allows for quantitative analysis of analytes associated with pathway dysregulation while avoiding the excess costs and time associated with sequencing an entire transcriptome. The bait oligonucleotides and target analytes for an exemplary neurological panel are provided in Table 4. In some embodiments, the bait oligonucleotides in the neurological panel can include detection of dysregulated analytes associated with axonal targeting, hypoxia, and glioblastoma. In some embodiments, the bait oligonucleotides in the neurological panel can include detection of dysregulated analytes associated with axonal targeting. In some embodiments, the bait oligonucleotides in the neurological panel can include detection of dysregulated analytes associated with hypoxia. In some embodiments, the bait oligonucleotides in the neurological panel can include detection of dysregulated analytes associated with glioblastoma. In some embodiments, the bait oligonucleotides in the neurological panel can include detection of mitochondrial protein-coding genes. In some embodiments, the bait oligonucleotides in the neurological panel can include detection of mitochondrial protein-coding genes in order to evaluate energy metabolism.

In some instances, additional (i.e., custom) baits can be added to each panel. Further, in some instances, a fully-custom panel can be prepared.

In some embodiments, any one of the panels disclosed herein include bait oligonucleotides that can enhance detection of at least about 100 analytes, about 200 analytes, about 300 analytes, about 400 analytes, about 500 analytes, about 600 analytes, about 700 analytes, about 800 analytes, about 900 analytes, about 1000 analytes, about 1100 analytes, about 1200 analytes, about 1300 analytes, about 1400 analytes, about 1500 analytes, about 1600 analytes, about 1700 analytes, about 1800 analytes, about 1900 analytes, about 2000 analytes or more.

In some embodiments, a bait oligonucleotide enhances detection of an analyte of interest by about 1.5 fold, about 2 fold, about 3 fold, about 4 fold, about 5 fold, about 6 fold, about 7 fold, about 8 fold, about 9 fold, about 10 fold, about 20 fold, about 50 fold, about 100 fold, 500 fold, 1000 fold, or greater in comparison to analytes that are not detected using a bait oligonucleotide.

In some embodiments, a bait oligonucleotide includes a molecular tag. As disclosed herein, a molecular tag of a bait oligonucleotide is affixed to (e.g., conjugated to) the nucleic acid sequence of the bait oligonucleotide. In some embodiments, the molecular tag includes one or more moieties. In some embodiments, the moiety includes a label as described herein. The label can allow detection of the hybridization of a bait oligonucleotide to an analyte. In some embodiments, the label is directly associated with (i.e., conjugated to) the bait oligonucleotide. The detectable label can be directly detectable by itself (e.g., radioisotope labels or fluorescent labels) or, in the case of an enzymatic label, can be indirectly detectable, e.g., by catalyzing chemical alterations of a chemical substrate compound or composition, which chemical substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

In some embodiments, the molecular tag includes a small molecule. In some embodiments, the molecular tag includes a nucleic acid. In some embodiments, the nucleic acid is single-stranded. In some embodiments, the nucleic acid is double-stranded. In some embodiments, the nucleic acid is RNA. In some embodiments, the nucleic acid is DNA. In some embodiments, the molecular tag includes a carbohydrate. In some embodiments, the molecular tag is positioned 5' to the domain in the bait oligonucleotide. In some embodiments, the molecular tag is position 3' to the domain in the bait oligonucleotide.

In some embodiments, the agent that binds specifically to the molecular tag includes a protein. In some embodiments, the protein is an antibody. In some embodiments, the agent that binds specifically to the molecular tag comprises a nucleic acid. In some embodiments, the agent that binds specifically to the molecular tag comprises a small molecule. In some embodiments, the agent that binds specifically to the molecular tag is attached to a substrate. In some embodiments, the substrate is a bead. In some embodiments, the substrate is a well. In some embodiments, the substrate is a slide.

In some embodiments, the moiety is biotin. In some embodiments, a biotin molecule is directly associated with (i.e., conjugated to) the bait oligonucleotide at the 3' end. In some embodiments, a biotin molecule is directly associated with (i.e., conjugated to) the bait oligonucleotide at the 5' end. In some embodiments, and as disclosed below, the biotin molecule can be associated to (e.g. conjugated to) an avidin molecule, allowing pulldown of an analyte. In some embodiments, and as disclosed below, the biotin molecule can be associated to (e.g. conjugated to) a streptavidin molecule, allowing pulldown of an analyte.

In some embodiments, the bait oligonucleotide does not include a moiety affixed to the sequence (i.e., the bait oligonucleotide is a naked bait oligonucleotide).

(ii) Hybridization Methods

In some instances, nucleic acids from a single library of nucleic acids (i.e., a single sample) hybridize to the oligonucleotide baits. In some instances, prior to hybridization, the library of nucleic acids can be pooled from multiple samples. In some instances, at least 2, 3, 4, 5, 6, 7, 8, or more samples are pooled. In some instances, each library is multiplexed with barcodes that are specific to a certain pool of nucleic acids. In some instances, pool libraries are from the same cell or tissue type. In some instances, pool libraries are from different cell or tissue types.

In the setting of pooling multiple samples from different spots on one or more arrays, pooling calculations take into account the number of spots on an array covered by a tissue. In some instances, estimating the number of gene expression spots covered by tissue can be performed visually, or by using automated computation methods for a more accurate measurement. In the setting of an array having about 5000 spots, the number of spots covered by the sample on the array can be calculated by multiplying the percent coverage by the total number of gene expression spots (e.g., about 5000).

In some instances, during the step of pre-hybridization pooling of nucleic acids, universal blockers are added to the pool. In some instances, human Cot DNA is added to the pool. Human Cot DNA is enriched for repetitive, non-coding elements commonly found in genomic DNA. These repetitive sequences often lead to non-specific binding during hybridization reactions. Adding Cot DNA to these reactions reduces non-specific binding associated with these repetitive sequences to improve accuracy.

In some instances, the methods of bait oligonucleotide hybridization disclosed herein include various buffers and components to aid in nucleic acid capture. In some instances, the methods include a hybridization enhancer, a wash buffer, an equilibration buffer, a hybridization buffer or any combination thereof. Any of the buffers can be in a concentrated form that can be diluted to an appropriate concentration by one in the art using e.g., nuclease-free water. In some instances, the components include streptavidin beads. In some instances, the components include avidin beads.

In some embodiments, where RNA is the nucleic acid analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by a polymerase. For example, one or more primer sequences with sequence complementarity to one or more RNAs of interest can be used to amplify the one or more RNAs of interest, thereby selectively enriching these RNAs. In some embodiments, an oligonucleotide with sequence complementarity (e.g. a probe) to the complementary strand of captured RNA (e.g., cDNA) can bind to the cDNA. For example, biotinylated oligonucleotides with sequence complementary to one or more cDNA of interest binds to the cDNA and can be selected using biotinylation-strepavidin affinity using any of a variety of methods known to the field (e.g., streptavidin beads). Other non-nucleic acid affinity moieties are known in the art, for example, 2-(4-Hydroxyphenylazo)benzoic acid (HABA) or a compound listed in Table 5.

TABLE 5

Affinity Moieties

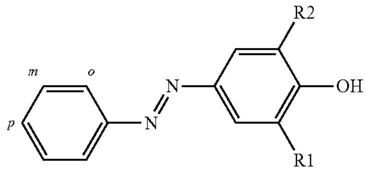

| Compound | -COO- Position | R1 | R2 |
|---|---|---|---|
| HABA | ortho | H | terei |
| 1b | meta | H | H |
| 1c | para | H | H |
| 2b | meta | H | $NO_2$ |
| 2c | para | H | $NO_2$ |
| 4a | ortho | $CH_3$ | $CH_3$ |
| 4b | meia | $CH_3$ | $CH_3$ |
| 4c | para | $CH_3$ | $CH_3$ |
| 5a | ortho | H | OH |
| 5b | meta | H | OH |
| 5c | para | H | OH |
| 6b | meta | OH | CH3 |
| 6c | para | OH | CH3 |

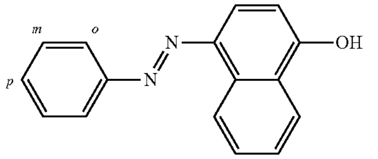 [SMILES: Oc1ccc(/N=N/c2ccccc2)c2ccccc12]

| Compound | -COO- Position |
|---|---|
| 3a | ortho |
| 3b | meta |
| 3c | para |

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Subsequent application of the capture probes to the sample can result in improved capture of other types of RNA due to the reduction in non-specific RNA present in the sample.

(1) Hybridization of Bait Oligonucleotides Directly

After creation of a plurality of nucleic acids or a library generated using the same, one or more nucleic acids of interest can be enriched using one or more bait oligonucleotides.

In some embodiments, bait oligonucleotides are added to a plurality of nucleic acids (e.g., a library of nucleic acids). In some embodiments, the plurality of nucleic acids includes nucleic acids that have a spatial barcode or a complement thereof, and a portion of a sequence of an analyte from a biological sample, or a complement thereof. In some embodiments, the spatial barcode includes a sequence that corresponds to a region of interest in the biological sample. In some embodiments, the spatial barcode allows detection of and association with a particular region of interest in the biological sample. In some embodiments, the methods disclosed herein include identifying the region of interest. In some embodiments, the spatial barcode provides information about the location of an analyte in a biological sample. In some embodiments, the methods disclosed herein include identifying the location and/or abundance of an analyte in the biological sample.

In some embodiments, the bait oligonucleotides are added to a plurality of nucleic acids. In some embodiments, bait oligonucleotides include a domain that binds specifically to all or a portion of a spatial barcode or a complement thereof, and/or all or a portion of a sequence of an analyte or a complement thereof. In some embodiments, a complex of a bait oligonucleotide specifically bound to the nucleic acid can be enriched. For example, a bait oligonucleotide can include a molecular tag, and a complex of a bait oligonucleotide specifically bound to the nucleic acid can be enriched using an agent that binds specifically to the molecular tag. In some embodiments, the molecular tag can be attached (directly or indirectly) to a substrate (e.g., a slide, a well, or a bead). In some embodiments, a molecular tag can include a protein, a nucleic acid, a carbohydrate, a small molecule, or any combination thereof. In some embodiments, an agent that binds specifically to a molecular tag can be a protein, a nucleic acid, a carbohydrate, a small molecule, or any combination thereof. In some embodiments, a molecular tag can be avidin and an agent that binds specifically to the molecular tag can be biotin. In some embodiments, a molecular tag can be streptavidin and an agent that binds specifically to the molecular tag can be biotin.

In some embodiments, a molecular tag can be biotin and an agent that binds specifically to the molecular tag can be avidin or streptavidin (e.g., streptavidin attached to a bead). In some instances, beads are prepared using methods known in the art. In some instances, buffers (e.g., equilibration buffer) is used to suspend the bead. In some instances, the beads are separated from the buffer using methods known in the art (e.g., using a magnetic separator; centrifugation). In some instances, beads are resuspended in a buffer to be used to capture bait oligonucleotides.

In some embodiments, where the molecular tag is biotin and the method includes the use of avidin or streptavidin beads to enrich a nucleic acid complexed with a bait oligonucleotide, the streptavidin beads can be washed using any method known in the art. In some embodiments, the streptavidin bead can be washed for 1 time, 2 times, 3 times, 4 times, 5 times, 6 times, 7 times or more. In some embodiments, the streptavidin beads can be stringently washed for one time, 2 times, 3 times, 4 times, 5 times, 6 times, 7 times, or more. In some embodiments, the streptavidin beads can be washed at about 15° C., about 20° C., about 25° C., about 30° C., about 35° C., about 40° C., about 45° C., about 48° C., about 50° C., about 55° C., about 60° C., about 62° C., about 65° C., about 67° C., about 70° C., about 75° C. or more. In some embodiments, the streptavidin beads can be washed at about 67° C. In some instances, the temperature of the avidin or streptavidin bead wash is at the same temperature (e.g., 60° C. or 65° C.) as the bait oligonucleotide hybridization step. In some embodiments, after one or more wash steps, the nucleic acid(s) hybridized to the bait oligonucleotide(s) can be recovered and are enriched.

In some embodiments, the recovered nucleic acids can be released from the bait oligonucleotide(s) and purified to remove avidin or streptavidin and biotin (or any other molecular tag and agent that binds specifically to the molecular tag).

In some embodiments, a molecular tag can be biotin and an agent that binds specifically to the molecular tag can be avidin (e.g., avidin attached to a bead). In some embodiments, where the molecular tag is biotin and the method includes the use of avidin beads to enrich a nucleic acid complexed with a bait oligonucleotide, the avidin beads can be washed using any method known in the art. In some embodiments, the avidin bead can be washed for 1 time, 2 times, 3 times, 4 times, 5 times, 6 times, 7 times or more. In some embodiments, the avidin beads can be stringently washed for one time, 2 times, 3 times, 4 times, 5 times, 6 times, 7 times, or more. In some embodiments, the avidin beads can be washed at about 15° C., about 20° C., about 25° C., about 30° C., about 35° C., about 40° C., about 45° C., about 48° C., about 50° C., or more. In some embodiments, after one or more wash steps, the nucleic acid(s) hybridized to the bait oligonucleotide(s) can be recovered and are enriched. In some embodiments, a plurality of bait oligonucleotides can be used in any of the methods described herein to enrich one or more nucleic acids of interest from a plurality of nucleic acids. In some embodiments, the plurality of bait oligonucleotides are designed to enrich one or more nucleic acids that include all or a part of a sequence of an analyte of interest (e.g., one or more genes that function or are aberrantly expressed in a particular cellular state or pathway), or a complement thereof. For example, in some embodiments, a plurality of bait oligonucleotides can be used to enrich nucleic acids that include all or a part of a sequence of cancer-related transcripts, or complements thereof (e.g., as disclosed in U.S. Appl. No. 62/970,066 (Titled "Capturing Targeted Genetic Targets Using A Hybridization/Capture Approach") and U.S. Appl. No. 62/929,686, (Titled "Capturing Targeted Genetic Targets Using A Hybridization/Capture Approach"), each of which is incorporated by reference in its entirety). In some embodiments, a plurality of bait oligonucleotides can be used to enrich nucleic acids that include all or a part of a sequence of immune-related transcripts, or complements thereof (e.g., as disclosed in U.S. Appl. No. 62/970,066 (Titled "Capturing Targeted Genetic Targets Using A Hybridization/Capture Approach") and U.S. Appl. No. 62/929,686, (Titled "Capturing Targeted Genetic Targets Using A Hybridization/Capture Approach"), each of which is incorporated by reference in its entirety). In some embodiments, a plurality of bait oligonucleotides can be used to enrich nucleic acids that include all or a part of a sequence of pathway-specific transcripts, or complements thereof (e.g., as disclosed in U.S. Appl. No. 62/970,066 (Titled "Capturing Targeted Genetic Targets Using A Hybridization/Capture Approach") and U.S. Appl. No. 62/929,686, (Titled "Capturing Targeted Genetic Targets Using A Hybridization/Capture Approach"), each of which is incorporated by reference in its entirety). In some embodiments, a plurality of bait oligonucleotides can be used to enrich nucleic acids that include all or a part of a sequence of neurological-specific transcripts, or complements thereof, as listed in Table 4.

In some embodiments, after hybridization of one or more bait oligonucleotides to their target nucleic acids, the hybridized nucleic acids are enriched, creating a pool of nucleic acids that are enriched for particular nucleic acids of interest. In some instances, after hybridization and binding to the streptavidin or avidin beads, unhybridized nucleic acids are washed from the sample, thus enriching nucleic acids of interest. In some embodiments, after hybridization of one or more bait oligonucleotides to their target nucleic acids, the unhybridized nucleic acids are degraded (e.g., by a nuclease), thus enriching the hybridized nucleic acids. In some embodiments, after hybridization of one or more bait oligonucleotides, the hybridized nucleic acids are degraded (e.g., by a nuclease), thus enriching the un-hybridized nucleic acids; for example, this technique may be useful to decrease the amount of a high-abundance nucleic acid that is not of interest. In some embodiments, the bait oligonucleotides may not include a detectable moiety. In some embodiments, the enriched nucleic acids are purified. In some embodiments, the enriched nucleic acids are sample indexed (e.g., prior to sequencing).

In some embodiments, a bait oligonucleotide is hybridized with a nucleic acid at about 40° C., about 45° C., about 50° C., about 55° C., about 60° C., about 65° C., about 70° C., about 75° C., about 80° C. or higher. In some embodiments, the bait oligonucleotides are hybridized with a nucleic acid for at least 15 minutes, at least 30 minutes, at least 45 minutes, at least 1 hour, at least 90 minutes, at least 2 hours, at least 3 hours, at least 4 hours, at least 5 hours, or longer.

In some instances, the bait oligonucleotides are hybridized with a nucleic acid for about 2 hours. In some instances, the bait oligonucleotides are hybridized with a nucleic acid overnight (e.g., at least about 8 hours, about 9 hours, about 10 hours, about 11 hours, about 12 hours, or longer). In some instance, the bait oligonucleotides are hybridized with a nucleic acid for about 6 hours, about 7 hours, about 8 hours, about 9 hours, about 10 hours, about 11 hours, about 12 hours, or longer. In some instances, after hybridization, the sample comprising the hybridized bait oligonucleotides with the nucleic acids of interest is washed. In some instances, washing occurs using any wash solution described herein. In some instances, washing occurs at 65° C. In some instance, washing occurs at 60° C. In some instances, hybridization occurs overnight at 60° C. followed by subsequent wash steps at 60° C. In instances where the average length of a nucleic acid molecule is less than 700 base pairs, hybridization should be extended to overnight at 60° C. In this setting, subsequent washes are performed at 60° C. In instances where a library pool includes nucleic acid molecules of varying length (e.g., if the pool contains both short (e.g., <700 bp) and long (e.g., >700 bp)), hybridization can be extended to overnight at 60° C. with subsequent washes performed at 60° C. For example a percentage of the pool of nucleic acid molecules (e.g., about 10%, 20%, 30%, 40%, 50%, 60%, 70%, 80%, 90%) can be less than 700 base pairs, and thus this alternative method of overnight at 60° C. with subsequent washes performed at 60° C.

In some embodiments, one or more detectable moieties can be associated (e.g., attached directly or indirectly) with a bait oligonucleotide. In some embodiments, the one or more detectable moieties can be used to detect (or enhance detection) of a bait oligonucleotide (e.g., a bait oligonucleotide hybridized to a nucleic acid).

In some embodiments, the enriched nucleic acid can be amplified. After amplification, the enriched and amplified nucleic acid can be used to generate a library of nucleic acids and sequenced using any method known in the art, including the exemplary sequencing methods described herein. In some embodiments, sequencing can include determining all or a portion of the sequence of the spatial barcode or the complement thereof in the nucleic acid. In some embodiments, sequencing includes determining all or a portion of the sequence of the analyte from the biological sample or a complement thereof in the nucleic acid. In some embodiments, sequencing includes high throughput sequencing.

In some instances, the methods of amplification comprise steps that include compositions including a buffer and a set of library primers. A thermocycler can be used to amplify the enriched nucleic acid library (e.g., cycling steps of e.g., 98° C., 67° C., and 72° C.). It is appreciated that one skilled in the art can determine the temperature and run time parameters in order to amplify the nucleic acid library. In some instances, one can vary the number of total cycles of amplification in order to optimize detection of one or more bait oligonucleotides. In some instances, the number of PCR cycles run to amplify the library(-ies) is at least 9, 10, 11, 12, 13, 14, 15, 16, 17, 18, 19, 20, 21, 22, 23, 24, 25, 26, 27, 28, 29, 30, or more cycles. It is appreciated that if the expected expression of a given target is low, then more cycles will be necessary to detect the target. In some instances, amplification can be performed while the bead (e.g., avidin or streptavidin) is in the mixture. In some instances, the bead(s) can be removed using methods known in the art (e.g., using a magnet).

In some instances, the average fragment size of a nucleic acid in the library can be determined after amplification. In some instances, automated electrophoresis system (e.g., TapeStation from Agilent) can be run as quality control of the nucleic acid library samples. In some instances, one can analyze size, quantity, and integrity of samples before downstream analysis (e.g., sequencing).

In some embodiments, targeted spatial gene expression profiling using one or more panels as described herein (e.g., cancer panel, immune panel, pathway panel, or neuro panel) can enrich the target nucleic acids as compared to unbiased spatial profiling by about 1 fold, about 2 fold, about 3 fold, about 4 fold, about 5 fold, about 6 fold, about 7 fold, about 8 fold, about 9 fold, about 10 fold, about 20 fold, about 50 fold, about 100 fold or greater. In some embodiments, the targeted spatial gene expression profiling using one or more panels as described herein (e.g., the cancer panel, the immune panel, the pathway panel, or the neuro panel) can enrich the target nucleic acids per gene as compared to unbiased spatial profiling by about 1 fold, about 2 fold, about 3 fold, about 4 fold, about 5 fold, about 6 fold, about 7 fold, about 8 fold, about 9 fold, about 10 fold, about 20 fold, about 50 fold, about 100 fold or greater.

In some embodiments, the targeted spatial gene expression profiling using one or more panels as described herein (e.g., the cancer panel, the immune panel, the pathway panel, or the neuro panel) can increase on-target read percentage as compared to unbiased spatial profiling by about 1 fold, about 2 fold, about 3 fold, about 4 fold, about 5 fold, about 6 fold, about 7 fold, about 8 fold, about 9 fold, about 10 fold, about 20 fold, about 50 fold, about 100 fold or greater. In some embodiments, the number of on-target reads by targeted spatial gene expression profiling using one or more panels as described herein is at least 50%, at least 60%, at least 70%, at least 75%, at least 80%, at least 85%, at least 90%, or at least 95% as compared to that using unbiased spatial profiling. In some embodiments, the targeted spatial gene expression profiling using the panel as described herein (e.g., the cancer panel, the immune panel, the pathway panel, or the neuro panel) can decrease off-target read percentage as compared to unbiased spatial profiling by about 1 fold, about 2 fold, about 3 fold, about 4 fold, about 5 fold, about 6 fold, about 7 fold, about 8 fold, about 9 fold, about 10 fold, about 20 fold, about 50 fold, about 100 fold or greater.

In some embodiments, the targeted spatial gene expression profiling using one or more panels as described herein (e.g., the cancer panel, the immune panel, the pathway panel, or the neuro panel) enriches detection of a target analyte. In some embodiments, the targeted spatial gene expression profiling using one or more panels as described herein (e.g., the cancer panel, the immune panel, the pathway panel, or the neuro panel) enriches detection of one or more target analytes. In some embodiments, enrichment includes an increase in the number of sequencing reads that are detected when the plurality nucleic acids and/or probes are sequenced. In some embodiments, enrichment includes an increase in the number of sequencing reads that are detected when the nucleic acids are sequenced after avidin-biotin pulldown described herein. In some embodiments, enrichment includes an increase in the number of sequencing reads that are detected when the nucleic acids are sequenced after streptavidin-biotin pulldown described herein. In some embodiments, the increase is about 50%, about 55%, about 60%, about 62%, about 65%, about 70%, about 75%, about 80%, about 85%, about 90%, about 95%, about 1 fold, about 2 fold, about 3 fold, about 4 fold, about 5 fold, about 6 fold, about 7 fold, about 8 fold, about 9 fold, about 10 fold, about 20 fold, about 50 fold, about 100 fold or greater enrichment of target analyte sequence reads compared to the number of sequence reads in the same target analyte when performing whole genome sequencing.

In some embodiments, enriched target analyte sequence reads obtained from the targeted spatial gene expression profiling using one or more panels as described herein (e.g., the cancer panel, the immune panel, the pathway panel, or the neuro panel) is highly correlated with the sequence reads in the same biological sample when performing an unbiased (e.g., non-targeted) spatial gene expression profiling. In some embodiments, at least 50%, at least 60%, at least 70%, at least 80%, or at least 90% of the UMIs detected from the enriched target analyte sequence reads are matched to the sequence reads in the same biological sample when performing un unbiased (e.g., non-targeted) spatial gene expression profiling. In some embodiments, the R2 of the matched UMI counts is at least 0.95, at least 0.96, at least 0.97, at least 0.98, or at least 0.99.

In some embodiments, the number of reads per spot (reads/spot) obtained from the targeted spatial gene expression profiling using one or more panels as described herein (e.g., the cancer panel, the immune panel, the pathway panel, or the neuro panel) is less than 20%, less than 15%, less than 10%, less than 9%, less than 8%, less than 7%, less than 6%, less than 5%, less than 4%, less than 3%, less than 3%, less than 2%, or less than 1% as compared to that obtained from an unbiased (e.g., non-targeted) spatial gene expression profiling. In some embodiments, the total reads obtained from the targeted spatial gene expression profiling using one or more panels as described herein (e.g., the cancer panel, the immune panel, the pathway panel, or the neuro panel) is less than 20%, less than 15%, less than 10%, less than 9%, less than 8%, less than 7%, less than 6%, less than 5%, less than 4%, less than 3%, less than 3%, less than 2%, or less than 1% as compared to that obtained from an unbiased (e.g., non-targeted) spatial gene expression profiling. In some embodiments, even though the total reads, and/or reads/spot is decreased by the targeted spatial gene expression profiling using one or more panels as described herein, the biological pattern (e.g., the spatial pattern of a particular gene expression in a biological sample) is maintained as compared to that obtained from an unbiased (e.g., non-targeted) spatial gene expression profiling.

In some embodiments, the targeted spatial gene expression profiling using one or more panels as described herein (e.g., the cancer panel, the immune panel, the pathway panel, or the neuro panel) can have about 50%, about 55%, about 60%, about 62%, about 65%, about 70%, about 75%, about 80%, about 85%, about 90%, about 95%, or more of panel gene recovery relative to an unbiased (e.g., non-targeted) spatial gene expression profiling.

In some embodiments, the targeted spatial gene expression profiling using one or more panels as described herein (e.g., the cancer panel, the immune panel, the pathway panel, or the neuro panel) can have about 50%, about 55%, about 60%, about 62%, about 65%, about 70%, about 75%, about 80%, about 85%, about 90%, about 95%, or more of panel UMI recovery and/or UMI retention relative to an unbiased (e.g., non-targeted) spatial gene expression profiling. In some embodiments, the targeted spatial gene expression profiling using one or more panels as described herein (e.g., the cancer panel, the immune panel, the pathway panel, or the neuro panel) can reduce gene or UMI targeting complexity (or complexity) to about 90%, about 80%, about 70%, about 60%, about 50%, about 40%, about 30%, about 20% or less of an unbiased (e.g., non-targeted) spatial gene expression profiling.

In some embodiments, dual-indexed libraries can be used for targeted spatial gene expression profiling. In some embodiments, individually indexed libraries can be mixed before the enrichment step by hybridization/capture to generate a targeted library for downstream high-throughput sequencing. In some embodiments, individually indexed libraries can be mixed after the enrichment step by hybridization/capture to generate a targeted library for downstream high-throughput sequencing. In some embodiments, the targeted spatial gene expression profiling using one or more panels as described herein provides comparable, even more detailed spatial gene profiling results as compared to those obtained from a pathologist's annotation, and/or an unbiased (e.g., non-targeted) spatial gene expression profiling.

(2) Hybridization of Bait Oligonucleotides Directly to Analytes of Interest.

In some embodiments, a bait oligonucleotide (e.g., a set of bait oligonucleotides from one or more panels as disclosed herein) can be added directly to an analyte. In some embodiments, the bait oligonucleotide is directly associated with (i.e., conjugated to) a detectable moiety or a molecular tag at the 3' end. In some embodiments, the bait oligonucleotide is directly associated with (i.e., conjugated to) a detectable moiety or a molecular tag at the 5' end. In some embodiments, the detectable moiety is a fluorophore or a radioisotope.

In some embodiments, target-specific reactions are performed in the biological sample. In some embodiments, a nucleic acid analyte can be denatured to create single-stranded analytes before contact with a bait oligonucleotide. In some embodiments, a bait oligonucleotide binds (e.g., hybridizes) directly to an analyte (e.g., a single-stranded analyte), and the detectable moiety (e.g., the fluorophore) can be identified using one or more imaging techniques. In some embodiments, target-specific reactions include in situ hybridization of the bait oligonucleotide to an analyte (e.g., a single-stranded analyte). In some embodiment, the in situ hybridization is fluorescence in situ hybridization (FISH). In some embodiments, the fluorophore or a molecular tag can serve as a marker to identify (e.g., enrich) an analyte of interest. In some embodiments, fluorescence microscopy can be used to locate a fluorophore-labelled bait oligonucleotide in a biological sample or elsewhere. In some embodiments, analytes not hybridized to a bait oligonucleotide can be washed away. In some embodiments, the wash methods include isolating only those analytes that fluoresce. In some embodiments, the wash steps include any of the wash steps provided herein.

In some embodiments, a fluorophore (e.g., any of the fluorophores disclosed herein) can be directly associated to (e.g., conjugated to) a bait oligonucleotide. In some embodiments, a bait oligonucleotide can include a non-fluorescent moiety that is directly associated to (e.g., conjugated to) the bait oligonucleotide. In some embodiment, a fluorophore can bind to the non-fluorescent moiety, thereby enhancing detection of the analyte.

In some embodiments, the fluorescence in situ hybridization methods disclosed herein detect a particular set of transcripts. In some embodiments, fluorescence in situ hybridization methods disclosed herein detect cancer-related transcripts (e.g., as disclosed in U.S. Appl. No. 62/970,066 (Titled "Capturing Targeted Genetic Targets Using A Hybridization/Capture Approach") and U.S. Appl. No. 62/929,686, (Titled "Capturing Targeted Genetic Targets Using A Hybridization/Capture Approach"), each of which is incorporated by reference in its entirety). In some embodiments, fluorescence in situ hybridization methods disclosed herein detect immune-related transcripts (e.g., as disclosed in U.S. Appl. No. 62/970,066 (Titled "Capturing Targeted Genetic Targets Using A Hybridization/Capture Approach") and U.S. Appl. No. 62/929,686, (Titled "Capturing Targeted Genetic Targets Using A Hybridization/Capture Approach"), each of which is incorporated by reference in its entirety). In some embodiments, fluorescence in situ hybridization methods disclosed herein detect pathway-specific transcripts (e.g., as disclosed in U.S. Appl. No. 62/970,066 (Titled "Capturing Targeted Genetic Targets Using A Hybridization/Capture Approach") and U.S. Appl. No. 62/929,686, (Titled "Capturing Targeted Genetic Targets Using A Hybridization/Capture Approach"), each of which is incorporated by reference in its entirety). In some embodiments, fluorescence in situ hybridization methods disclosed herein detect neurological-specific transcripts as described herein.

In some embodiments, a hybridized analyte/bait oligonucleotide complex can be cleaved from a substrate. In some embodiments, a spatially-barcoded array populated with a plurality of capture probes can be contacted with a biological sample. The spatially-barcoded capture probes can be cleaved and then interact with cells within a biological sample. In some embodiments, a capture probe of the plurality of capture probes can optionally include at least one cleavage domain. The cleavage domain represents the portion of the capture probe that is used to reversibly attach the capture probe to an array feature. Further, one or more segments or regions of a capture probe can optionally be released from the array feature by cleavage of the cleavage domain. As an example, spatial barcodes can be released by cleavage of a cleavage domain. In some embodiments, a capture probe can also include a cleavage site (e.g., a cleavage recognition site of a restriction endonuclease), a photolabile bond, a thermosensitive bond, or a chemical-sensitive bond. In some embodiments, once a spatially-barcoded capture probe is associated with a particular cell or analytes thereof, the biological sample can be optionally removed.

In some embodiments, a cleaved or enriched analyte/bait oligonucleotide complex can be purified prior to downstream steps (e.g., sequencing). Sequencing can be performed using any method known in the art, including the exemplary sequencing methods described herein. In some instances, the methods disclosed herein include sequencing of single indexed libraries. In some instances, the methods disclosed herein include sequencing of dual indexed libraries. In some instances, the libraries comprise standard Illumina paired-end constructs which include P5 and P7 sequences. For single indexed libraries, an 8 bp sample index sequence is incorporated as the i7 sample index sequence. For dual indexed libraries, 10 bp sample index sequences are incorporated as the i7 and i5 sample index sequences.

In some embodiments, sequencing of a nucleic acid includes determining all or a portion of a sequence of a spatial barcode or the complement thereof. In some embodiments, sequencing includes determining all or a portion of the sequence of the analyte from the biological sample or a complement thereof. In some embodiments, sequencing includes high throughput sequencing. In some embodiments, sequencing includes ligating or adding one or more of an adapter sequence or a complement thereof, a poly (GI) sequence or a complement thereof, a template switching oligonucleotide sequence or a complement thereof, a primer binding site or a complement thereof, to the nucleic acid.

In some embodiments, multiple bait oligonucleotides (e.g., two or more bait oligonucleotides) can be used to interrogate spatial gene expression in a biological sample via RNA-templated ligation.

(3) Downstream Application after Hybridization of Bait oligonucleotides

In some embodiments, the methods disclosed herein include post-capture amplification. In some instances, the hybridized library molecules that are bound to streptavidin or avidin beads can be amplified prior to downstream sequencing events. In some instances, primers (e.g., a P5 adapter and/or a P7 adaptor) are added to a nucleic acid sequence or an enriched nucleic acid sequence. In some embodiments, amplification is performed before bait oligonucleotide enrichment of a nucleic acid of interest. In some embodiments, amplification is performed after bait oligonucleotide enrichment of a nucleic acid of interest.

In some embodiments of methods provided here, RNA-templated ligation is used to interrogate spatial gene expression in a biological sample (e.g., an FFPE tissue section). In some aspects, the steps of RNA-templated ligation include: (1) hybridization of pairs of bait oligonucleotides to a nucleic acid (e.g., a single-stranded cDNA or RNA molecule); (2) ligation of adjacently annealed probe pairs in situ; (3) RNase H treatment that (i) releases RNA-templated ligation products from the tissue (e.g., into solution) and (ii) destroys unwanted DNA-templated ligation products; and optionally, (4) amplification of RNA-templated ligation products (e.g., by multiplex PCR).

In some aspects, RNA-templated ligation is used for detection of a target analyte, determination of sequence identity, and/or expression monitoring and transcript analysis. In some aspects, RNA-templated ligation allows for detection of a particular change in a nucleic acid (e.g., a mutation or single nucleotide polymorphism (SNP)), detection or expression of a particular nucleic acid, or detection or expression of a particular set of nucleic acids (e.g., in a similar cellular pathway or expressed in a particular pathology). In some embodiments, the methods that include RNA-templated ligation are used to analyze nucleic acids, e.g., by genotyping, quantitation of DNA copy number or RNA transcripts, localization of particular transcripts within samples, and the like. In some aspects, systems and methods provided herein that include RNA-templated ligation identify single nucleotide polymorphisms (SNPs). In some aspects, such systems and methods identify mutations.

In some aspects, disclosed herein are methods of detecting RNA expression that includes bringing into contact a first bait oligonucleotide, a second bait oligonucleotide, and a ligase (e.g., T4 RNA ligase). In some embodiments, the first bait oligonucleotide and the second bait oligonucleotide are designed to hybridize to a target sequence such that the 5' end of the first bait oligonucleotide and the 3' end of the second bait oligonucleotide are adjacent and can be ligated. After hybridization, the ligase (e.g., T4 RNA ligase) ligates the first bait oligonucleotide and the second bait oligonucleotide if the target sequence is present in the target sample, but does not ligate the first bait oligonucleotide and the second bait oligonucleotide if the target sequence is not present in the target sample. The presence or absence of the target sequence in the biological sample can be determined by determining whether the first and second bait oligonucleotides were ligated in the presence of ligase.

In some aspects, two or more RNA analytes are analyzed using methods that include RNA-templated ligation. In some aspects, when two or more analytes are analyzed, a first and a second bait oligonucleotide that is specific for each RNA analyte (e.g., specifically hybridizes to) are used.

In some aspects, three or more bait oligonucleotides are used in RNA-templated ligation methods provided herein. In some embodiments, the three or more bait oligonucleotides are designed to hybridize to a target sequence such that the three or more probes hybridize adjacent to each other such that the 5' and 3' ends of adjacent probes can be ligated. In some embodiments, the presence or absence of the target sequence in the biological sample can be determined by determining whether the three or more bait oligonucleotides were ligated in the presence of ligase.

(e) Compositions and Kits

Also provided herein are kits that include parts and instructions for performing the methods described herein. In some instances, the kits include a set of bait oligonucleotides. In some instances, the set of bait oligonucleotides is specific to a particular set of transcripts (e.g., a cancer panel, an immunology panel, a cellular pathway panel, or a neuroscience panel as disclosed herein). In some instances, the kit includes bait oligonucleotides specific for the cancer panel described herein. In some instances, the kit includes bait oligonucleotides specific for the immune panel described herein. In some instances, the kit includes bait oligonucleotides specific for the cellular pathway panel described herein. In some instances, the kit includes bait oligonucleotides specific for the neuro panel described herein. It is further appreciated that a custom panel can be designed using methods of designing bait oligonucleotides as described herein. In some instances, a kit includes multiple sets of baits for the same panel so that multiple (e.g., duplicate, triplicate) reactions can be run at the same time on the same slide. In some instances, additional bait oligonucleotides can be added to one of the panels described herein (e.g., the cancer panel, the immune panel, the pathway panel, or the neuro panel as disclosed herein). In some instances, the kit includes at least 2, 3, 4, 5, 6, 7, 8, 9, 10, 11, 12, 13, 14, 15, 16, 17, 18, 19, 20, 21, 22, 23, 24, or more reactions, wherein each reaction refers to the testing of one sample.

In some instances, a moiety (e.g., biotin) is adhered to each bait in the set of bait oligonucleotides. In some instances, the kit further includes streptavidin beads. In some instances, the kit further includes avidin beads. In some instances, the kit further includes an array comprising a plurality of capture probes (i.e., as described herein). The capture probes on the array each include a spatial barcode and a capture domain.

The kit can also include reagents for carrying out the methods disclosed herein. For example, in some instances, the kit includes reagents for carrying out reverse transcription reactions (e.g., a reverse transcriptase); nucleic acid quantification as described herein; addition of fragments to nucleic acid sequences; and nucleic acid clean up. In some instances, the kit includes reagents necessary to fix, stain, and destain the biological sample.

In some instances, the kit includes components that allow for multiple reactions. In some instances, the kit includes components that allow for target hybridization. In some instances, the components for target hybridization include one or more of universal blockers, hybridization buffer, hybridization enhancer, equilibrium buffer (concentrated or 1×), wash buffer (concentrated or 1×), primers, control samples, or any combination thereof. In some instances, the kit includes components for amplifying the library of nucleic acids. In some instances, the components for amplifying the library of nucleic acids includes a mixture that aids in amplification, primers, or any combination thereof.

In some instances, the kit further includes instructions for carrying out library preparation and nucleic acid detection using the methods described herein.

Also provided herein are systems for analyzing one or more biological analytes present in a biological sample comprising an array comprising a plurality of capture probes. Any of the capture probes described herein can be included in part of the system. In certain instances, the captures probes each comprise a spatial barcode and a capture domain. In some instances, the system includes a composition (e.g., an enzyme) that can cleave the probe from the array. In some instances, cleavage of the probe occurs after hybridization of the probe to the analyte.

In some instances, the system includes a set of bait oligonucleotides that are specific for targets of interest. In some instances, the system includes bait oligonucleotides specific for the cancer panel described herein. In some instances, the system includes bait oligonucleotides specific for the immune panel described herein. In some instances, the system includes bait oligonucleotides specific for the pathway panel described herein. In some instances, the system includes bait oligonucleotides specific for the neuro panel described herein.

The system can also include reagents for carrying out the methods disclosed herein. For example, in some instances, the system includes reagents for carrying out reverse transcription reactions (e.g., a reverse transcriptase); nucleic acid quantification as described herein; addition of fragments to nucleic acid sequences; and nucleic acid clean up. In some instances, the system includes reagents necessary to fix, stain, and destain the biological sample.

In some instances, the system includes a reagent delivery system. The reagent delivery system includes instrumentation that allows the delivery of reagents to discrete portions of the biological sample, maintaining the integrity of the spatial patterns of the addressing scheme. In some instances, reagent delivery systems of the present assay systems comprise optional imaging means, reagent delivery hardware and control software. Reagent delivery can be achieved in a number of different ways. It should be noted that reagents may be delivered to many different biological samples at one time. A single tissue section has been exemplified herein; however, multiple biological samples may be manipulated and analyzed simultaneously. For example, serial sections of a tissue sample can be analyzed in parallel and the data combined to build a 3D map. In one exemplary aspect, the reagent delivery system may be a flow-based system. The flow-based systems for reagent delivery in the present invention can include instrumentation such as one or more pumps, valves, fluid reservoirs, channels, and/or reagent storage cells.

Also provided herein are compositions that include a bait oligonucleotide bound to a nucleic acid, wherein the nucleic acid comprises (i) a spatial barcode or a complement thereof, and (ii) a portion of an analyte binding moiety barcode, or a complement thereof. In some instances, the composition is an intermediate composition that is produced by the methods disclosed herein.

The bait oligonucleotide can be any bait oligonucleotide described herein. In some instances, the bait oligonucleotide is bound to the nucleic acid by a capture domain that binds specifically (i) all of a portion of the nucleic acid, and/or (ii) all or a portion of the analyte binding moiety barcode, or a complement thereof.

In some instances, the composition described herein further includes a molecular tag. In some instances, the composition further includes an agent that binds specifically to the molecular tag. The molecular tag can be any suitable molecular tag described herein. In some instances, the molecular tag comprises a protein. In some instances, the protein is streptavidin, avidin, or biotin. In some instances, the molecular tag includes a small molecule. In some instances, the molecular tag includes a nucleic acid. In some instances, the molecular tag includes a carbohydrate.

In some instances, the molecular tag is positioned 5' to the domain in the bait oligonucleotide. In some instance, the molecular tag is position 3' to the domain in the bait oligonucleotide.

The agent that binds specifically to the molecular tag can be any suitable agent described herein. In some instances, the agent includes streptavidin, avidin, or biotin. In some instances, the molecular tag includes a biotin, and the agent that binds specifically to the molecular tag includes an avidin. In some instances, the molecular tag includes a biotin, and the agent that binds specifically to the molecular tag includes a streptavidin. In some instances, the molecular tag includes an avidin, and the agent that binds specifically to the molecular tag includes a biotin. In some instances, the molecular tag includes a streptavidin, and the agent that binds specifically to the molecular tag includes a biotin.

In some instances, the agent that binds specifically to the molecular includes a protein. In some instances, the protein is an antibody. In some instances, the agent that binds specifically to the molecular tag includes a nucleic acid. In some instances, the agent that binds specifically to the molecular tag includes a small molecule.

In some instances, the composition described herein further includes a substrate. The substrate can be any suitable substrate described herein. In some embodiment, the agent that binds specifically to the molecular tag is immobilized on the substrate. In some embodiments, the molecular tag is immobilized on the substrate. In some instances, the substrate is a bead. In some instances, the substrate is a well. In some instances, the substrate is a slide.

EXEMPLARY EMBODIMENT

In some embodiments, disclosed herein is a method for identifying the location of a target analyte, e.g., a nucleic acid, in a biological sample, the method comprising (a) contacting a plurality of nucleic acids with a plurality of bait oligonucleotides, wherein a nucleic acid of the plurality of nucleic acids comprises (i) a spatial barcode or a complement thereof, and (ii) a portion of an analyte binding moiety barcode, or a complement thereof; with a bait oligonucleotide of the plurality of bait oligonucleotides comprising a domain that binds specifically to (i) all or a portion of a target sequence in the nucleic acid or a complement thereof, and a molecular tag; (b) capturing, and/or isolating a complex of the bait oligonucleotide specifically bound to the nucleic acid using a substrate comprising an agent that binds specifically to the molecular tag; and (c) determining (i) all or a portion of the sequence of the spatial barcode or the complement thereof, and (ii) all or a portion of the sequence of the analyte binding moiety barcode, and using the determined sequences of (i) and (ii) to identify the location of the analyte in the biological sample.

In some embodiments, disclosed herein is a method for enriching a target analyte, e.g., a nucleic acid, in a biological sample, the method comprising (a) contacting a plurality of nucleic acids with a plurality of bait oligonucleotides, wherein a nucleic acid of the plurality of nucleic acids comprises (i) a spatial barcode or a complement thereof, and (ii) a portion of an analyte binding moiety barcode, or a complement thereof; with a bait oligonucleotide of the plurality of bait oligonucleotides comprising a domain that binds specifically to (i) all or a portion of a target sequence in the nucleic acid or a complement thereof, and a molecular tag; (b) capturing, and/or isolating a complex of the bait oligonucleotide specifically bound to the nucleic acid using a substrate comprising an agent that binds specifically to the molecular tag, thereby enriching the analyte, e.g., the nucleic acid, in the biological sample.

In some embodiments, the analyte from the biological sample is associated with a disease or condition. In some embodiments, the domain of the bait oligonucleotide comprises a total of about 10 nucleotides to about 300 nucleotides. In some embodiments, the molecular tag comprises a protein. In some embodiments, the protein is biotin. In some embodiments, the molecular tag comprises a small molecule. In some embodiments, the molecular tag comprises a nucleic acid. In some embodiments, the molecular tag comprises a carbohydrate. In some embodiments, the molecular tag is positioned 5' to the domain in the bait oligonucleotide. In some embodiments, the molecular tag is position 3' to the domain in the bait oligonucleotide. In some embodiments, the agent that binds specifically to the molecular tag comprises a protein. In some embodiments, the protein is an antibody. In some embodiments, the agent that binds specifically to the molecular tag comprises streptavidin or avidin. In some embodiments, the agent that binds specifically to the molecular tag is attached to a substrate. In some embodiments, the substrate is a bead, a slide, or a well. In some embodiments, the nucleic acid is DNA. In some embodiments, the nucleic acid further comprises a primer binding sequence or a complement thereof. In some embodiments, the nucleic acid further comprises a unique molecular sequence or a complement thereof. In some embodiments, the nucleic acid further comprises an additional primer binding sequence or a complement thereof.

In some embodiments, the biological sample is a tissue sample. In some embodiments, the tissue sample is a formalin-fixed, paraffin-embedded (FFPE) tissue sample or a frozen tissue sample. In some embodiments, the biological sample was previously stained using a detectable label. In some embodiments, the biological sample was previously stained using hematoxylin and eosin (H&E). In some embodiments, the biological sample is a permeabilized biological sample. In some embodiments, the permeabilized biological sample has been permeabilized with a permeabilization agent. In some embodiments, the permeabilization agent is selected from an organic solvent, a cross-linking agent, a detergent, and an enzyme, or a combination thereof.

In some embodiments, the permeabilization agent is selected from an organic solvent, a cross-linking agent, a detergent, and an enzyme, or a combination thereof. In some embodiments, the analyte is an RNA molecule. In some embodiments, the RNA molecule is an mRNA molecule. In some embodiments, the determining in step (c) comprises sequencing (i) all or a portion of the sequence of the spatial barcode or the complement thereof, and (ii) all or a portion of the sequence of the analyte binding moiety barcode. In some embodiments, the sequencing is high throughput sequencing. In some embodiments, the sequencing comprises ligating an adapter to the nucleic acid.

In some embodiments, the method further comprises generating the plurality of nucleic acids comprises: (a) contacting a plurality of an analyte capture agents to the biological sample disposed on a substrate, wherein: an analyte capture agent of the plurality of the analyte capture agents comprises (i) an analyte binding moiety that binds specifically to the analyte, (ii) the analyte binding moiety barcode; and (iii) an analyte capture sequence; and the substrate comprises a plurality of capture probes, wherein a capture probe of the plurality comprises a spatial barcode and a capture domain, wherein the capture domain binds specifically to the analyte capture sequence; and (b) extending a 3' end of the capture probe using the analyte binding moiety barcode as a template to generate an extended capture probe; and (c) amplifying the extended capture probe to produce the nucleic acid. In some embodiments, the amplifying is isothermal. In some embodiments, the produced nucleic acid is released from the extended capture probe. In some embodiments, the analyte is an analyte that is dysregulated or differentially expressed in a cancer cell. In some embodiments, the analyte is an analyte that is dysregulated or differentially expressed in an immune cell. In some embodiments, the analyte is an analyte that is dyregulated in a cellular signaling pathway. In some embodiments, the analyte is an analyte that is dyregulated or differentially expressed in a neurological cell.

EXAMPLES

Example 1: Targeted Spatial Gene Expression

Figure 7:
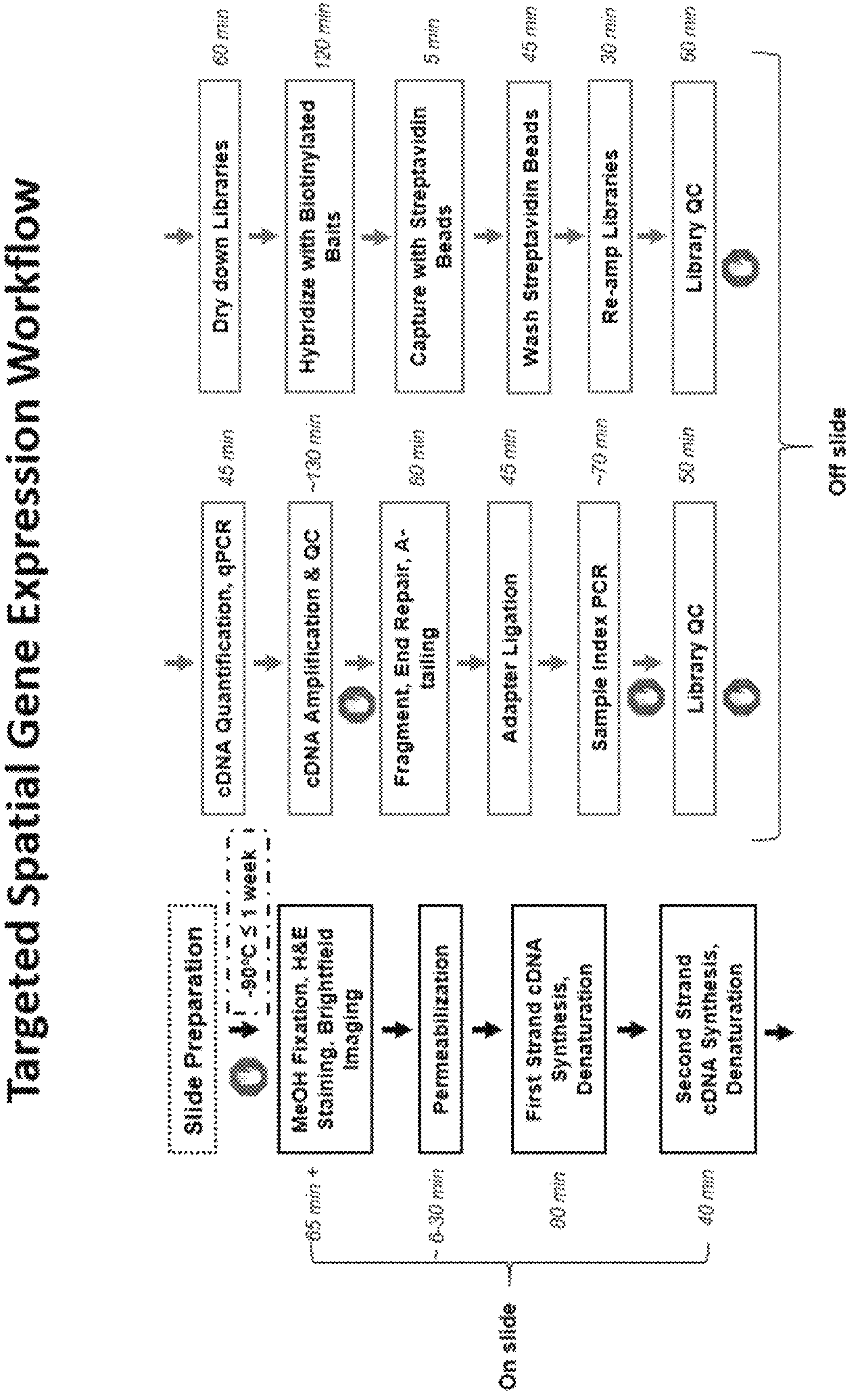
FIG. 7 is a workflow schematic showing the targeted spatial gene expression.

An exemplary targeted spatial gene expression workflow is shown in FIG. 7. Generally, a slide with a tissue affixed thereon is stored at −80° C. for less than a week. After thawing, the biological sample is fixed in methanol, and stained using H&E (Haemotoxylin and Eosin), imaged using bright field microscopy and permeabilized.

After gaining access to intracellular analytes (e.g., mRNA) via permeabilization, the analytes are captured via the capture probes affixed to the slide and, in this case first and second strand cDNA synthesis occurs wherein the second strand cDNA can be used as a proxy for the captured analyte (e.g. mRNA). After cDNA synthesis, the double-stranded analytes (e.g., cDNA molecules) are denatured and transferred from the slide and quantified by qPCR. After quantifying the cDNA, the cDNA analytes are fragmented and end-repaired. Adapters are ligated to the cDNA molecules and sample index (SI) PCR is performed. After SI-PCR, the library as prepared above can be dried down.

Panels that include bait oligonucleotides specific for cancer targets, immune targets, pathway targets, or neurological targets are hybridized to the cDNA analytes. The bait oligonucleotides are associated with biotin. After hybridization of the cDNA analytes to the biotinylated bait oligonucleotide, the biotinylated baits are captured with avidin or streptavidin beads. After a wash step to remove unbound analytes, the retaining library is re-amplified as a new nucleic acid library. The purified targeted library pool is then sequenced.

Figure 8A:
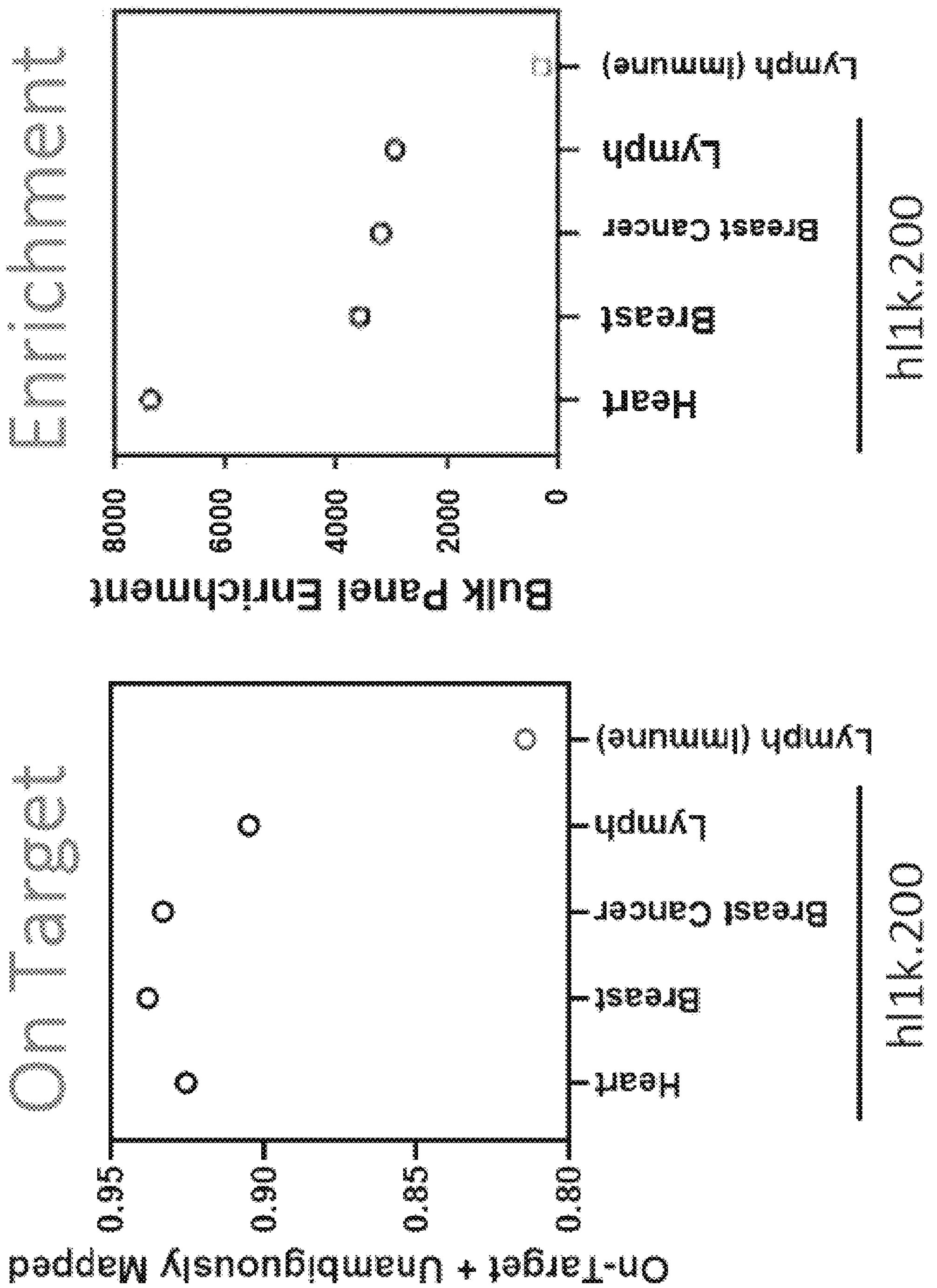
FIGS. 8A-8B show the on-target, the enrichment, and the complexity values wherein different spatial libraries were used. The spatial libraries included samples from heart, breast, breast cancer, or lymph. Either the hLlk_200.1 panel or the Immune panel were used.
Figure 8B:
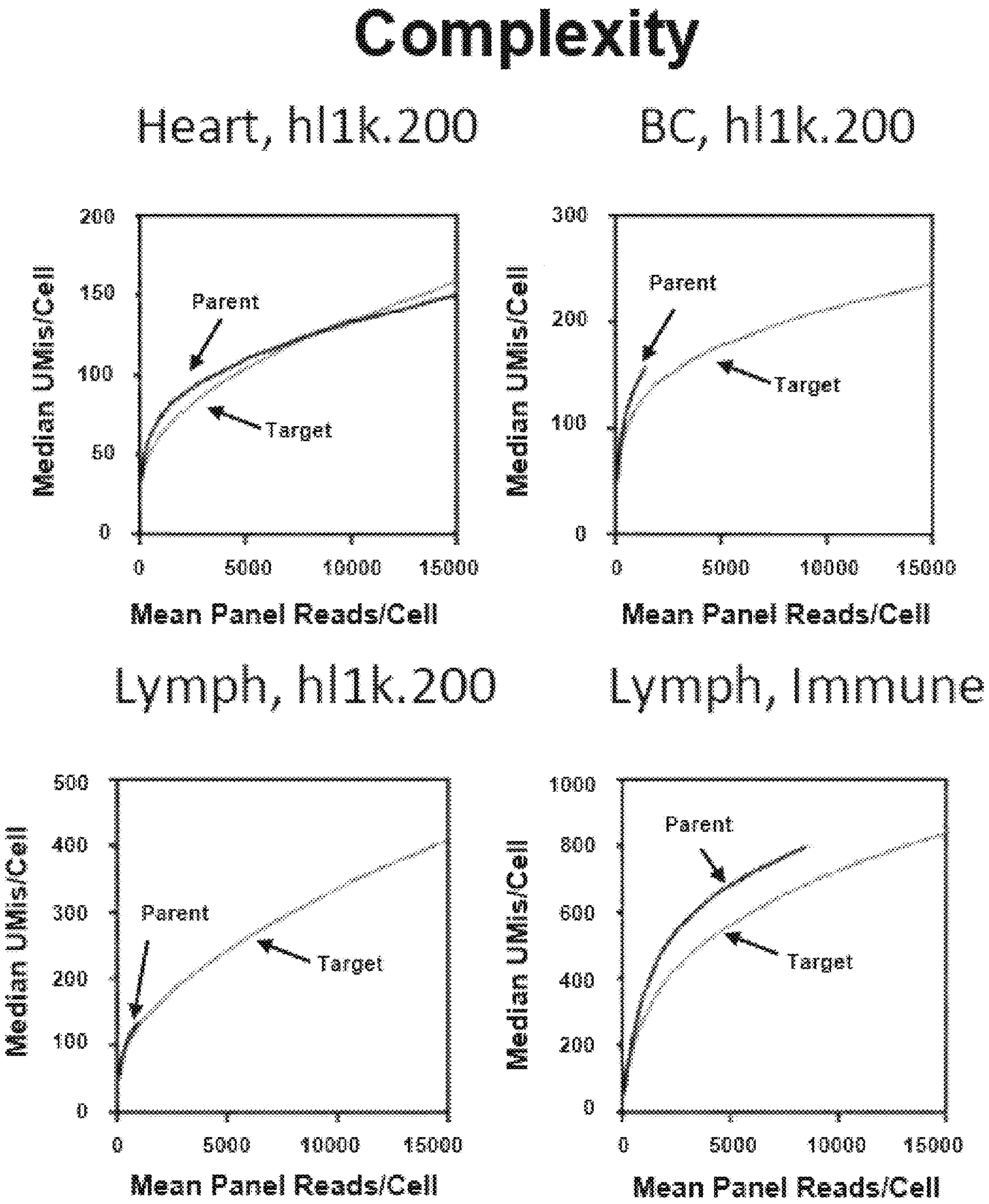

As shown in FIGS. 8A-8B, using two different panels (a 200-gene cancer panel (i.e., hl1k.200) and a 400-gene immune panel), spatial libraries from multiple samples (i.e., heart, breast, breast cancer, and lymph) showed very high on-target and mapped read percentage, enrichment, and UMI complexity (relative to the parent sample). These data demonstrate that the panels disclosed herein for targeted hybridization enrichment methods, are compatible with prepared spatial libraries.

Example 2: Targeted Gene Capture

In another example, the steps of targeted oligonucleotide hybridization can be performed prior to the adapter ligation and SI-PCR steps.

Figure 9:
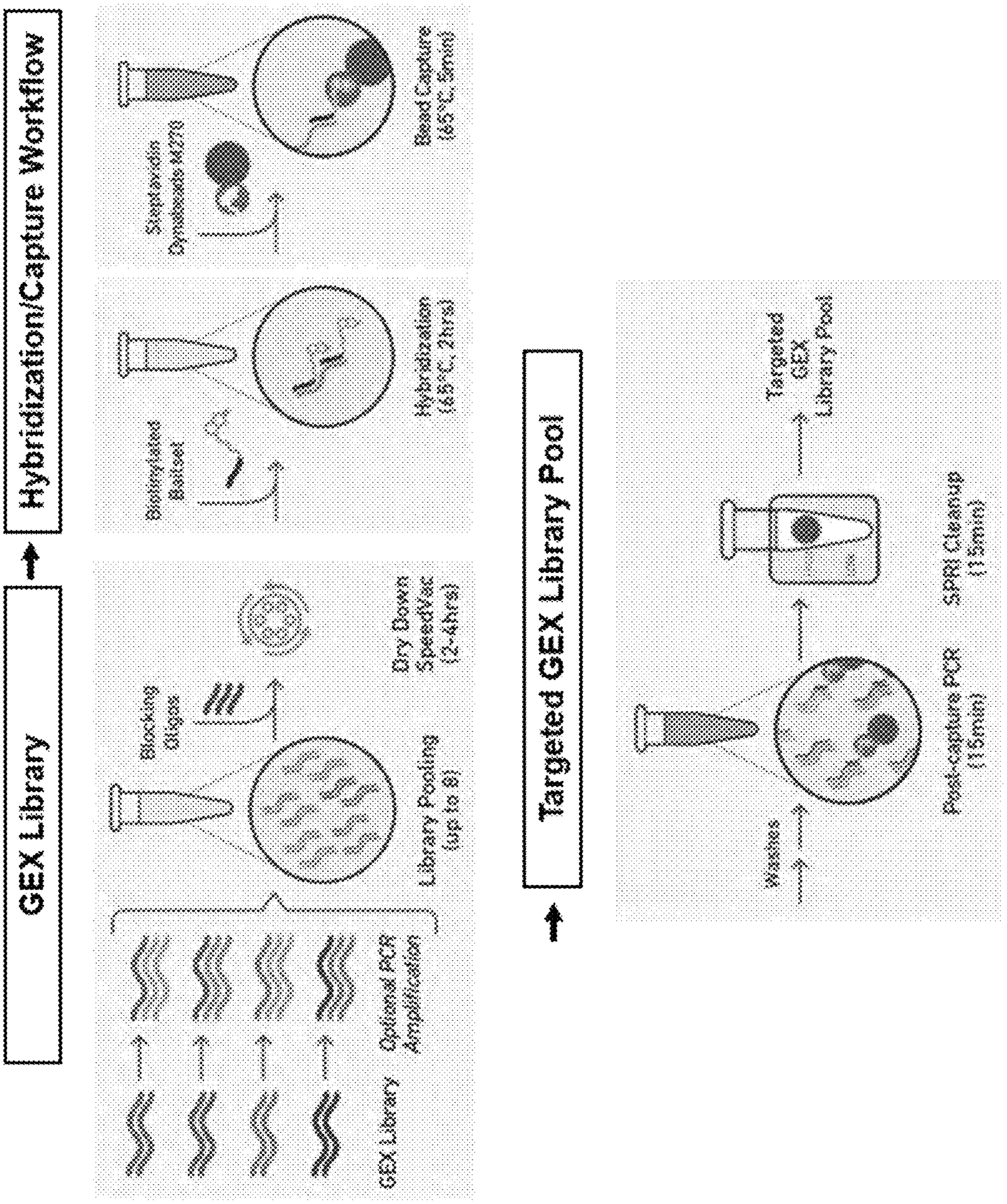
FIG. 9 is an exemplary workflow showing targeted spatial gene expression.

An exemplary workflow is shown in FIG. 9. The workflow utilizes a plurality of spatially generated library molecules obtained from gene expression library. Optionally, the library is amplified by PCR to increase the number of library molecules for targeted enrichment. In this example, up to 8 different libraries are pooled together prior to enrichment. Optionally, blocking oligos are hybridized to the libraries to prevent the modification of the targeted sequences, thus preventing downstream interference during sequencing applications. The pooled libraries are dried down for 2-4 hours in a SpeedVac, which allows samples to be dried under low pressure without heat. Biotinylated bait oligonucleotides are added and hybridized with the pooled library samples at 65° C. for 2 hours. Avidin- or streptavidin-coated beads are provided to capture the biotinylated oligonucleotide/targeted capture complexes at 65° C. for 5 minutes. Avidin or streptavidin beads are washed to remove any unbound sequence reads and post capture PCR is performed to reamplify the targeted library (e.g., to amplify the target sequences hybridized to the biotinylated oligonucleotide baits and subsequently captured by the avidin or streptavidin beads), followed by SPRI cleanup for 15 minutes. The purified targeted library pool is then sequenced.

Example 3: Hybridization and Capture Using Targeted Panel

Figure 10:
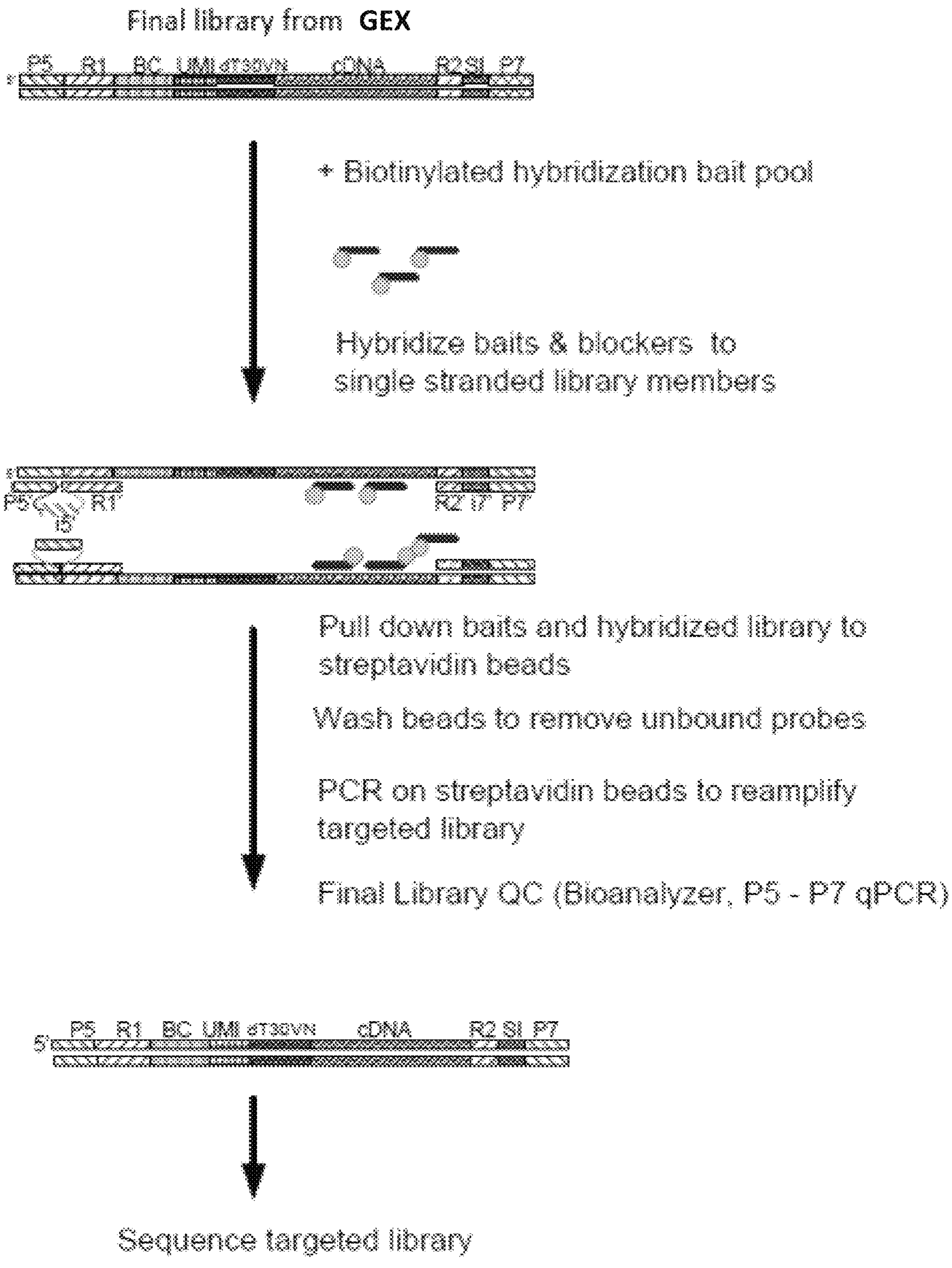
FIG. 10 is an exemplary workflow for hybridization and capture-based enrichment of targeted nucleic acid sequences using a spatial gene expression library.

An exemplary workflow of the hybridization and capture approach using a spatial gene expression library is shown in FIG. 10.

Specifically, a biological sample (e.g., a tissue section) is obtained using a suitable method described here, e.g., by cryo-sectioning of a tissue sample. The tissue section is then stained, e.g., by H&E staining, and imaged using any suitable method described herein (e.g., brightfield microscopy). The stained tissue section is then destained using an appropriate method described herein.

After the tissue section is imaged and destained, it is permeabilized and then contacted with an array comprising a plurality of capture probes. Each capture probe comprises a spatial barcode and a poly (T) sequence that hybridizes to the poly(A) tail of an mRNA analyte in the tissue section, thereby capturing multiple mRNA analytes on the array. The captured mRNAs are then reverse transcribed into cDNAs and amplified using a suitable method described herein. As a result, a cDNA library for spatial gene expression analysis is constructed (final library from GEX spatial array).

Subsequently, hybridization and capture using bait sets are performed. Blocking oligos are hybridized to the analytes in the library to prevent the modification of the sequencing related locations, thus preventing downstream interference during sequencing applications. The library is then dried down for 2-4 hours in a speedvac, which allows samples to be dried under low pressure without heat. The biotinylated bait sets are added to hybridize with the library samples at 65° C. for 2 hours. The avidin- or streptavidin-coated beads are provided to capture the biotinylated bait set-sequence read complexes at 65° C. for 5 minutes. The avidin or streptavidin beads are washed at 65° C. to remove any unbound sequence reads. In the alternative, biotinylated bait sets are added to hybridize with the library samples at 65° C. overnight (e.g., for at least 8 hours), and the avidin or streptavidin beads are washed at 60° C. to remove any unbound sequence reads. PCR is performed for 15 minutes on the avidin or streptavidin beads to reamplify the targeted library (e.g., to amplify the sequence reads hybridized to the biotinylated baits and subsequently captured by the avidin or streptavidin beads), followed by SPRI cleanup for 15 minutes. The purified targeted library pool is then sequenced.

Example 4: Mouse Tissues and Neuro Panel Spatial Transcriptomics

A mouse gliable panel of bait oligonucleotides was generated and targeted gene expression was performed on mouse brain tissue sections. Experiments were performed as described in the 10× Genomic Targeted Gene Expression-Spatial User Guide protocol, except mouse brain tissues were used in lieu of human tissue and mouse glia panel was used.

Figure 11:
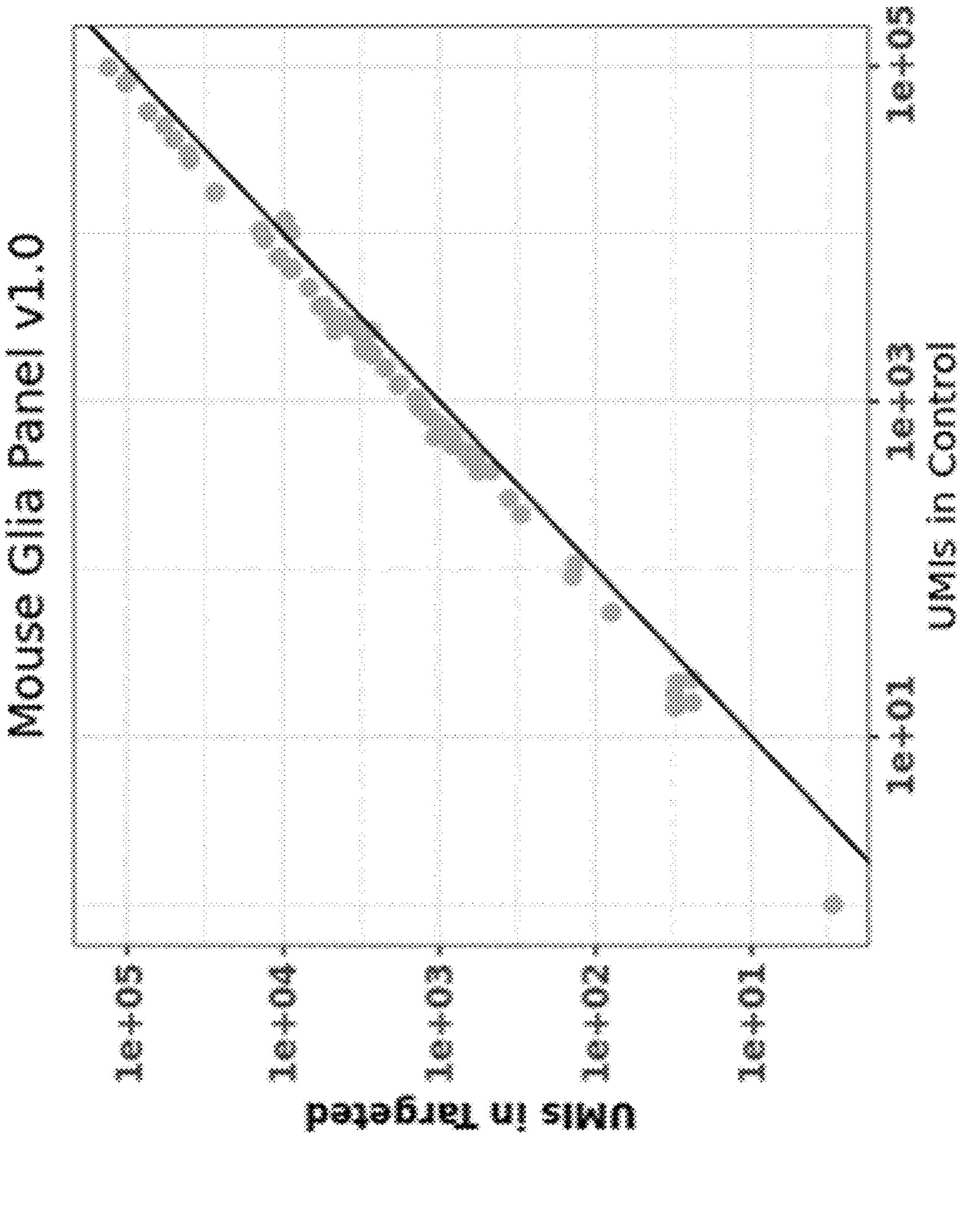
FIG. 11 is an exemplary graph showing the correlation between a mouse brain tissue spatial UMI count using a 65 gene targeted enrichment neuro panel (Y axis) as compared to a Visium control whole transcriptome analysis (X axis).
Figure 12B:
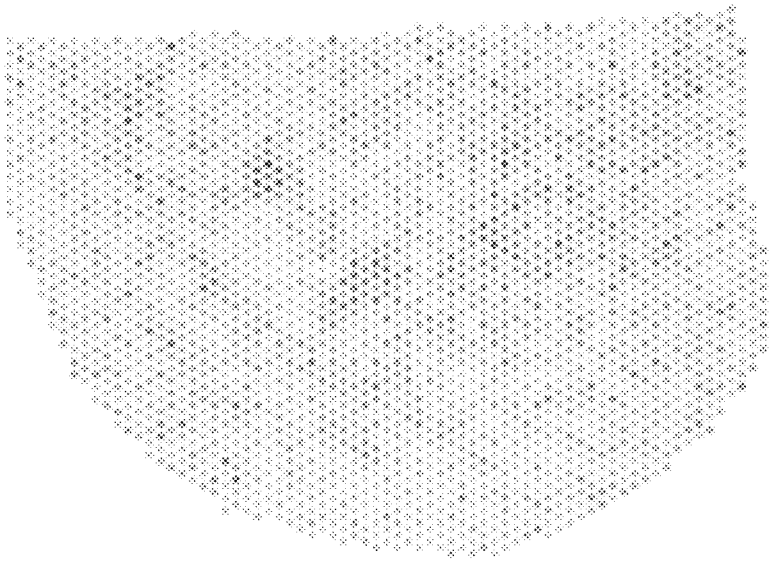
FIGS. 12A-12B are exemplary pictures demonstrating A) expression of the OLIG2 gene from a Visium whole transcriptome spatial array (control) and B) expression of the OLIG2 gene from a 65 gene targeted enrichment neuro panel. Pictures correlate to data of FIG. 11.
Figure 12A:
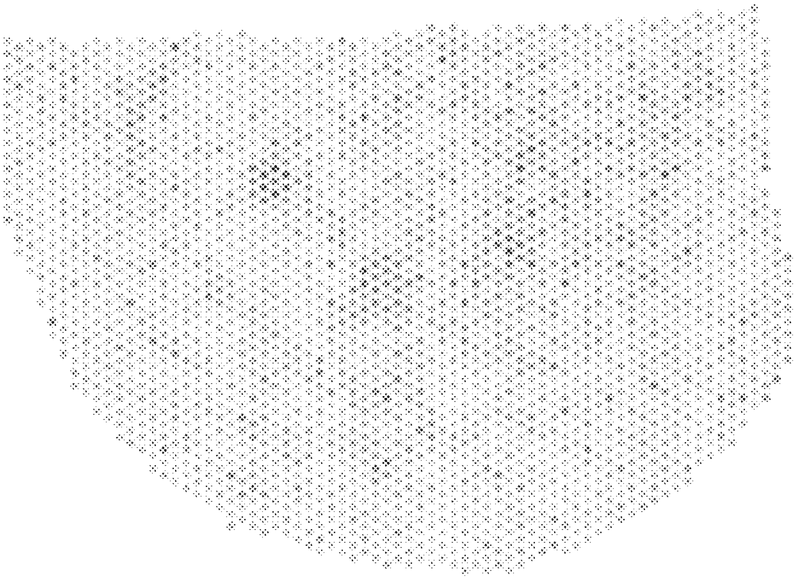

A whole transcriptome panel (control) versus a targeted 65 neuro gene mouse glia panel was run on a Visium array. As seen in FIG. 11, there is very high quality UMI efficiency of recovery and retention of the spatial distribution of the control (Visium whole transcriptome assay) versus the targeted gene panel. FIGS. 12A-12B show pictorially the OLIG2 spatial gene distribution in the control library (FIG. 12A) as compared to the OLIG2 gene in the targeted gene panel library (FIG. 12B). For the control, there were approximately 72 k reads/spot with 2211 UMI counts, whereas the targeted gene panel had approximately 3.5 k reads/spot with 3315 UMI counts. OLIG2 gene encodes the oligodendrocyte transcription factor 2 which is expressed in oligodendroglial brain cells, and in humans OLIG2 gene is expressed in oligodendroglial tumors of the brain. The results demonstrate that the same methods for targeted gene expression enrichment can also be performed using mouse bait oligonucleotides in mouse tissue samples.

Example 5: Targeted Gene Panels as Applied to Human Tissue Sections

Targeted gene panels were used to target capture gene expression in different human tissues from Visium arrays. Targeted gene expression methods were followed as described in the 10× Genomic Targeted Gene Expression Spatial User Guide protocol.

Figure 13A:
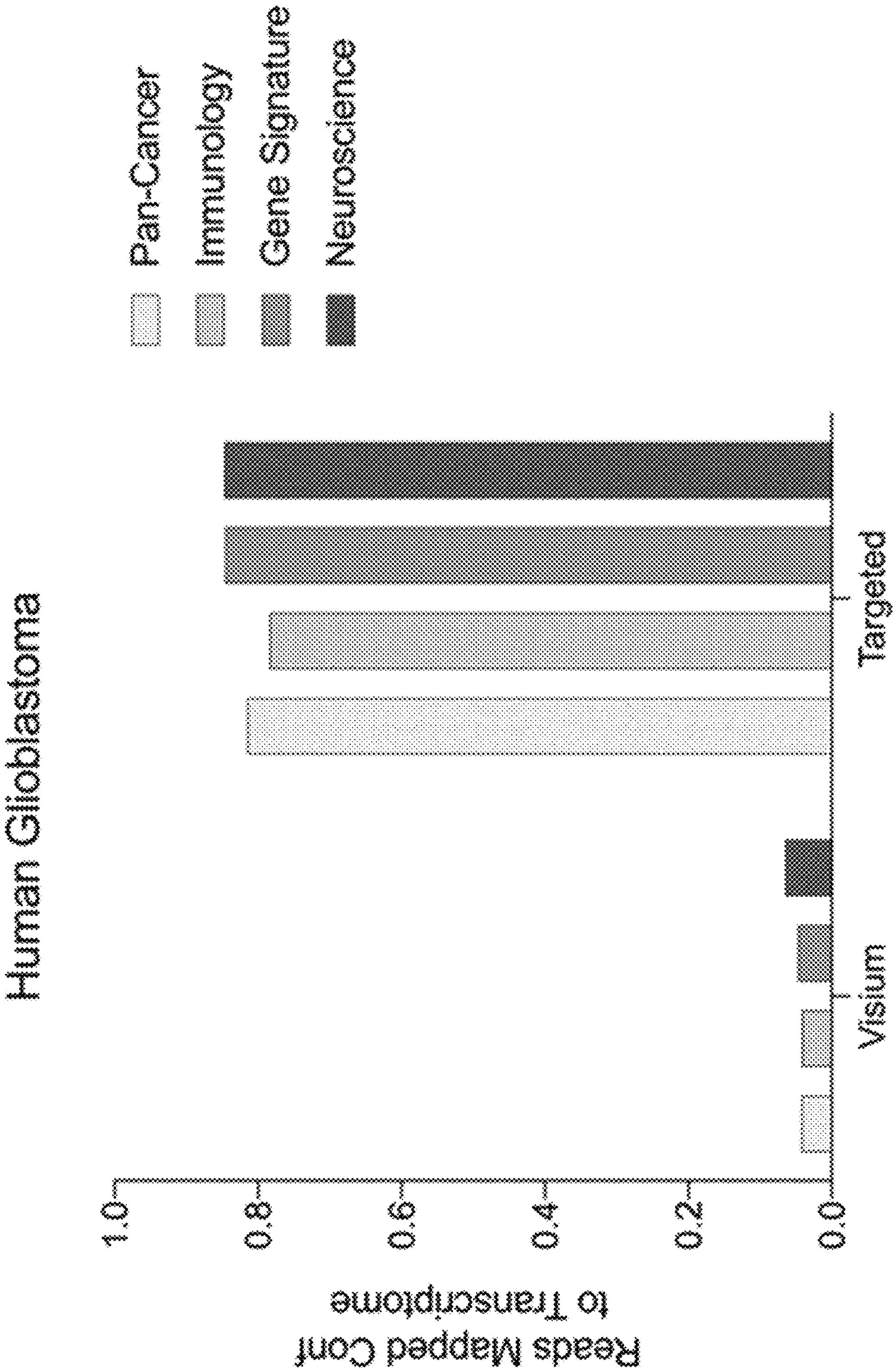
FIGS. 13A-13B are exemplary graphs showing A) mapped reads for whole transcriptome Visium versus four Visium targeted gene panels, and B) UMI count correlation between the Visium whole transcriptome control (X axis) as compared to the Visium targeted Pan Cancer gene panel (Y axis).
Figure 13B:
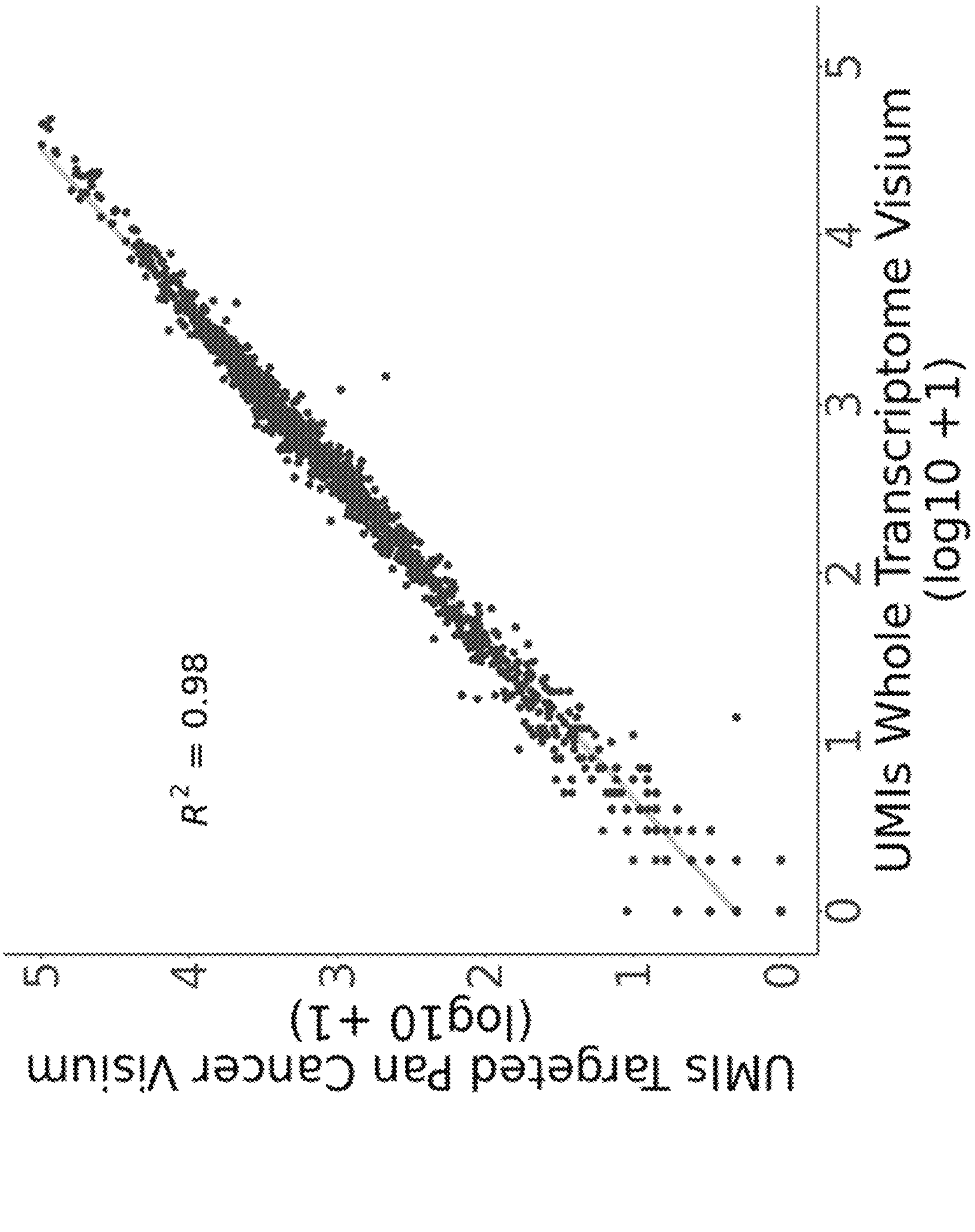

FIGS. 13A-13B show general data results when comparing enrichment of targets using four different gene panels on human glioblastoma tissue sections as compared to a normal whole transcriptome control Visium (non-targeted) spatial array. For all four panels (i.e., Pan-Cancer, Immunology, Gene Signature and Neuroscience enrichment gene panels), on-target reads for the different genes were between 70%-90% regardless of the targeted panel used (FIG. 13A). As shown by the Visium control, roughly 3%-10% of the whole transcriptome mapped reads corresponded to the genes that were in the targeted panels. Further, when comparing the correlation between the Visium control and the Pan-Cancer targeted panel (as a representative targeted panel, but evidenced for all panels), it was observed that the expression profiles were highly reproducible and correlated (R square of 0.98) (FIG. 13B).

Figure 14A:
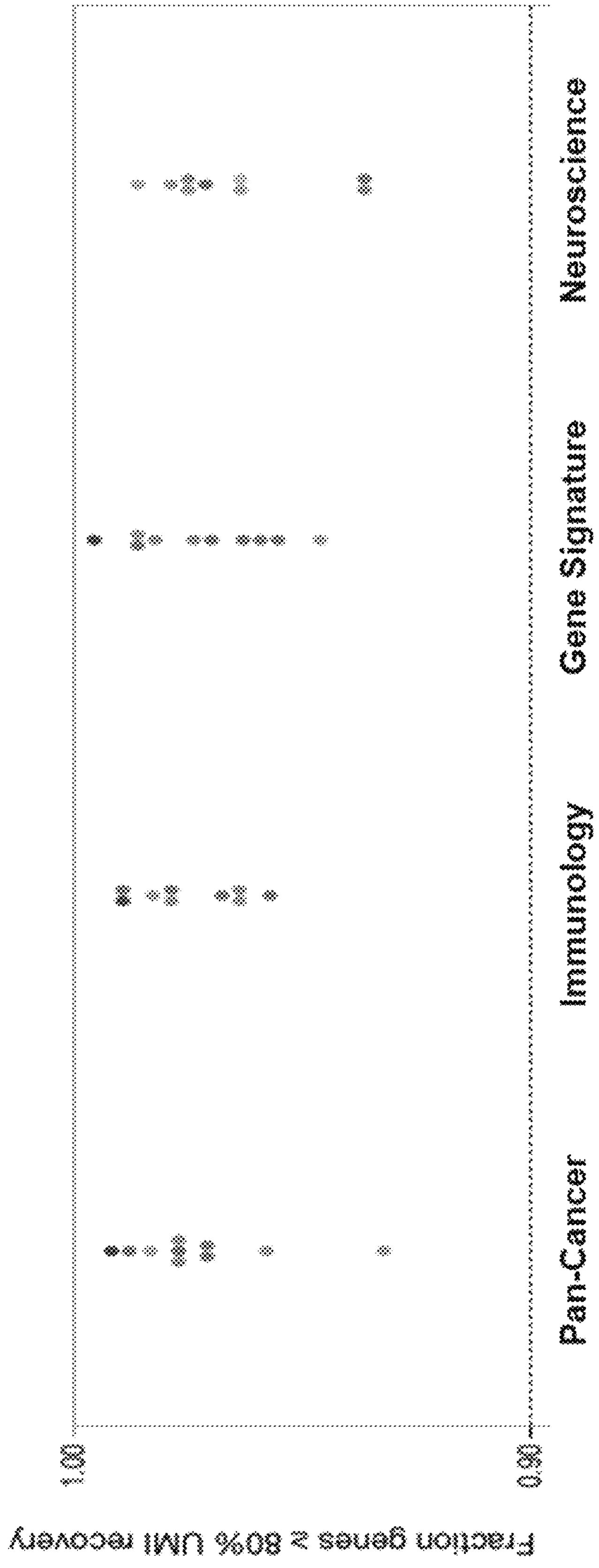
FIGS. 14A-14B are exemplary graphs demonstrating targeted metrics for 12 human tissue type spatial arrays using four targeted gene enrichment panels as compared to a Visium whole transcriptome spatial array for A) fraction of genes recovered against matched Visium whole transcriptome, and B) UMI R-squared concordance against matched Visium whole transcriptome.
Figure 14B:
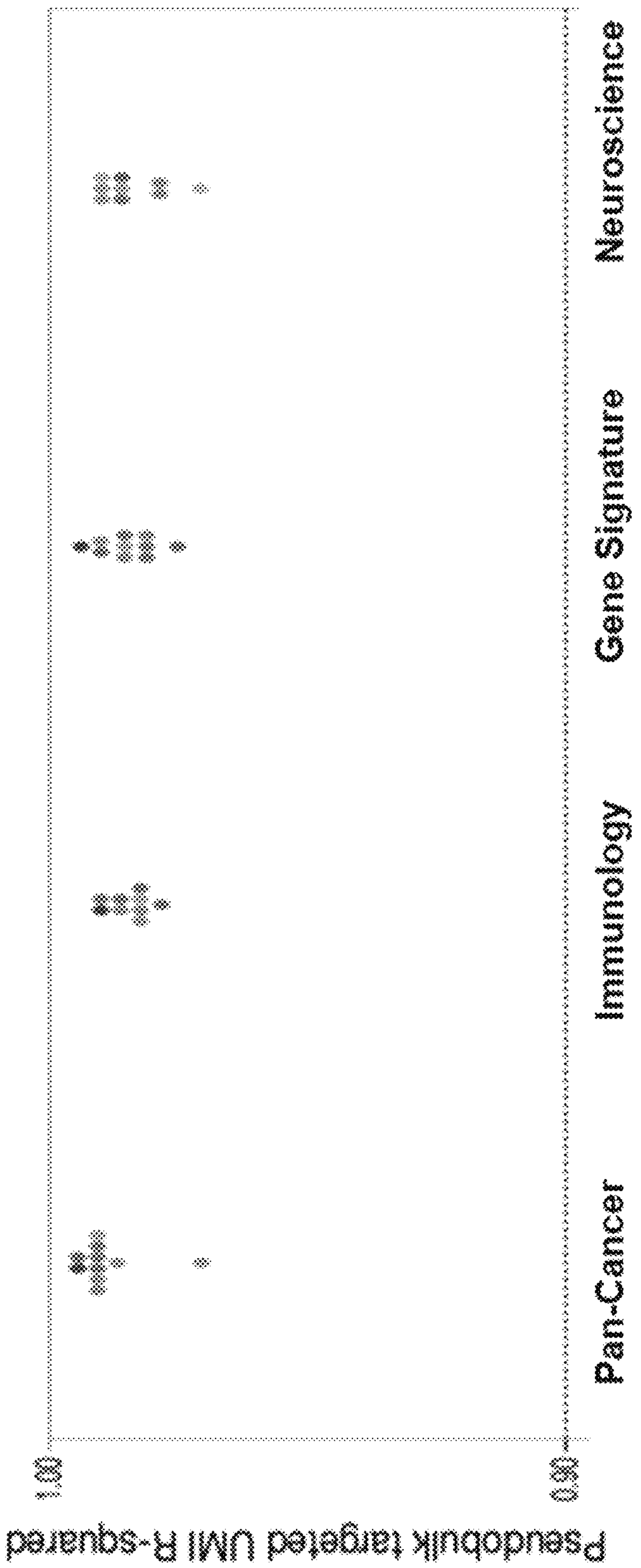

To demonstrate that multiple tissue types are compatible with the targeted gene enrichment workflow, twelve different tissue types were evaluated for each of the four targeted gene panels (FIGS. 14A-14B) against a Visium control whole transcriptome spatial assay. The twelve tissue types tested were all from human: breast IDC, breast ILC, triple negative breast cancer, cerebellum, colorectal cancer, cortex, glioblastoma, heart, kidney diseased, lung, ovarian tumor and spinal cord. Regardless of tissue type or targeted gene enrichment panel, greater than 90% of the targeted genes were recovered (FIG. 14A) with over 80% matched UMIs (FIG. 14B) relative to the control Visium whole transcriptome assay. As such, multiple tissue types are compatible with the targeted gene enrichment workflow described herein.

Figure 15B:
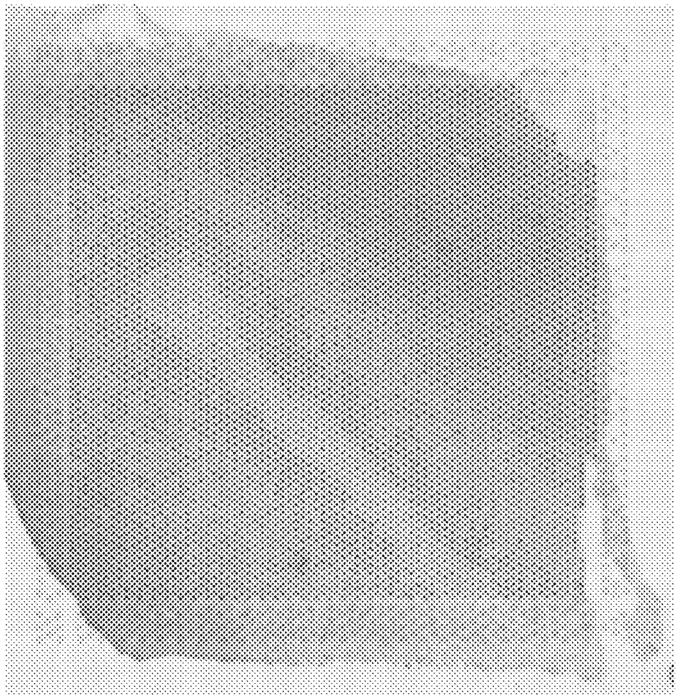
FIGS. 15A-15C demonstrate human cerebral cortex clustering of six gene clusters for A) Visium whole transcriptome and B) neuroscience targeted gene enrichment panel.
Figure 15A:
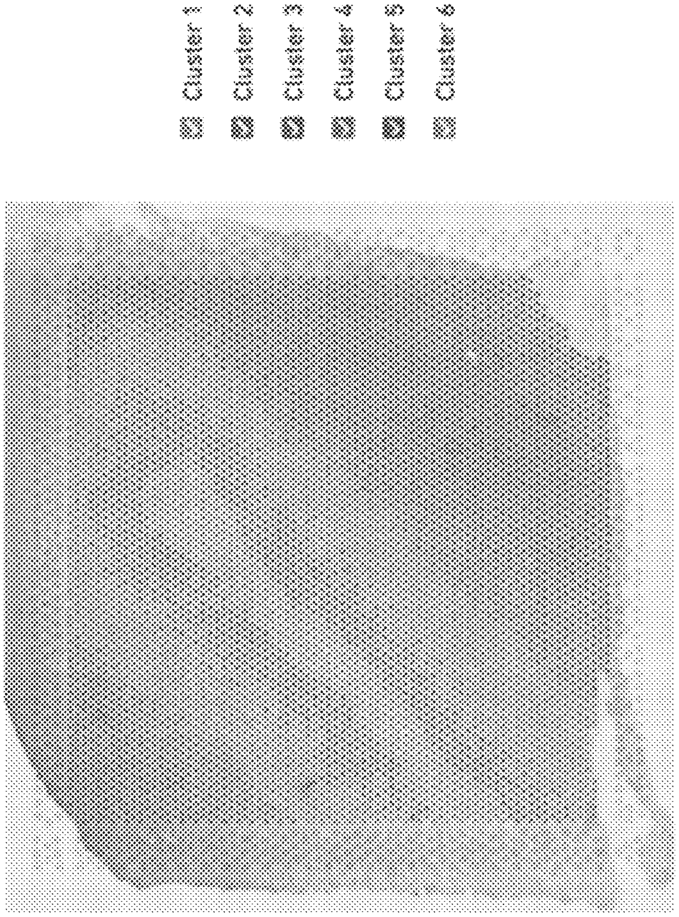
Figure 15C:
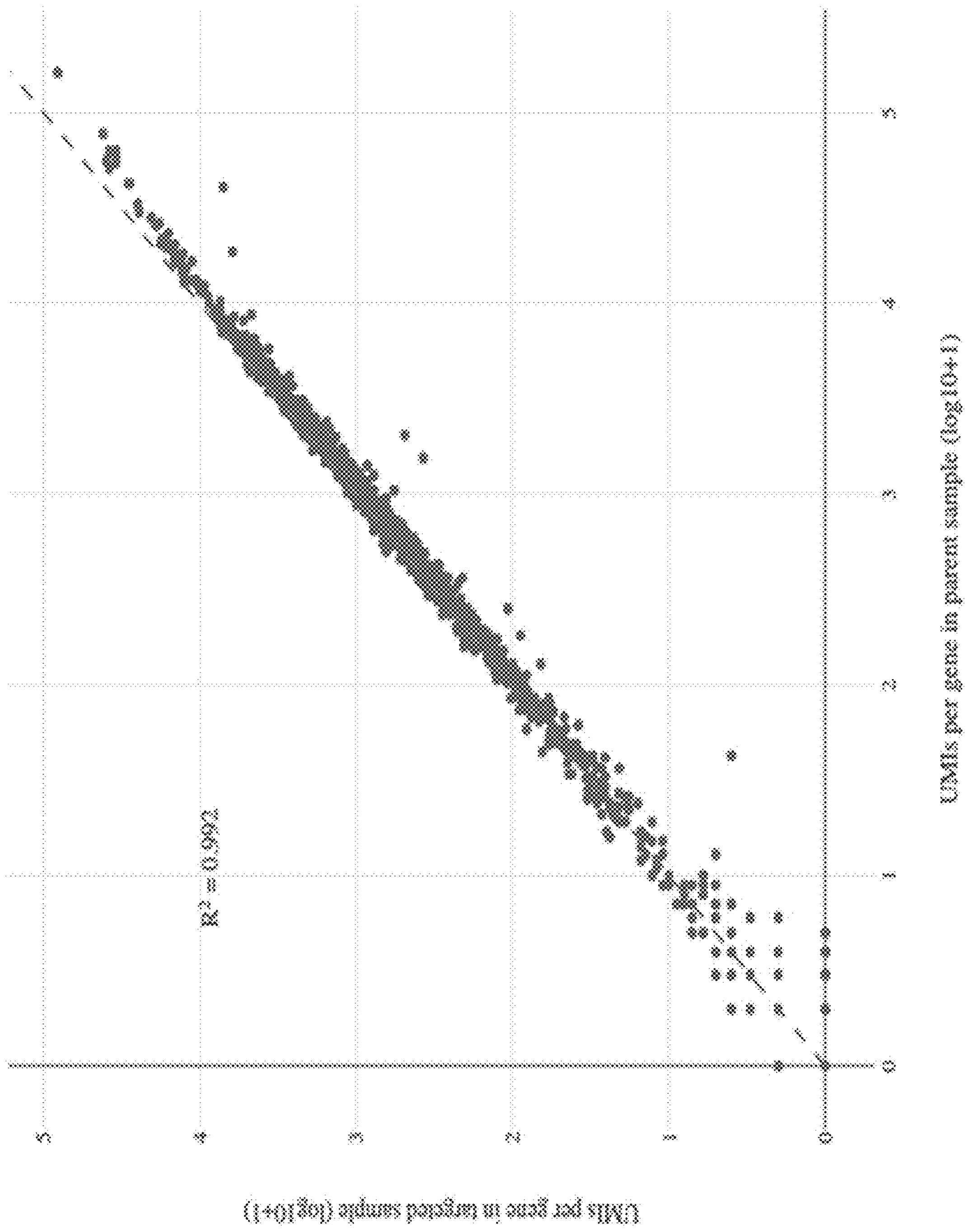

To demonstrate the preservation of clustering when practicing the targeted gene enrichment methods described herein, a Visium whole transcriptome spatial array on human cerebral cortex tissue was compared to a neuroscience panel targeted gene enrichment spatial array. As seen in FIG. 15A (Visium whole transcriptome control) and FIG. 15B (neuroscience panel), clustering was comparable. In fact, for the neuroscience panel, only 5 k raw sequencing reads/spot were needed to recaptilulate the major biological pattern seen with the whole transcriptome assay (50 k reads/spot for the whole transcriptome control). FIG. 15C confirms this data, demonstrating excellent correlation between the two data sets for UMIs plotted per gene.

Figure 16A:
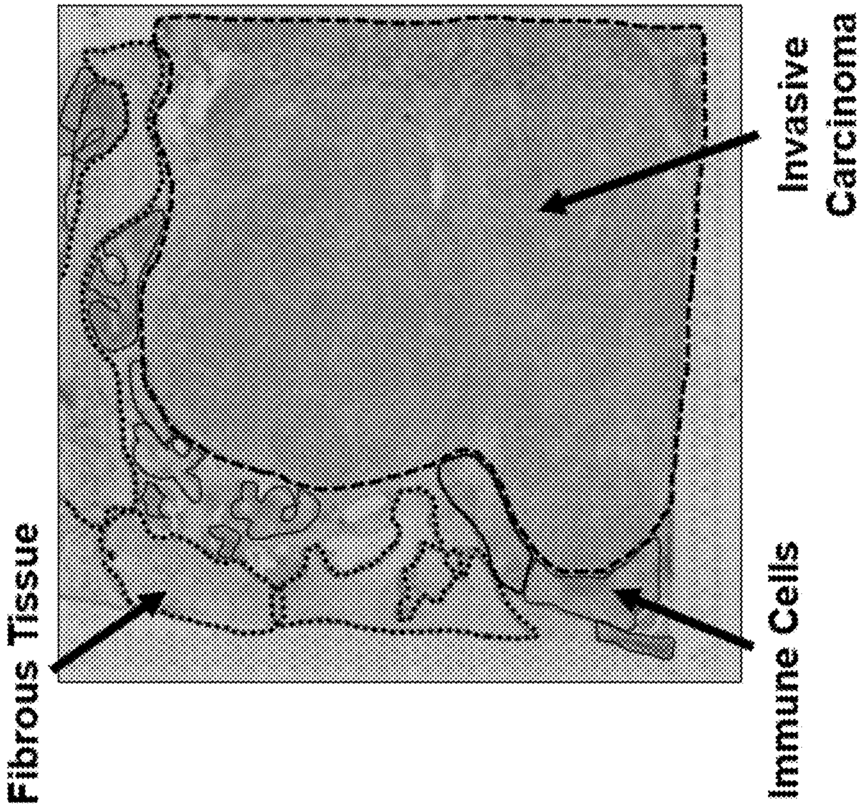
FIGS. 16A-16D show spatial gene expression in a human breast cancer tissue section from the Pan-Cancer gene panel; A) pathologist's annotations (control), B) whole transcriptome Visium data, C) 196 breast cancer genes from the Pan-Cancer enrichment panel and D) ERBB2 gene expression from the Pan-Cancer enrichment panel.
Figure 16B:
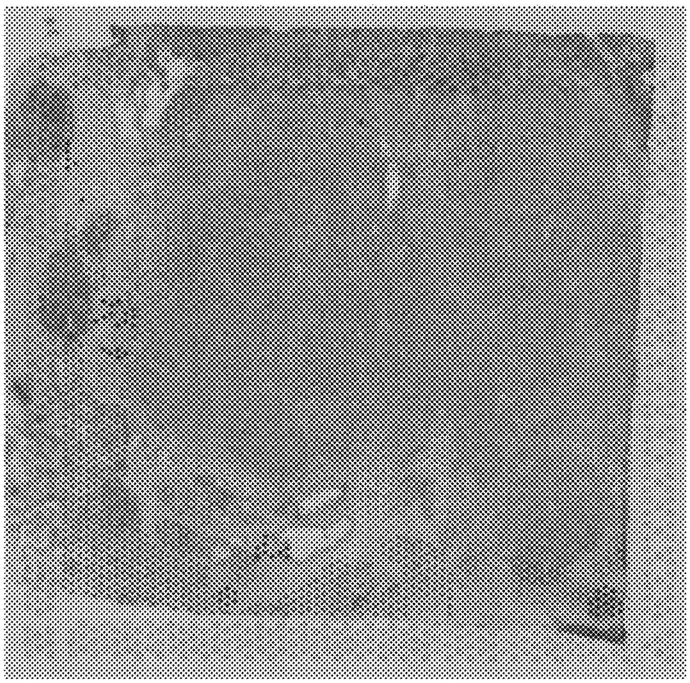
Figure 16D:
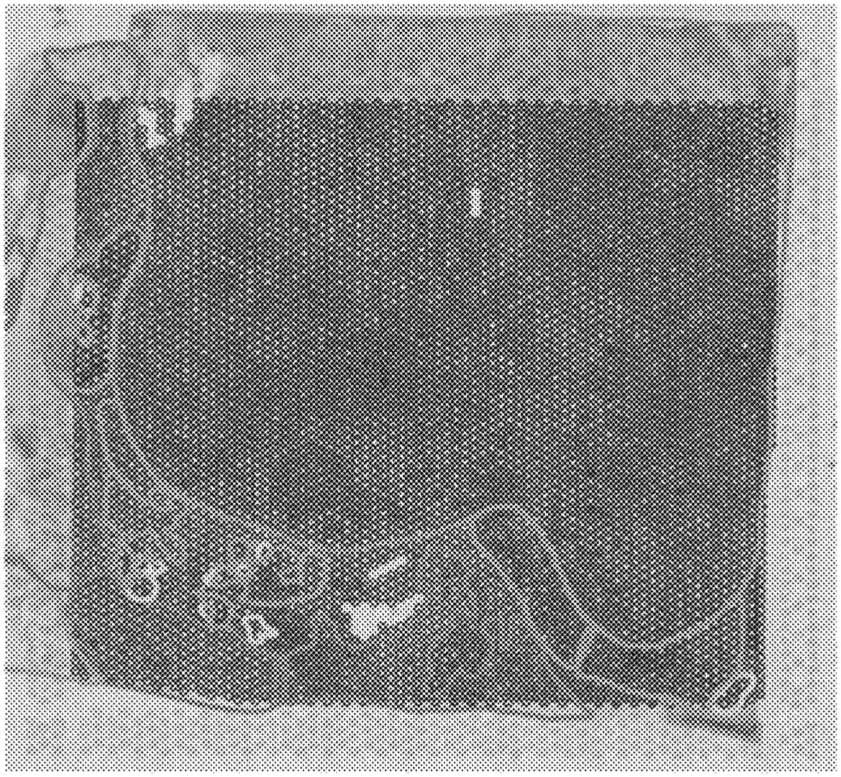
Figure 16C:
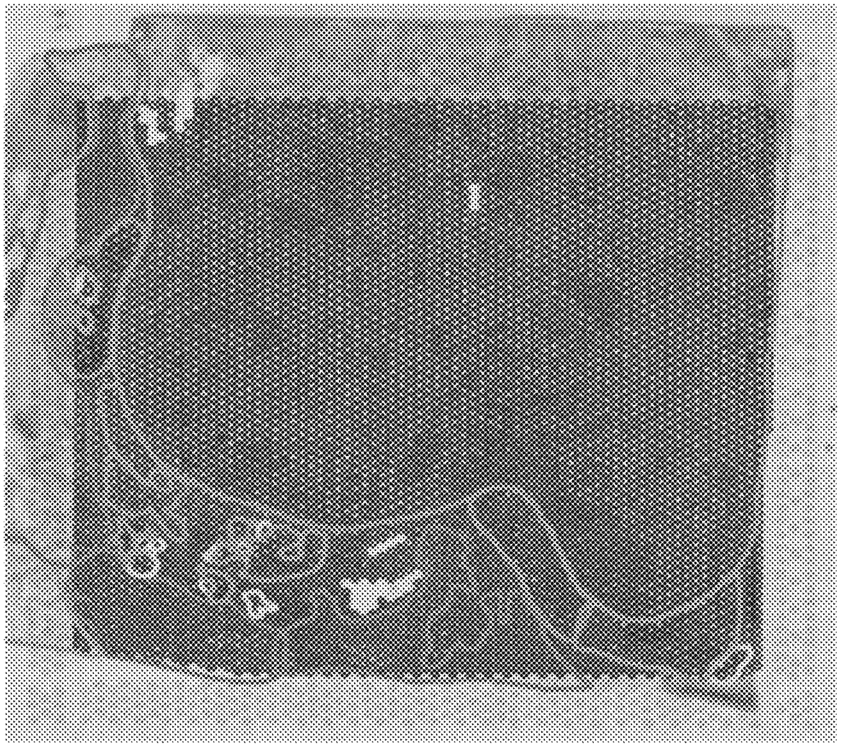

The next question asked was whether the targeted gene panel enrichment protocols could hone in on sub-categories of relevant genes in a tissue, and how that might compare to a pathologist's annotation of a sample. As such, experiments were performed as described herein on human breast cancer tissue sections. FIG. 16A shows a pathologist's annotation for different cells in a breast cancer tissue: DCIS, fat, fibrous tissue, immune cells, invasive carcinoma cells and normal gland cells were identified. Specifically, regions representing invasive carcinoma cells, fibrous tissue, and immune cells are circled by dashed lines, dotted lines, and solid lines, respectively. FIG. 16B shows the pathologist's annotations converted to Visium whole transcriptome data. FIG. 16C shows 196 breast cancer genes from the Pan-Cancer gene enrichment panel, narrowed down to the expression of ERBB2 gene from the Pan-Cancer enrichment panel (FIG. 16D). As seen in the figures, the targeted Pan-Cancer panel following the 196 breast cancer genes from that panel demonstrate that targeted gene expression is comparable to a pathologist's annotation, further that ERBB2 was most abundantly expressed in the invasive carcinoma compartment as expected. Further, all data were obtained using only 5 k reads/spot, as compared to 50 k reads/spot for a Visium whole transcriptome. Such efficiencies require a fraction of the sequencing cost of performing whole transciptome spatial analysis, therefore not only benefitting targeted gene expression but also providing cost savings.

As such, the data demonstrate that for different targeted gene panels, and collectively for all targeted panels, the power of using targeted gene panels with Visium spatial gene expression to identify gene expression information for specific gene targets related to cancer and other diseases important for human health and disease.

What is claimed is:

1. A method for enriching an analyte in a biological sample, which is a tissue sample, wherein the analyte is a nucleic acid which is an RNA molecule, the method comprising:

(a) contacting the biological sample with a substrate comprising a plurality of attached capture probes, wherein a capture probe of the plurality of attached capture probes comprises (i) a spatial barcode and (ii) a capture domain that hybridizes to a sequence present in the analyte;

(b) hybridizing the capture probe to the analyte;

(c) extending a 3' end of the capture probe using the analyte that is bound to the capture probe as a template to generate an extended capture probe;

(d) contacting a plurality of nucleic acids with a plurality of bait oligonucleotides, wherein:

the plurality of nucleic acids comprises the extended capture probe comprising (i) the spatial barcode, or a complement thereof, wherein the spatial barcode is a nucleic acid sequence that provides information as to the location or position of an analyte with in the biological sample, and (ii) all or a portion of a sequence of the analyte, or a complement thereof; and a bait oligonucleotide of the plurality of bait oligonucleotides comprises:

(i) a bait capture domain that hybridizes to a particular exon in the sequence of the analyte from the biological sample, or a complement thereof, and (ii) a molecular tag;

(e) capturing a complex of the bait oligonucleotide bound to the extended capture probe using a second substrate comprising an agent that binds to the molecular tag; and (f) isolating the complex of the bait oligonucleotide bound to the extended capture probe, thereby enriching the analyte in the biological sample.

2. The method of claim 1, further comprising determining (i) the sequence of the spatial barcode or the complement thereof, and (ii) all or a portion of the sequence of the extended capture probe, and using the determined sequences of (i) and (ii), thereby identifying the to identify the location of the analyte in the biological sample.

3. The method of claim 1, further comprising amplifying the extended capture probe.

4. The method of claim 1, wherein the extended capture probe is released from the substrate.

5. The method of claim 1, wherein step (d) and step (e) are performed at substantially the same time.

6. The method of claim 1, wherein the bait capture domain of the bait oligonucleotide comprises a total of about 10 nucleotides to about 300 nucleotides.

7. The method of claim 1, wherein the bait capture domain of the bait oligonucleotide comprises a total of about 120 nucleotides.

8. The method of claim 1, wherein the bait capture domain of the bait oligonucleotide hybridizes to a 3' portion, a 5' portion, an intron, an exon, an untranslated 3' region, or an untranslated 5' region of the sequence of the analyte.

9. The method of claim 1, wherein the molecular tag comprises a protein, a small molecule, a nucleic acid, or a carbohydrate.

10. The method of claim 1, wherein the molecular tag is streptavidin, avidin, biotin, or a fluorophore.

11. The method of claim 1, wherein the agent comprises a protein, a nucleic acid, or a small molecule.

12. The method of claim 1, wherein the molecular tag is biotin and the agent is avidin or streptavidin.

13. The method of claim 1, wherein the agent is attached to the second substrate.

14. The method of claim 13, wherein the second substrate is a bead, a well, or a slide.

15. The method of claim 1, wherein the biological sample is a tissue sample.

16. The method of claim 1, wherein the tissue sample is a formalin-fixed, paraffin-embedded tissue sample.

17. The method of claim 1, wherein the tissue sample is a fresh tissue sample or a frozen tissue sample.

18. The method of claim 1, wherein the biological sample was previously stained using a hematoxylin and eosin stain, immunofluorescence, or immunohistochemistry.

19. The method of claim 18, further comprising imaging the biological sample.

20. The method of claim 2, wherein the determining step comprises sequencing (i) the sequence of the spatial barcode or the complement thereof, and (ii) all or a portion of the extended capture probe.

21. The method of claim 1, wherein the analyte is dysregulated or differentially expressed in a cancer cell, an immune cell, a cellular signaling pathway, or a neurological cell.

22. The method of claim 1, wherein the extended capture probe further comprises a primer sequence or a complement thereof, a unique molecular sequence or a complement thereof, or an additional primer binding sequence or a complement thereof.

23. The method of claim 1, wherein the analyte from the biological sample is associated with a disease or condition.

24. The method of claim 1, wherein the biological sample was previously stained using a detectable label, a hematoxylin and eosin (H&E) stain, immunofluorescence, or immunohistochemistry.

25. The method of claim 1, wherein the extended capture probe comprises DNA.

26. The method of claim 1, further comprising permeabilizing the biological sample with a permeabilization agent comprising pepsin or proteinase K.

* * * * *